United States Patent
Goodman et al.

(10) Patent No.: US 10,392,649 B2
(45) Date of Patent: Aug. 27, 2019

(54) BIOSENSORS THAT DETECT NAD⁺

(71) Applicants: Richard Goodman, Lake Oswego, OR (US); Michael Cohen, Portland, OR (US); Lulu Cambronne, West Linn, OR (US); Melissa Stewart, Oregon City, OR (US)

(72) Inventors: Richard Goodman, Lake Oswego, OR (US); Michael Cohen, Portland, OR (US); Lulu Cambronne, West Linn, OR (US); Melissa Stewart, Oregon City, OR (US)

(73) Assignee: Oregon Health & Science University, Portland, OR (US)

( * ) Notice: Subject to any disclaimer, the term of this patent is extended or adjusted under 35 U.S.C. 154(b) by 194 days.

(21) Appl. No.: 14/948,161

(22) Filed: Nov. 20, 2015

(65) Prior Publication Data
US 2016/0153023 A1 Jun. 2, 2016

Related U.S. Application Data

(60) Provisional application No. 62/086,626, filed on Dec. 2, 2014, provisional application No. 62/235,143, filed on Sep. 30, 2015.

(51) Int. Cl.
*C12Q 1/25* (2006.01)
*C12N 9/00* (2006.01)
*C12Q 1/00* (2006.01)

(52) U.S. Cl.
CPC .............. *C12Q 1/25* (2013.01); *C12N 9/93* (2013.01); *C12Q 1/008* (2013.01); *C12Y 605/01002* (2013.01); *G01N 2333/9015* (2013.01)

(58) Field of Classification Search
None
See application file for complete search history.

(56) References Cited

U.S. PATENT DOCUMENTS

2014/0329718 A1* 11/2014 Yang .................. C07K 14/195
506/10

* cited by examiner

*Primary Examiner* — Anand U Desai

(57) ABSTRACT

A polypeptide biosensor that detects free NAD⁺ is disclosed. The polypeptide comprises a first fragment from an NAD⁺ dependent DNA ligase acetylation domain, a second fragment from the NAD⁺ dependent DNA ligase acetylation domain, and a fluorescent protein, wherein the fluorescent protein is positioned between the two DNA ligase acetylation domain fragments. Also disclosed are expression vectors comprising the biosensor as well as methods of using the biosensor to detect NAD⁺.

20 Claims, 44 Drawing Sheets
(37 of 44 Drawing Sheet(s) Filed in Color)
Specification includes a Sequence Listing.

Figure 22B
| NAD$^+$ [mM] | $\tau_1$ | $A_1$ | $\tau_2$ | $A_2$ | $\tau_3$ | $A_3$ | $<\tau>$ (ns) | $\chi^2$ | Integration time (s) |
|---|---|---|---|---|---|---|---|---|---|
| 0 | 3.0228 | 1644.3 | 1.48552 | 17940 | 0.56656 | 31259 | 0.9703 | 0.858 | 51.991 |
| 0.1 | 2.8408 | 2285 | 1.46806 | 18947 | 0.51788 | 30300 | 0.9702 | 0.914 | 86.168 |
| 0.5 | 2.7017 | 2766.3 | 1.37494 | 19027 | 0.48721 | 30368 | 0.9285 | 0.959 | 106.949 |
| 1.4 | 3.0492 | 1848.9 | 1.49066 | 18419 | 0.53129 | 30884 | 0.9678 | 0.945 | 116.512 |
Figure 23A
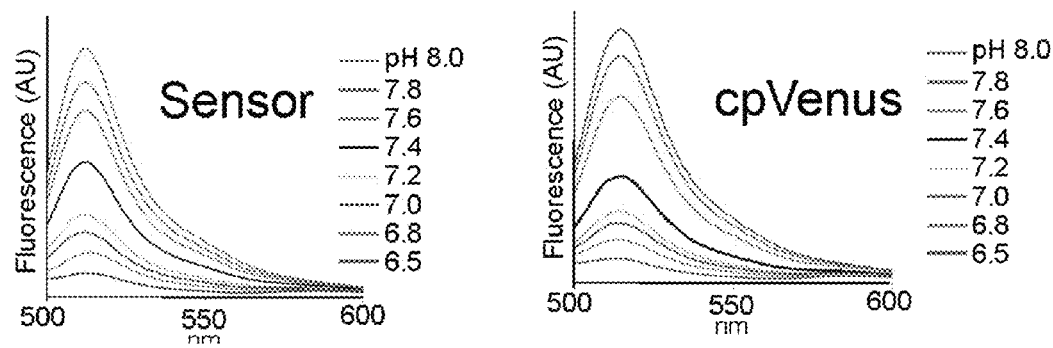
Figure 23B
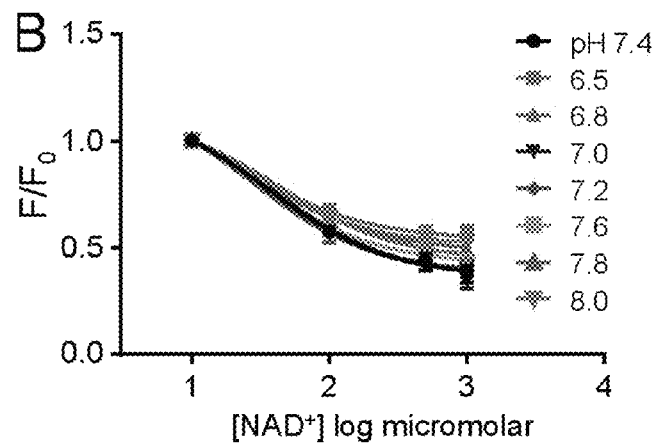

SEQUENCE LISTING

<160> NUMBER OF SEQ ID NOS: 15

<210> SEQ ID NO 1
<211> LENGTH: 69
<212> TYPE: PRT
<213> ORGANISM: Enterococcus faecalis

<400> SEQUENCE: 1

Glu Gln Gln Pro Leu Thr Leu Thr Ala Ala Thr Thr Arg Ala Gln Glu
1               5                   10                  15

Leu Arg Lys Gln Leu Asn Gln Tyr Ser His Glu Tyr Tyr Val Lys Asp
            20                  25                  30

Gln Pro Ser Val Glu Asp Tyr Val Tyr Asp Arg Leu Tyr Lys Glu Leu
        35                  40                  45

Val Asp Ile Glu Thr Glu Phe Pro Asp Leu Ile Thr Pro Asp Ser Pro
    50                  55                  60

Thr Gln Arg Val Gly
65

<210> SEQ ID NO 2
<211> LENGTH: 241
<212> TYPE: PRT
<213> ORGANISM: Enterococcus faecalis

<400> SEQUENCE: 2

Met Glu Lys Ala Pro His Asp Ile Pro Met Tyr Ser Leu Asn Asp Gly
1               5                   10                  15

Phe Ser Lys Glu Asp Ile Phe Ala Phe Asp Glu Arg Val Arg Lys Ala
            20                  25                  30

Ile Gly Lys Pro Val Ala Tyr Cys Cys Glu Leu Leu Ile Asp Gly Leu
        35                  40                  45

Ala Ile Ser Leu Arg Tyr Glu Asn Gly Val Phe Val Arg Gly Ala Thr
    50                  55                  60

Arg Gly Asp Gly Thr Val Gly Glu Asn Ile Thr Glu Asn Leu Arg Thr
65                  70                  75                  80

Val Arg Ser Val Pro Met Arg Leu Thr Glu Pro Ile Ser Val Glu Val
                85                  90                  95

Arg Gly Glu Cys Tyr Met Pro Lys Gln Ser Phe Val Ala Leu Asn Glu
            100                 105                 110

Glu Arg Glu Glu Asn Gly Gln Asp Ile Phe Ala Asn Pro Arg Asn Ala
        115                 120                 125

Ala Ala Gly Ser Leu Arg Gln Leu Asp Thr Lys Ile Val Ala Lys Arg
    130                 135                 140

Asn Leu Asn Thr Phe Leu Tyr Thr Val Ala Asp Phe Gly Pro Met Lys
145                 150                 155                 160

Ala Lys Thr Gln Phe Glu Ala Leu Glu Glu Leu Ser Ala Ile Gly Phe
                165                 170                 175

Arg Thr Asn Pro Glu Arg Gln Leu Cys Gln Ser Ile Asp Glu Val Trp
            180                 185                 190

Ala Tyr Ile Glu Glu Tyr His Glu Lys Arg Ser Thr Leu Pro Tyr Glu
        195                 200                 205

Ile Asn Gly Ile Val Ile Lys Val Asn Glu Phe Ala Leu Gln Asp Glu
    210                 215                 220

Leu Gly Phe Thr Val Lys Ala Pro Arg Trp Ala Ile Ala Tyr Lys Phe
225                 230                 235                 240

Pro

<210> SEQ ID NO 3
<211> LENGTH: 10
<212> TYPE: PRT
<213> ORGANISM: Artificial Sequence
<220> FEATURE:
<223> OTHER INFORMATION: Peptide Linker

<400> SEQUENCE: 3

```
Gly Thr Ile Val Leu Glu Gly Thr Arg Ser
1               5                   10
```

<210> SEQ ID NO 4
<211> LENGTH: 10
<212> TYPE: PRT
<213> ORGANISM: Artificial Sequence
<220> FEATURE:
<223> OTHER INFORMATION: Peptide Linker

<400> SEQUENCE: 4

```
Thr Gly Arg Gly Arg Val Tyr Ser Ala Gly
1               5                   10
```

<210> SEQ ID NO 5
<211> LENGTH: 244
<212> TYPE: PRT
<213> ORGANISM: Aequorea victoria

<400> SEQUENCE: 5

```
Tyr Asn Ser Asp Asn Val Tyr Ile Thr Ala Asp Lys Gln Lys Asn Gly
1               5                   10                  15

Ile Lys Ala Asn Phe Lys Ile Arg His Asn Ile Glu Asp Gly Gly Val
            20                  25                  30

Gln Leu Ala Asp His Tyr Gln Gln Asn Thr Pro Ile Gly Asp Gly Pro
        35                  40                  45

Val Leu Leu Pro Asp Asn His Tyr Leu Ser Phe Gln Ser Lys Leu Ser
    50                  55                  60

Lys Asp Pro Asn Glu Lys Arg Asp His Met Val Leu Leu Glu Phe Val
65                  70                  75                  80

Thr Ala Ala Gly Ile Thr Leu Gly Met Asp Glu Leu Tyr Lys Gly Gly
                85                  90                  95

Ser Gly Gly Met Val Ser Lys Gly Glu Glu Leu Phe Thr Gly Val Val
            100                 105                 110

Pro Ile Leu Val Glu Leu Asp Gly Asp Val Asn Gly His Lys Phe Ser
        115                 120                 125

Val Ser Gly Glu Gly Glu Gly Asp Ala Thr Tyr Gly Lys Leu Thr Leu
    130                 135                 140

Lys Leu Ile Cys Thr Thr Gly Lys Leu Pro Val Pro Trp Pro Thr Leu
145                 150                 155                 160

Val Thr Thr Leu Gly Tyr Gly Leu Gln Cys Phe Ala Arg Tyr Pro Asp
                165                 170                 175

His Met Lys Gln His Asp Phe Phe Lys Ser Ala Met Pro Glu Gly Tyr
            180                 185                 190

Val Gln Glu Arg Thr Ile Phe Phe Lys Asp Asp Gly Asn Tyr Lys Thr
        195                 200                 205

Arg Ala Glu Val Lys Phe Glu Gly Asp Thr Leu Val Asn Arg Ile Glu
    210                 215                 220

Leu Lys Gly Ile Asp Phe Lys Glu Asp Gly Asn Ile Leu Gly His Lys
225                 230                 235                 240
```

Leu Glu Tyr Asn

<210> SEQ ID NO 6
<211> LENGTH: 604
<212> TYPE: PRT
<213> ORGANISM: Artificial Sequence
<220> FEATURE:
<223> OTHER INFORMATION: NAD+ Biosensor

<400> SEQUENCE: 6

Met Asp Tyr Lys Asp Asp Asp Lys Leu Asp Gly Gly Tyr Pro Tyr
1               5                   10                  15

Asp Val Pro Asp Tyr Ala Ala Arg Gly Tyr Gln Thr Ser Leu Tyr Lys
            20                  25                  30

Lys Ala Gly Ser Thr Met Gly His Met Glu Lys Ala Pro His Asp Ile
                35                  40                  45

Pro Met Tyr Ser Leu Asn Asp Gly Phe Ser Lys Glu Asp Ile Phe Ala
    50                  55                  60

Phe Asp Glu Arg Val Arg Lys Ala Ile Gly Lys Pro Val Ala Tyr Cys
65                  70                  75                  80

Cys Glu Leu Leu Ile Asp Gly Leu Ala Ile Ser Leu Arg Tyr Glu Asn
                85                  90                  95

Gly Val Phe Val Arg Gly Ala Thr Arg Gly Asp Gly Thr Val Gly Glu
            100                 105                 110

Asn Ile Thr Glu Asn Leu Arg Thr Val Arg Ser Val Pro Met Arg Leu
        115                 120                 125

Thr Glu Pro Ile Ser Val Glu Val Arg Gly Glu Cys Tyr Met Pro Lys
    130                 135                 140

Gln Ser Phe Val Ala Leu Asn Glu Glu Arg Glu Glu Asn Gly Gln Asp
145                 150                 155                 160

Ile Phe Ala Asn Pro Arg Asn Ala Ala Ala Gly Ser Leu Arg Gln Leu
                165                 170                 175

Asp Thr Lys Ile Val Ala Lys Arg Asn Leu Asn Thr Phe Leu Tyr Thr
            180                 185                 190

Val Ala Asp Phe Gly Pro Met Lys Ala Lys Thr Gln Phe Glu Ala Leu
        195                 200                 205

Glu Glu Leu Ser Ala Ile Gly Phe Arg Thr Asn Pro Glu Arg Gln Leu
    210                 215                 220

Cys Gln Ser Ile Asp Glu Val Trp Ala Tyr Ile Glu Glu Tyr His Glu
225                 230                 235                 240

Lys Arg Ser Thr Leu Pro Tyr Glu Ile Asn Gly Ile Val Ile Lys Val
                245                 250                 255

Asn Glu Phe Ala Leu Gln Asp Glu Leu Gly Phe Thr Val Lys Ala Pro
            260                 265                 270

Arg Trp Ala Ile Ala Tyr Lys Phe Pro Tyr Asn Ser Asp Asn Val Tyr
        275                 280                 285

Ile Thr Ala Asp Lys Gln Lys Asn Gly Ile Lys Ala Asn Phe Lys Ile
    290                 295                 300

Arg His Asn Ile Glu Asp Gly Gly Val Gln Leu Ala Asp His Tyr Gln
305                 310                 315                 320

Gln Asn Thr Pro Ile Gly Asp Gly Pro Val Leu Leu Pro Asp Asn His
                325                 330                 335

Tyr Leu Ser Phe Gln Ser Lys Leu Ser Lys Asp Pro Asn Glu Lys Arg
            340                 345                 350

Asp His Met Val Leu Leu Glu Phe Val Thr Ala Ala Gly Ile Thr Leu
            355                 360                 365

Gly Met Asp Glu Leu Tyr Lys Gly Gly Ser Gly Gly Met Val Ser Lys
370                 375                 380

Gly Glu Glu Leu Phe Thr Gly Val Val Pro Ile Leu Val Glu Leu Asp
385                 390                 395                 400

Gly Asp Val Asn Gly His Lys Phe Ser Val Ser Gly Glu Gly Glu Gly
                405                 410                 415

Asp Ala Thr Tyr Gly Lys Leu Thr Lys Leu Ile Cys Thr Thr Gly
            420                 425                 430

Lys Leu Pro Val Pro Trp Pro Thr Leu Val Thr Thr Leu Gly Tyr Gly
            435                 440                 445

Leu Gln Cys Phe Ala Arg Tyr Pro Asp His Met Lys Gln His Asp Phe
            450                 455                 460

Phe Lys Ser Ala Met Pro Glu Gly Tyr Val Gln Glu Arg Thr Ile Phe
465                 470                 475                 480

Phe Lys Asp Asp Gly Asn Tyr Lys Thr Arg Ala Glu Val Lys Phe Glu
                485                 490                 495

Gly Asp Thr Leu Val Asn Arg Ile Glu Leu Lys Gly Ile Asp Phe Lys
            500                 505                 510

Glu Asp Gly Asn Ile Leu Gly His Lys Leu Glu Tyr Asn Gly Thr Ile
            515                 520                 525

Val Leu Glu Gly Thr Arg Ser Glu Gln Gln Pro Leu Thr Leu Thr Ala
            530                 535                 540

Ala Thr Thr Arg Ala Gln Glu Leu Arg Lys Gln Leu Asn Gln Tyr Ser
545                 550                 555                 560

His Glu Tyr Tyr Val Lys Asp Gln Pro Ser Val Glu Asp Tyr Val Tyr
                565                 570                 575

Asp Arg Leu Tyr Lys Glu Leu Val Asp Ile Glu Thr Glu Phe Pro Asp
            580                 585                 590

Leu Ile Thr Pro Asp Ser Pro Thr Gln Arg Val Gly
            595                 600

<210> SEQ ID NO 7
<211> LENGTH: 629
<212> TYPE: PRT
<213> ORGANISM: Artificial Sequence
<220> FEATURE:
<223> OTHER INFORMATION: NAD+ Biosensor

<400> SEQUENCE: 7

Met Leu Ala Thr Arg Val Phe Ser Leu Val Gly Lys Arg Ala Ile Ser
1               5                   10                  15

Thr Ser Val Cys Val Arg Ala His Thr Gly Asp Tyr Lys Asp Asp Asp
            20                  25                  30

Asp Lys Leu Asp Gly Gly Tyr Pro Tyr Asp Val Pro Asp Tyr Ala Ala
            35                  40                  45

Arg Gly Tyr Gln Thr Ser Leu Tyr Lys Lys Ala Gly Ser Thr Met Gly
            50                  55                  60

His Met Glu Lys Ala Pro His Asp Ile Pro Met Tyr Ser Leu Asn Asp
65                  70                  75                  80

Gly Phe Ser Lys Glu Asp Ile Phe Ala Phe Asp Glu Arg Val Arg Lys
                85                  90                  95

Ala Ile Gly Lys Pro Val Ala Tyr Cys Cys Glu Leu Leu Ile Asp Gly
            100                 105                 110

```
Leu Ala Ile Ser Leu Arg Tyr Glu Asn Gly Val Phe Val Arg Gly Ala
            115                 120                 125

Thr Arg Gly Asp Gly Thr Val Gly Glu Asn Ile Thr Glu Asn Leu Arg
    130                 135                 140

Thr Val Arg Ser Val Pro Met Arg Leu Thr Glu Pro Ile Ser Val Glu
145                 150                 155                 160

Val Arg Gly Glu Cys Tyr Met Pro Lys Gln Ser Phe Val Ala Leu Asn
                165                 170                 175

Glu Glu Arg Glu Asn Gly Gln Asp Ile Phe Ala Asn Pro Arg Asn
            180                 185                 190

Ala Ala Ala Gly Ser Leu Arg Gln Leu Asp Thr Lys Ile Val Ala Lys
            195                 200                 205

Arg Asn Leu Asn Thr Phe Leu Tyr Thr Val Ala Asp Phe Gly Pro Met
    210                 215                 220

Lys Ala Lys Thr Gln Phe Glu Ala Leu Glu Glu Leu Ser Ala Ile Gly
225                 230                 235                 240

Phe Arg Thr Asn Pro Glu Arg Gln Leu Cys Gln Ser Ile Asp Glu Val
                245                 250                 255

Trp Ala Tyr Ile Glu Glu Tyr His Glu Lys Arg Ser Thr Leu Pro Tyr
            260                 265                 270

Glu Ile Asn Gly Ile Val Ile Lys Val Asn Glu Phe Ala Leu Gln Asp
    275                 280                 285

Glu Leu Gly Phe Thr Val Lys Ala Pro Arg Trp Ala Ile Ala Tyr Lys
    290                 295                 300

Phe Pro Tyr Asn Ser Asp Asn Val Tyr Ile Thr Ala Asp Lys Gln Lys
305                 310                 315                 320

Asn Gly Ile Lys Ala Asn Phe Lys Ile Arg His Asn Ile Glu Asp Gly
                325                 330                 335

Gly Val Gln Leu Ala Asp His Tyr Gln Gln Asn Thr Pro Ile Gly Asp
            340                 345                 350

Gly Pro Val Leu Leu Pro Asp Asn His Tyr Leu Ser Phe Gln Ser Lys
            355                 360                 365

Leu Ser Lys Asp Pro Asn Glu Lys Arg Asp His Met Val Leu Leu Glu
    370                 375                 380

Phe Val Thr Ala Ala Gly Ile Thr Leu Gly Met Asp Glu Leu Tyr Lys
385                 390                 395                 400

Gly Gly Ser Gly Gly Met Val Ser Lys Gly Glu Glu Leu Phe Thr Gly
                405                 410                 415

Val Val Pro Ile Leu Val Glu Leu Asp Gly Asp Val Asn Gly His Lys
            420                 425                 430

Phe Ser Val Ser Gly Glu Gly Glu Gly Asp Ala Thr Tyr Gly Lys Leu
            435                 440                 445

Thr Leu Lys Leu Ile Cys Thr Thr Gly Lys Leu Pro Val Pro Trp Pro
    450                 455                 460

Thr Leu Val Thr Thr Leu Gly Tyr Gly Leu Gln Cys Phe Ala Arg Tyr
465                 470                 475                 480

Pro Asp His Met Lys Gln His Asp Phe Phe Lys Ser Ala Met Pro Glu
                485                 490                 495

Gly Tyr Val Gln Glu Arg Thr Ile Phe Phe Lys Asp Asp Gly Asn Tyr
            500                 505                 510

Lys Thr Arg Ala Glu Val Lys Phe Glu Gly Asp Thr Leu Val Asn Arg
            515                 520                 525

Ile Glu Leu Lys Gly Ile Asp Phe Lys Glu Asp Gly Asn Ile Leu Gly
```

```
                    530                 535                 540
His Lys Leu Glu Tyr Asn Gly Thr Ile Val Leu Glu Gly Thr Arg Ser
545                 550                 555                 560

Glu Gln Gln Pro Leu Thr Leu Thr Ala Ala Thr Thr Arg Ala Gln Glu
                565                 570                 575

Leu Arg Lys Gln Leu Asn Gln Tyr Ser His Glu Tyr Tyr Val Lys Asp
                580                 585                 590

Gln Pro Ser Val Glu Asp Tyr Val Tyr Asp Arg Leu Tyr Lys Glu Leu
                595                 600                 605

Val Asp Ile Glu Thr Glu Phe Pro Asp Leu Ile Thr Pro Asp Ser Pro
            610                 615                 620

Thr Gln Arg Val Gly
625

<210> SEQ ID NO 8
<211> LENGTH: 617
<212> TYPE: PRT
<213> ORGANISM: Artificial Sequence
<220> FEATURE:
<223> OTHER INFORMATION: NAD+ Biosensor

<400> SEQUENCE: 8

Met Thr Gly Leu Gln Lys Lys Leu Glu Glu Leu Glu Leu Asp Asp Tyr
1               5                   10                  15

Lys Asp Asp Asp Asp Lys Leu Asp Gly Gly Tyr Pro Tyr Asp Val Pro
                20                  25                  30

Asp Tyr Ala Ala Arg Gly Tyr Gln Thr Ser Leu Tyr Lys Lys Ala Gly
            35                  40                  45

Ser Thr Met Gly His Met Glu Lys Ala Pro His Asp Ile Pro Met Tyr
50                  55                  60

Ser Leu Asn Asp Gly Phe Ser Lys Glu Asp Ile Phe Ala Phe Asp Glu
65                  70                  75                  80

Arg Val Arg Lys Ala Ile Gly Lys Pro Val Ala Tyr Cys Cys Glu Leu
                85                  90                  95

Leu Ile Asp Gly Leu Ala Ile Ser Leu Arg Tyr Glu Asn Gly Val Phe
            100                 105                 110

Val Arg Gly Ala Thr Arg Gly Asp Gly Thr Val Gly Glu Asn Ile Thr
        115                 120                 125

Glu Asn Leu Arg Thr Val Arg Ser Val Pro Met Arg Leu Thr Glu Pro
130                 135                 140

Ile Ser Val Glu Val Arg Gly Glu Cys Tyr Met Pro Lys Gln Ser Phe
145                 150                 155                 160

Val Ala Leu Asn Glu Glu Arg Glu Asn Gly Gln Asp Ile Phe Ala
                165                 170                 175

Asn Pro Arg Asn Ala Ala Ala Gly Ser Leu Arg Gln Leu Asp Thr Lys
            180                 185                 190

Ile Val Ala Lys Arg Asn Leu Asn Thr Phe Leu Tyr Thr Val Ala Asp
        195                 200                 205

Phe Gly Pro Met Lys Ala Lys Thr Gln Phe Glu Ala Leu Glu Glu Leu
        210                 215                 220

Ser Ala Ile Gly Phe Arg Thr Asn Pro Glu Arg Gln Leu Cys Gln Ser
225                 230                 235                 240

Ile Asp Glu Val Trp Ala Tyr Ile Glu Glu Tyr His Glu Lys Arg Ser
                245                 250                 255

Thr Leu Pro Tyr Glu Ile Asn Gly Ile Val Ile Lys Val Asn Glu Phe
```

```
                260                 265                 270
Ala Leu Gln Asp Glu Leu Gly Phe Thr Val Lys Ala Pro Arg Trp Ala
            275                 280                 285

Ile Ala Tyr Lys Phe Pro Tyr Asn Ser Asp Asn Val Tyr Ile Thr Ala
            290                 295                 300

Asp Lys Gln Lys Asn Gly Ile Lys Ala Asn Phe Lys Ile Arg His Asn
305                 310                 315                 320

Ile Glu Asp Gly Gly Val Gln Leu Ala Asp His Tyr Gln Gln Asn Thr
                325                 330                 335

Pro Ile Gly Asp Gly Pro Val Leu Leu Pro Asp Asn His Tyr Leu Ser
            340                 345                 350

Phe Gln Ser Lys Leu Ser Lys Asp Pro Asn Glu Lys Arg Asp His Met
            355                 360                 365

Val Leu Leu Glu Phe Val Thr Ala Ala Gly Ile Thr Leu Gly Met Asp
            370                 375                 380

Glu Leu Tyr Lys Gly Gly Ser Gly Gly Met Val Ser Lys Gly Glu Glu
385                 390                 395                 400

Leu Phe Thr Gly Val Val Pro Ile Leu Val Glu Leu Asp Gly Asp Val
                405                 410                 415

Asn Gly His Lys Phe Ser Val Ser Gly Glu Gly Glu Gly Asp Ala Thr
            420                 425                 430

Tyr Gly Lys Leu Thr Leu Lys Leu Ile Cys Thr Thr Gly Lys Leu Pro
            435                 440                 445

Val Pro Trp Pro Thr Leu Val Thr Thr Leu Gly Tyr Gly Leu Gln Cys
450                 455                 460

Phe Ala Arg Tyr Pro Asp His Met Lys Gln His Asp Phe Phe Lys Ser
465                 470                 475                 480

Ala Met Pro Glu Gly Tyr Val Gln Glu Arg Thr Ile Phe Phe Lys Asp
                485                 490                 495

Asp Gly Asn Tyr Lys Thr Arg Ala Glu Val Lys Phe Glu Gly Asp Thr
            500                 505                 510

Leu Val Asn Arg Ile Glu Leu Lys Gly Ile Asp Phe Lys Glu Asp Gly
            515                 520                 525

Asn Ile Leu Gly His Lys Leu Glu Tyr Asn Gly Thr Ile Val Leu Glu
            530                 535                 540

Gly Thr Arg Ser Glu Gln Gln Pro Leu Thr Leu Thr Ala Ala Thr Thr
545                 550                 555                 560

Arg Ala Gln Glu Leu Arg Lys Gln Leu Asn Gln Tyr Ser His Glu Tyr
                565                 570                 575

Tyr Val Lys Asp Gln Pro Ser Val Glu Asp Tyr Val Tyr Asp Arg Leu
            580                 585                 590

Tyr Lys Glu Leu Val Asp Ile Glu Thr Glu Phe Pro Asp Leu Ile Thr
            595                 600                 605

Pro Asp Ser Pro Thr Gln Arg Val Gly
    610                 615

<210> SEQ ID NO 9
<211> LENGTH: 613
<212> TYPE: PRT
<213> ORGANISM: Artificial Sequence
<220> FEATURE:
<223> OTHER INFORMATION: NAD+ Biosensor

<400> SEQUENCE: 9

Met Thr Gly Pro Lys Lys Lys Arg Lys Val Asp Tyr Lys Asp Asp Asp
```

-continued

```
1               5                   10                  15
Asp Lys Leu Asp Gly Gly Tyr Pro Tyr Asp Val Pro Asp Tyr Ala Ala
                20                  25                  30
Arg Gly Tyr Gln Thr Ser Leu Tyr Lys Lys Ala Gly Ser Thr Met Gly
                35                  40                  45
His Met Glu Lys Ala Pro His Asp Ile Pro Met Tyr Ser Leu Asn Asp
    50                  55                  60
Gly Phe Ser Lys Glu Asp Ile Phe Ala Phe Asp Glu Arg Val Arg Lys
65                  70                  75                  80
Ala Ile Gly Lys Pro Val Ala Tyr Cys Cys Glu Leu Leu Ile Asp Gly
                    85                  90                  95
Leu Ala Ile Ser Leu Arg Tyr Glu Asn Gly Val Phe Val Arg Gly Ala
                100                 105                 110
Thr Arg Gly Asp Gly Thr Val Gly Glu Asn Ile Thr Glu Asn Leu Arg
                115                 120                 125
Thr Val Arg Ser Val Pro Met Arg Leu Thr Glu Pro Ile Ser Val Glu
130                 135                 140
Val Arg Gly Glu Cys Tyr Met Pro Lys Gln Ser Phe Val Ala Leu Asn
145                 150                 155                 160
Glu Glu Arg Glu Glu Asn Gly Gln Asp Ile Phe Ala Asn Pro Arg Asn
                165                 170                 175
Ala Ala Ala Gly Ser Leu Arg Gln Leu Asp Thr Lys Ile Val Ala Lys
                180                 185                 190
Arg Asn Leu Asn Thr Phe Leu Tyr Thr Val Ala Asp Phe Gly Pro Met
                195                 200                 205
Lys Ala Lys Thr Gln Phe Glu Ala Leu Glu Glu Leu Ser Ala Ile Gly
    210                 215                 220
Phe Arg Thr Asn Pro Glu Arg Gln Leu Cys Gln Ser Ile Asp Glu Val
225                 230                 235                 240
Trp Ala Tyr Ile Glu Glu Tyr His Glu Lys Arg Ser Thr Leu Pro Tyr
                    245                 250                 255
Glu Ile Asn Gly Ile Val Ile Lys Val Asn Glu Phe Ala Leu Gln Asp
                260                 265                 270
Glu Leu Gly Phe Thr Val Lys Ala Pro Arg Trp Ala Ile Ala Tyr Lys
                275                 280                 285
Phe Pro Tyr Asn Ser Asp Asn Val Tyr Ile Thr Ala Asp Lys Gln Lys
                290                 295                 300
Asn Gly Ile Lys Ala Asn Phe Lys Ile Arg His Asn Ile Glu Asp Gly
305                 310                 315                 320
Gly Val Gln Leu Ala Asp His Tyr Gln Gln Asn Thr Pro Ile Gly Asp
                325                 330                 335
Gly Pro Val Leu Leu Pro Asp Asn His Tyr Leu Ser Phe Gln Ser Lys
                340                 345                 350
Leu Ser Lys Asp Pro Asn Glu Lys Arg Asp His Met Val Leu Leu Glu
                355                 360                 365
Phe Val Thr Ala Ala Gly Ile Thr Leu Gly Met Asp Glu Leu Tyr Lys
                370                 375                 380
Gly Gly Ser Gly Gly Met Val Ser Lys Gly Glu Glu Leu Phe Thr Gly
385                 390                 395                 400
Val Val Pro Ile Leu Val Glu Leu Asp Gly Asp Val Asn Gly His Lys
                405                 410                 415
Phe Ser Val Ser Gly Glu Gly Glu Gly Asp Ala Thr Tyr Gly Lys Leu
                420                 425                 430
```

-continued

```
Thr Leu Lys Leu Ile Cys Thr Thr Gly Lys Leu Pro Val Pro Trp Pro
            435                 440                 445

Thr Leu Val Thr Thr Leu Gly Tyr Gly Leu Gln Cys Phe Ala Arg Tyr
            450                 455                 460

Pro Asp His Met Lys Gln His Asp Phe Phe Lys Ser Ala Met Pro Glu
465                 470                 475                 480

Gly Tyr Val Gln Glu Arg Thr Ile Phe Phe Lys Asp Asp Gly Asn Tyr
                485                 490                 495

Lys Thr Arg Ala Glu Val Lys Phe Glu Gly Asp Thr Leu Val Asn Arg
                500                 505                 510

Ile Glu Leu Lys Gly Ile Asp Phe Lys Glu Asp Gly Asn Ile Leu Gly
                515                 520                 525

His Lys Leu Glu Tyr Asn Gly Thr Ile Val Leu Glu Gly Thr Arg Ser
            530                 535                 540

Glu Gln Gln Pro Leu Thr Leu Thr Ala Ala Thr Thr Arg Ala Gln Glu
545                 550                 555                 560

Leu Arg Lys Gln Leu Asn Gln Tyr Ser His Glu Tyr Tyr Val Lys Asp
                565                 570                 575

Gln Pro Ser Val Glu Asp Tyr Val Tyr Asp Arg Leu Tyr Lys Glu Leu
            580                 585                 590

Val Asp Ile Glu Thr Glu Phe Pro Asp Leu Ile Thr Pro Asp Ser Pro
                595                 600                 605

Thr Gln Arg Val Gly
            610

<210> SEQ ID NO 10
<211> LENGTH: 614
<212> TYPE: PRT
<213> ORGANISM: Artificial Sequence
<220> FEATURE:
<223> OTHER INFORMATION: NAD+ Biosensor

<400> SEQUENCE: 10

Met Asp Tyr Lys Asp Asp Asp Lys Leu Asp Gly Gly Tyr Pro Tyr
1               5                   10                  15

Asp Val Pro Asp Tyr Ala Ala Arg Gly Tyr Gln Thr Ser Leu Tyr Lys
                20                  25                  30

Lys Ala Gly Ser Thr Met Gly His Met Glu Lys Ala Pro His Asp Ile
            35                  40                  45

Pro Met Tyr Ser Leu Asn Asp Gly Phe Ser Lys Glu Asp Ile Phe Ala
            50                  55                  60

Phe Asp Glu Arg Val Arg Lys Ala Ile Gly Lys Pro Val Ala Tyr Cys
65                  70                  75                  80

Cys Glu Leu Leu Ile Asp Gly Leu Ala Ile Ser Leu Arg Tyr Glu Asn
                85                  90                  95

Gly Val Phe Val Arg Gly Ala Thr Arg Gly Asp Gly Thr Val Gly Glu
            100                 105                 110

Asn Ile Thr Glu Asn Leu Arg Thr Val Arg Ser Val Pro Met Arg Leu
            115                 120                 125

Thr Glu Pro Ile Ser Val Glu Val Arg Gly Glu Cys Tyr Met Pro Lys
            130                 135                 140

Gln Ser Phe Val Ala Leu Asn Glu Glu Arg Glu Glu Asn Gly Gln Asp
145                 150                 155                 160

Ile Phe Ala Asn Pro Arg Asn Ala Ala Ala Gly Ser Leu Arg Gln Leu
                165                 170                 175
```

-continued

Asp Thr Lys Ile Val Ala Lys Arg Asn Leu Asn Thr Phe Leu Tyr Thr
            180                 185                 190
Val Ala Asp Phe Gly Pro Met Lys Ala Lys Thr Gln Phe Glu Ala Leu
        195                 200                 205
Glu Glu Leu Ser Ala Ile Gly Phe Arg Thr Asn Pro Glu Arg Gln Leu
    210                 215                 220
Cys Gln Ser Ile Asp Glu Val Trp Ala Tyr Ile Glu Glu Tyr His Glu
225                 230                 235                 240
Lys Arg Ser Thr Leu Pro Tyr Glu Ile Asn Gly Ile Val Ile Lys Val
                245                 250                 255
Asn Glu Phe Ala Leu Gln Asp Glu Leu Gly Phe Thr Val Lys Ala Pro
            260                 265                 270
Arg Trp Ala Ile Ala Tyr Lys Phe Pro Thr Gly Arg Gly Arg Val Tyr
        275                 280                 285
Ser Ala Gly Tyr Asn Ser Asp Asn Val Tyr Ile Thr Ala Asp Lys Gln
    290                 295                 300
Lys Asn Gly Ile Lys Ala Asn Phe Lys Ile Arg His Asn Ile Glu Asp
305                 310                 315                 320
Gly Gly Val Gln Leu Ala Asp His Tyr Gln Gln Asn Thr Pro Ile Gly
                325                 330                 335
Asp Gly Pro Val Leu Leu Pro Asp Asn His Tyr Leu Ser Phe Gln Ser
            340                 345                 350
Lys Leu Ser Lys Asp Pro Asn Glu Lys Arg Asp His Met Val Leu Leu
        355                 360                 365
Glu Phe Val Thr Ala Ala Gly Ile Thr Leu Gly Met Asp Glu Leu Tyr
    370                 375                 380
Lys Gly Gly Ser Gly Gly Met Val Ser Lys Gly Glu Glu Leu Phe Thr
385                 390                 395                 400
Gly Val Val Pro Ile Leu Val Glu Leu Asp Gly Asp Val Asn Gly His
                405                 410                 415
Lys Phe Ser Val Ser Gly Glu Gly Glu Gly Asp Ala Thr Tyr Gly Lys
            420                 425                 430
Leu Thr Leu Lys Leu Ile Cys Thr Thr Gly Lys Leu Pro Val Pro Trp
        435                 440                 445
Pro Thr Leu Val Thr Thr Leu Gly Tyr Gly Leu Gln Cys Phe Ala Arg
    450                 455                 460
Tyr Pro Asp His Met Lys Gln His Asp Phe Phe Lys Ser Ala Met Pro
465                 470                 475                 480
Glu Gly Tyr Val Gln Glu Arg Thr Ile Phe Phe Lys Asp Asp Gly Asn
                485                 490                 495
Tyr Lys Thr Arg Ala Glu Val Lys Phe Glu Gly Asp Thr Leu Val Asn
            500                 505                 510
Arg Ile Glu Leu Lys Gly Ile Asp Phe Lys Glu Asp Gly Asn Ile Leu
        515                 520                 525
Gly His Lys Leu Glu Tyr Asn Gly Thr Ile Val Leu Glu Gly Thr Arg
    530                 535                 540
Ser Glu Gln Gln Pro Leu Thr Leu Thr Ala Ala Thr Thr Arg Ala Gln
545                 550                 555                 560
Glu Leu Arg Lys Gln Leu Asn Gln Tyr Ser His Glu Tyr Tyr Val Lys
                565                 570                 575
Asp Gln Pro Ser Val Glu Asp Tyr Val Tyr Asp Arg Leu Tyr Lys Glu
            580                 585                 590

-continued

```
Leu Val Asp Ile Glu Thr Glu Phe Pro Asp Leu Ile Thr Pro Asp Ser
        595                 600                 605

Pro Thr Gln Arg Val Gly
    610

<210> SEQ ID NO 11
<211> LENGTH: 8
<212> TYPE: PRT
<213> ORGANISM: Artificial Sequence
<220> FEATURE:
<223> OTHER INFORMATION: FLAG (R) Tag

<400> SEQUENCE: 11

Asp Tyr Lys Asp Asp Asp Asp Lys
1               5

<210> SEQ ID NO 12
<211> LENGTH: 9
<212> TYPE: PRT
<213> ORGANISM: Artificial Sequence
<220> FEATURE:
<223> OTHER INFORMATION: HA tag

<400> SEQUENCE: 12

Tyr Pro Tyr Asp Val Pro Asp Tyr Ala
1               5

<210> SEQ ID NO 13
<211> LENGTH: 23
<212> TYPE: PRT
<213> ORGANISM: Artificial Sequence
<220> FEATURE:
<223> OTHER INFORMATION: Mitochondrial Localization Tag

<400> SEQUENCE: 13

Leu Ala Thr Arg Val Phe Ser Leu Val Gly Lys Arg Ala Ile Ser Thr
1               5                   10                  15

Ser Val Cys Val Arg Ala His
            20

<210> SEQ ID NO 14
<211> LENGTH: 11
<212> TYPE: PRT
<213> ORGANISM: Artificial Sequence
<220> FEATURE:
<223> OTHER INFORMATION: Nuclear Export Signal

<400> SEQUENCE: 14

Leu Gln Lys Lys Leu Glu Glu Leu Glu Leu Asp
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Nuclear Localization Signal

<400> SEQUENCE: 15

Pro Lys Lys Lys Arg Lys Val
1               5
```

BIOSENSORS THAT DETECT NAD⁺

ACKNOWLEDGEMENT OF GOVERNMENT SUPPORT

This invention was made with the support of the United States government under the terms of Grant Numbers MH094416, NS079317, and T32DK007674 awarded by the National Institutes of Health. The United States government has certain rights in this invention.

FIELD

Generally, the field involves systems and methods of detecting biomolecules. More specifically, the field involves polypeptide biosensors that can be used to detect NAD⁺

BACKGROUND

NAD⁺ (nicotinamide adenine dinucleotide) is an essential cofactor for many important NAD⁺-consuming enzymatic classes, such as sirtuins, poly ADP-ribose polymerases (PARPs), and cyclic ADP-ribose synthetases. As such, the bioavailable pools of NAD⁺ (the oxidized form of NAD) that regulate these critical enzymes represent links between metabolism, pathology, and numerous essential biological processes. The ability to monitor NAD⁺ levels in the cells is critical to understanding when, where, and how these enzymes function.

Sensors are available that can monitor NAD⁺/NADH ratios in a cell. However, NAD⁺ regulated enzymes operate in the nucleus and cytoplasm and are therefore unlikely to be regulated by redox reactions. Furthermore, NAD⁺ levels can be as much as 700-fold higher than NADH levels with concentrations in the micromolar range. Many NAD⁺ consuming enzymes have $K_m$ values in the micromolar range. Finally, current methods are unable to measure NAD⁺ concentrations in subcellular compartments and organelles. So directly monitoring NAD⁺ is key to understanding the function of NAD regulated enzymes.

Measurement of NAD⁺ using methods such as HPLC and mass spectrometry require harvesting and processing of cells and/or tissues. Using such methods, there is no way to differentiate the bioavailable pool of NAD⁺ from the protein-bound pool of NAD⁺ and certainly no way to measure intracellular localization of free NAD⁺ or changes in NAD⁺ levels over time.

SUMMARY

Disclosed herein is an NAD⁺ biosensor polypeptide, an expression vector encoding the polypeptide, and methods of detecting NAD⁺ using the biosensor polypeptide.

The biosensor polypeptide includes a first NAD⁺ dependent DNA ligase adenylation domain fragment from the N-terminal portion of the DNA ligase adenylation domain. It also includes a second NAD⁺ dependent DNA ligase adenylation domain fragment from the C-terminal portion of the DNA ligase adenylation domain. It also includes a fluorescent protein. These elements are positioned such that the fluorescent protein is between the first fragment and the second fragment. In some examples, the second fragment is positioned toward the N-terminus of the polypeptide and the first fragment is positioned towards the C-terminus. The polypeptide can further include a first linker, such as a first linker positioned between the fluorescent protein and the first fragment. A polypeptide with a first linker can also include a second linker, such as a second linker positioned between the second fragment and the N-terminus. In still further examples, the fluorescent protein is a circularly permutated fluorescent protein such as cpVenus. In still further examples, the polypeptide includes: a FLAG® tag, an HA tag, a nuclear export signal, a nuclear localization signal, and/or a mitochondrial localization signal. Also disclosed are expression vectors comprising nucleic acids that encode the disclosed biosensor polypeptides.

Also disclosed are methods of detecting NAD⁺ in a sample. The methods involve contacting the sample with the disclosed polypeptides, measuring fluorescent emission at a first excitation wavelength, and measuring fluorescent emission at a second excitation wavelength. A greater emission at the second excitation wavelength relative to the first excitation wavelength is indicative of the presence of NAD⁺ in the sample. Also disclosed are methods of detecting NAD⁺ in samples comprising active cells including in subcellular compartments.

It is an object of the invention to provide a system that directly monitors and measures bioavailable NAD⁺ levels in cells and organelles in both healthy and disease-related conditions.

It is an object of the invention to measure free NAD⁺ in cells with temporal and/or spatial resolution of NAD⁺.

BRIEF DESCRIPTION OF THE SEVERAL VIEWS OF THE DRAWINGS

Some of the drawings herein are better understood when presented in color, which is not available in patent application publications. However, Applicants consider the color drawings to be part of the original disclosure and reserve the right to present color versions of the drawings herein in later proceedings.

Then the buffer was exchanged, washing out the NAD$^+$. Post buffer exchange, the excitation and emission spectra were equivalent.

Figure 1A:
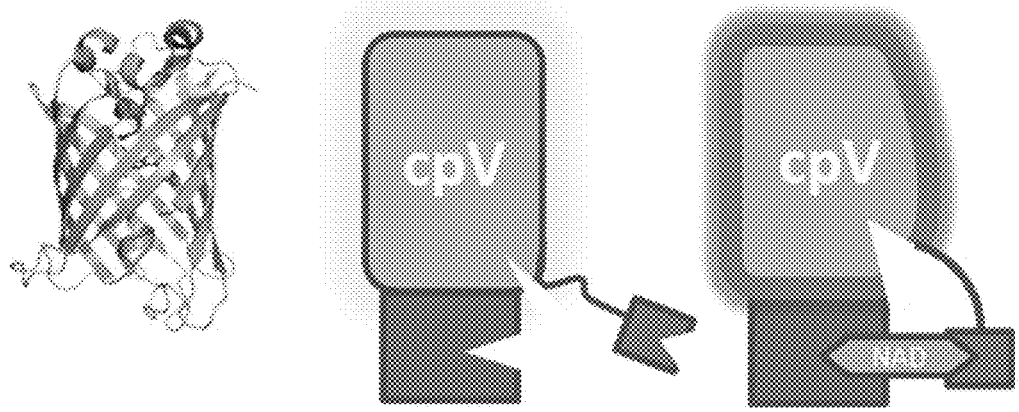
FIG. 1A is a set of three drawings depicting (left) a ribbon structure of cpVenus, (center) a cartoon version of the biosensor without a linker between the second fragment and the linker without NAD⁺ bound, and (right) a cartoon version of the same biosensor with NAD⁺ bound. Biosensors of the type depicted are exemplified herein by SEQ ID NO: 6, SEQ ID NO: 7, SEQ ID NO: 8, and SEQ ID NO: 9.
Figure 1B:
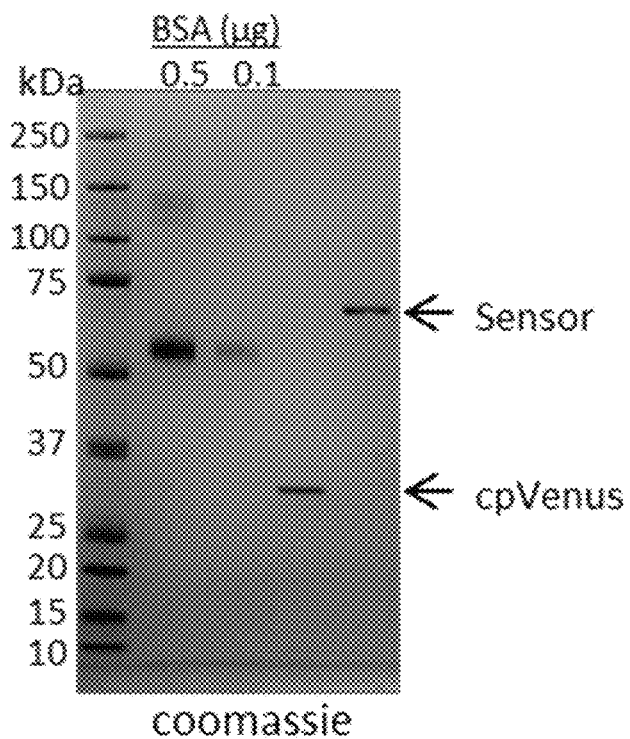
FIG. 1B depicts an image of a Coomassie gel of purified cpVenus and the biosensor depicted in FIG. 1A as indicated.
Figure 1C:
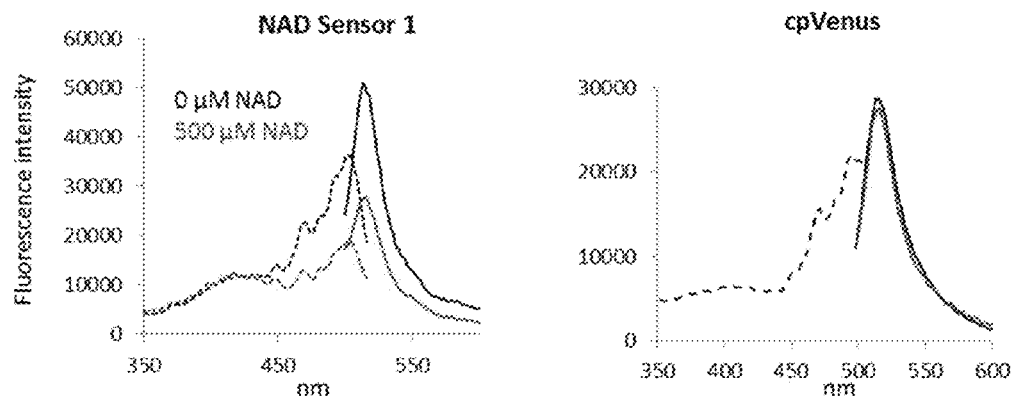
FIG. 1C is a set of two plots showing the excitation and emission profiles of (left) the sensor depicted in FIG. 1A and (right) cpVenus in the presence (red) and absence (black) of NAD⁺.
Figure 2A:
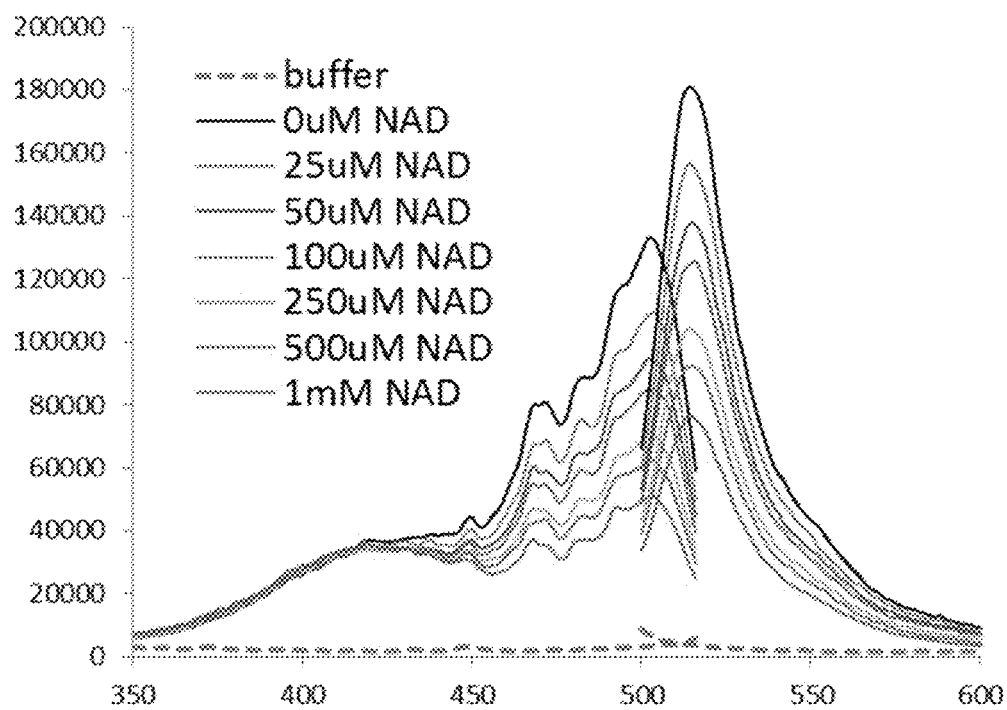
FIG. 2A is a plot showing that the excitation and emission profile of the biosensor is sensitive to the concentration of NAD⁺
Figure 2B:
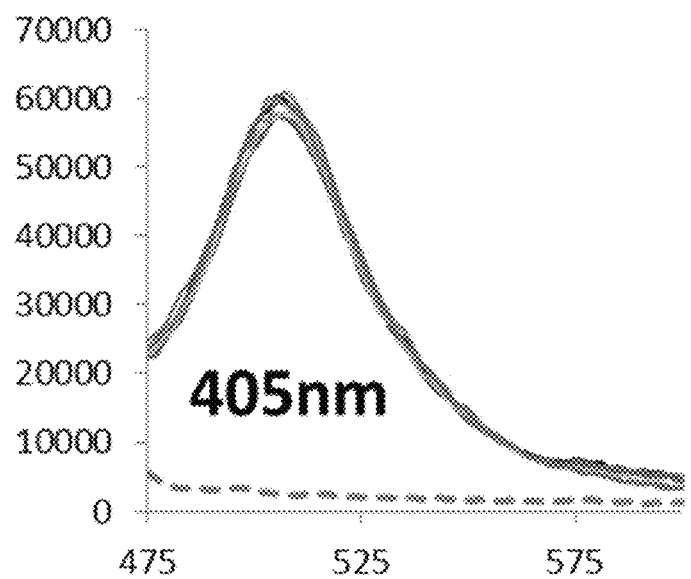
FIG. 2B is a plot showing that the emission profile of the biosensor, when excited at 405 nm, is unaffected by NAD⁺ concentration.
Figure 2C:
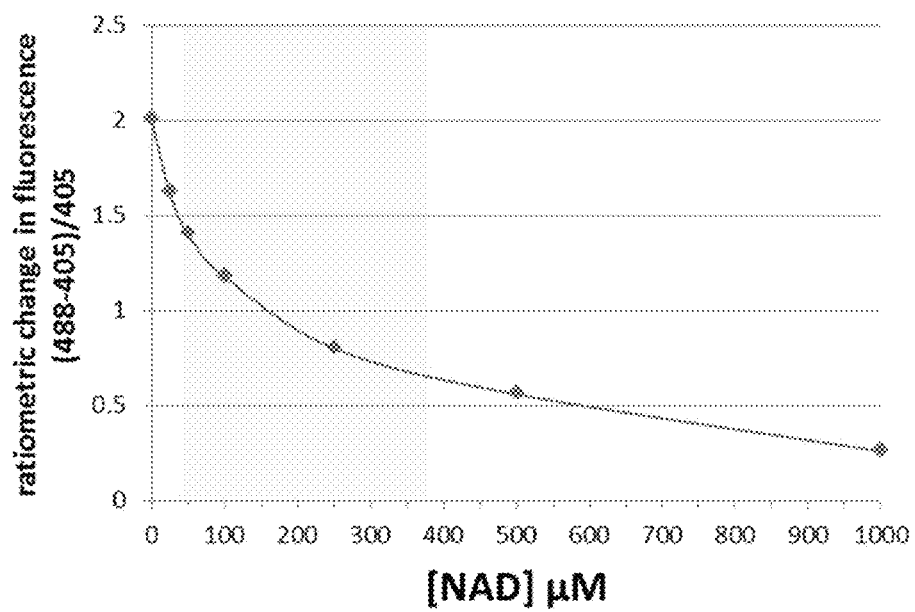
FIG. 2C is a plot derived from data similar to that in FIG. 2A showing the ratiometric change in fluorescence of the biosensor as a function of NAD⁺ concentration. Shaded area is the physiological range of NAD⁺. This is an example of a standard curve.
Figure 3A:
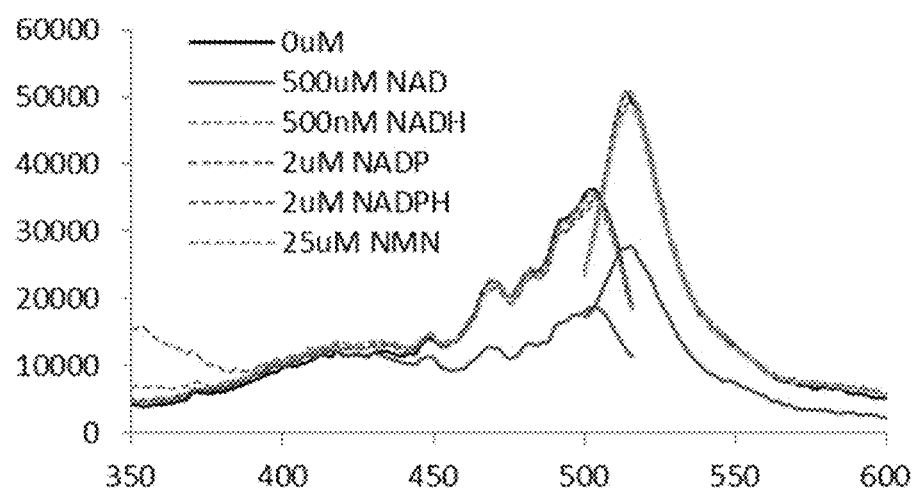
FIG. 3A is a plot showing that the biosensor is specific for NAD⁺ and does not detect the other indicated compounds at the indicated concentrations.
Figure 3B:
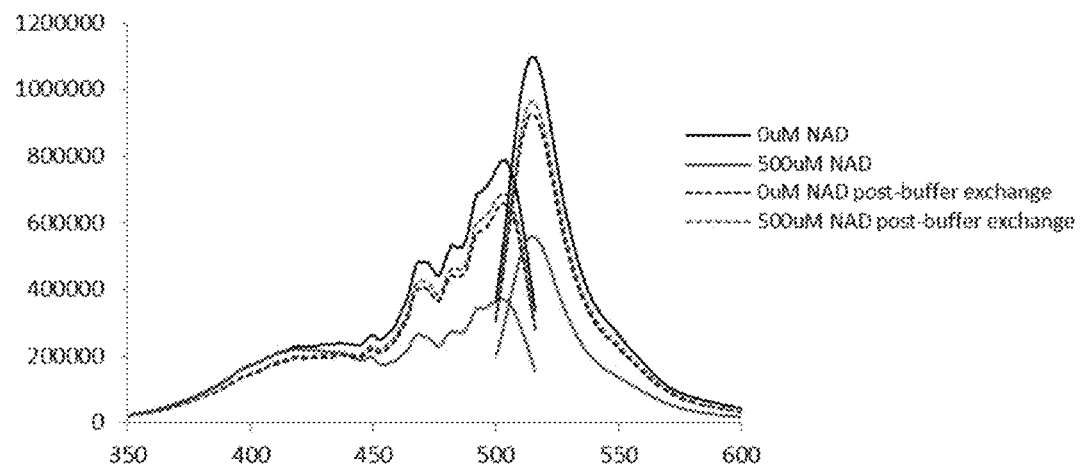
FIG. 3B is a plot showing that the detection of NAD⁺ by the biosensor is reversible. 500 μM NAD⁺ was detected relative to a negative control as shown in the above figures.
Figure 3C:
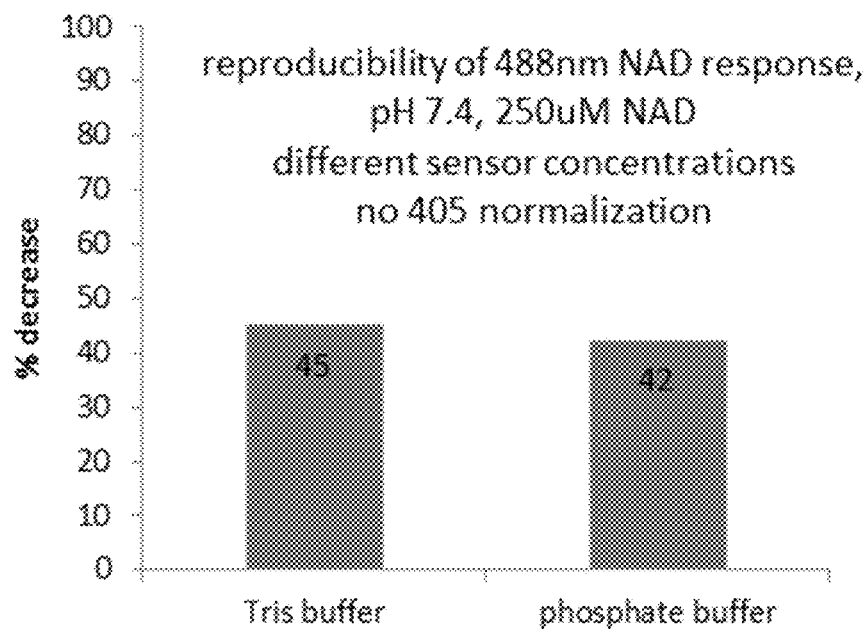

FIG. 3C is a bar graph showing that the detection of NAD$^+$ response using the biosensor is reproducible across sensor concentrations and across buffer type.

Figure 4A:
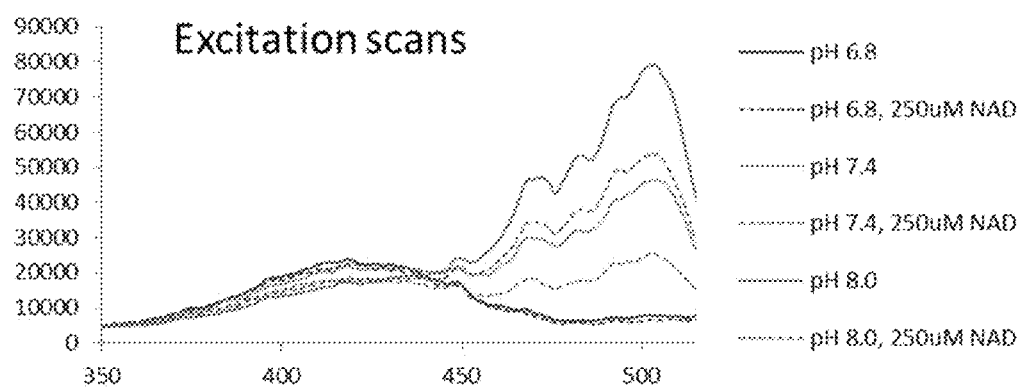

FIG. 4A is a plot of an excitation scan of the biosensor at the indicated NAD$^+$ concentrations and pH levels.

Figure 4B:
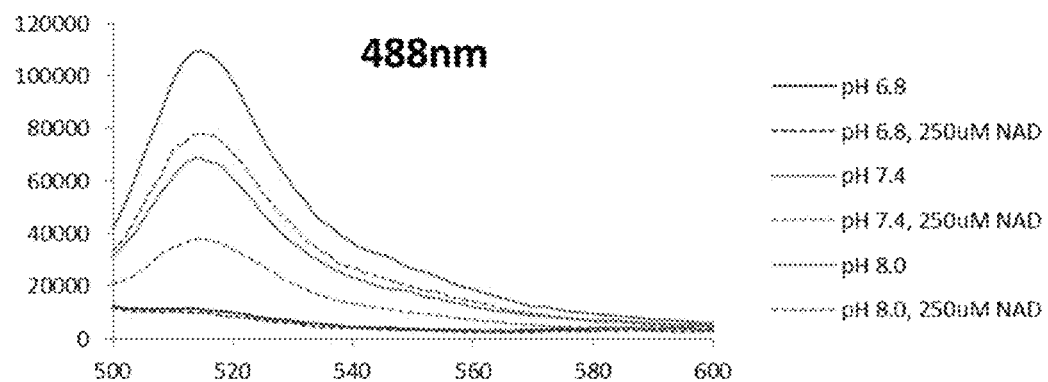

FIG. 4B shows the emission at 488 nm of the biosensor under the indicated conditions.

Figure 4C:
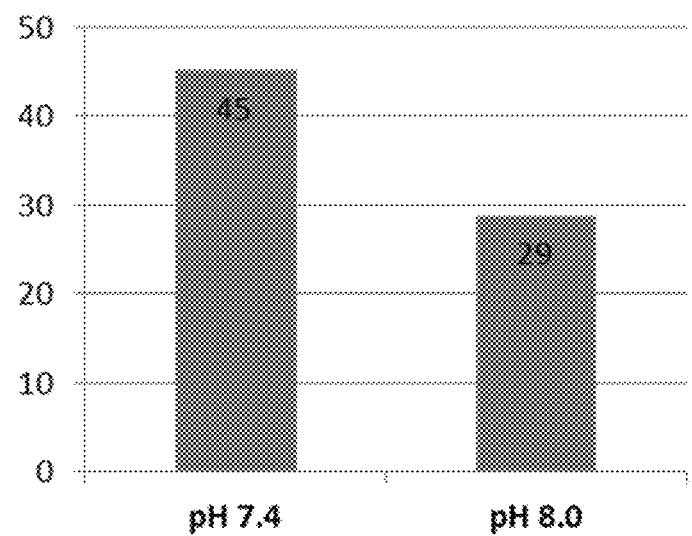

FIG. 4C is a bar graph of the percentage difference in 488 nm fluorescence in the biosensor in the presence of 250 µM NAD$^+$ relative to a negative control at the indicated pH.

Figure 5A:
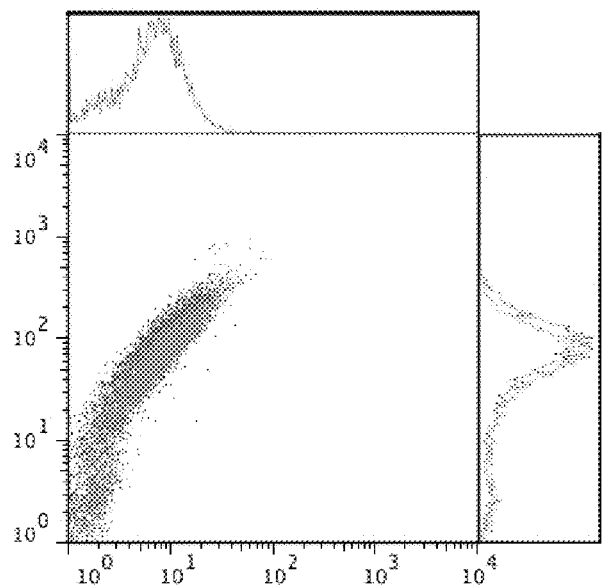

FIG. 5A is a flow cytometry plot of HEK 293T cells stably expressing the biosensor. Those expressing the sensor were untreated (blue) or treated with 10 nM FK866 (red) for 18 hours. FK866 is known to deplete cellular NAD$^+$ (Hasmann M et al, *Cancer Res* 63, 7436-7442 (2003); incorporated by reference herein). Cells were then analyzed using flow cytometry (10,000 cells per condition.) The top histogram depicts fluorescence at 525/50 following excitation at 405 nm while the right histogram depicts fluorescence at 530/30 following excitation at 488 nm.

Figure 5B:
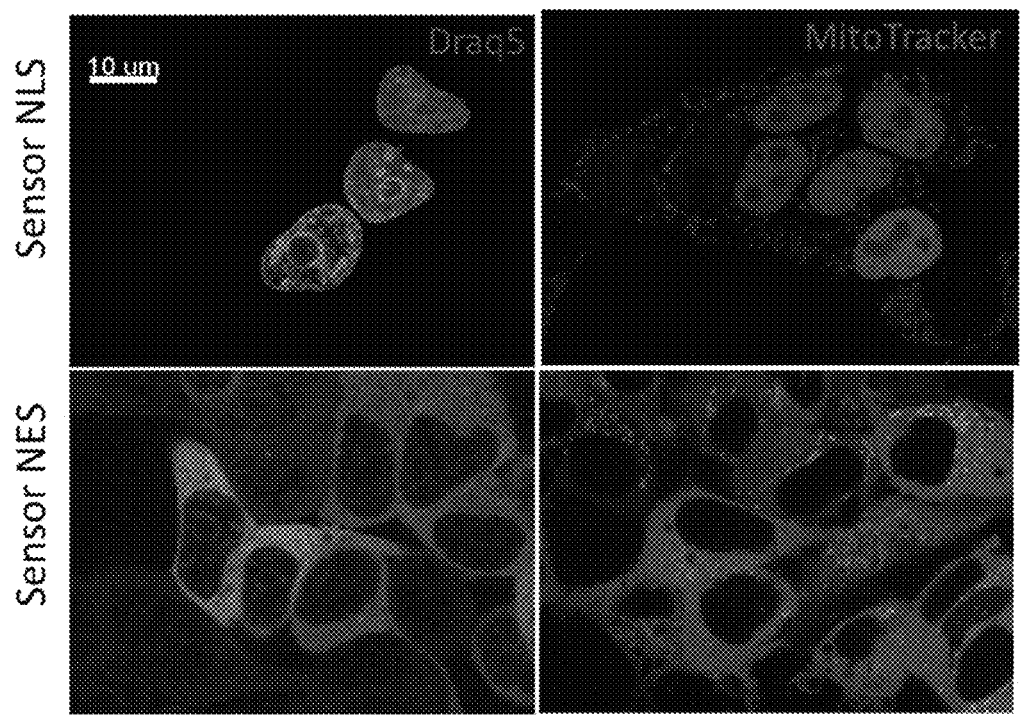

FIG. 5B is a fluorescence microscope image of HEK293T cells stably expressing the sensor with either an NLS tag (top panels) or a NES tag (bottom panels.) Draq5 was used to stain nuclei. MitoTracker was used to stain mitochondria.

Figure 6A:
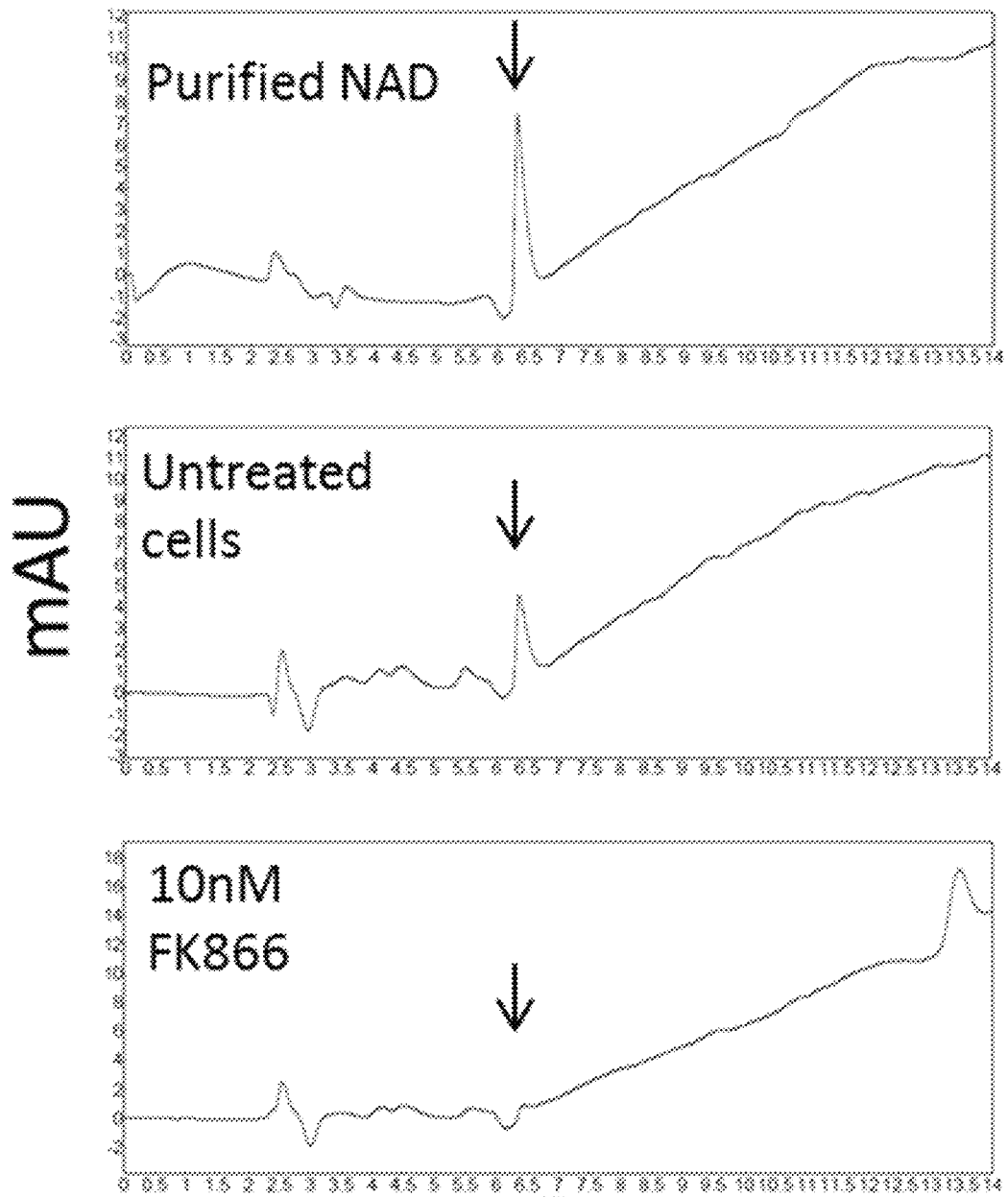

FIG. 6A is a set of three HPLC spectra from 10 µM purified NAD$^+$ standard compared to perchlorate extracted NAD$^+$ from HEK293T cells treated with 0 nM (middle) or 10 nM (bottom) FK866 for 16 hours. Note that NAD$^+$ is recovered from untreated cells while it is depleted in FK866 treated cells.

Figure 6B:
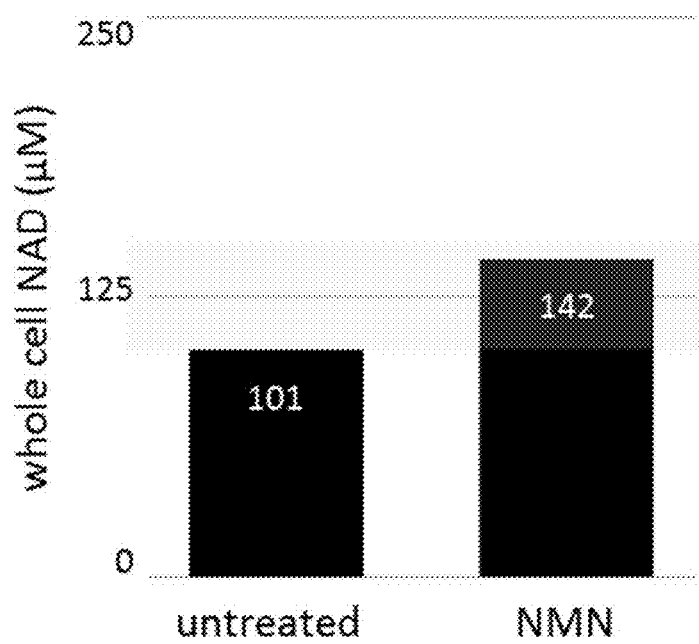

FIG. 6B is a bar graph showing the calculated molarity using HPLC data of total NAD$^+$ from HEK293T cells after treatment with 1 mM of the NAD$^+$ precursor NMN in culture for 24 hours. The Km range for the Sirt1 enzyme is indicated in yellow.

Figure 7A:
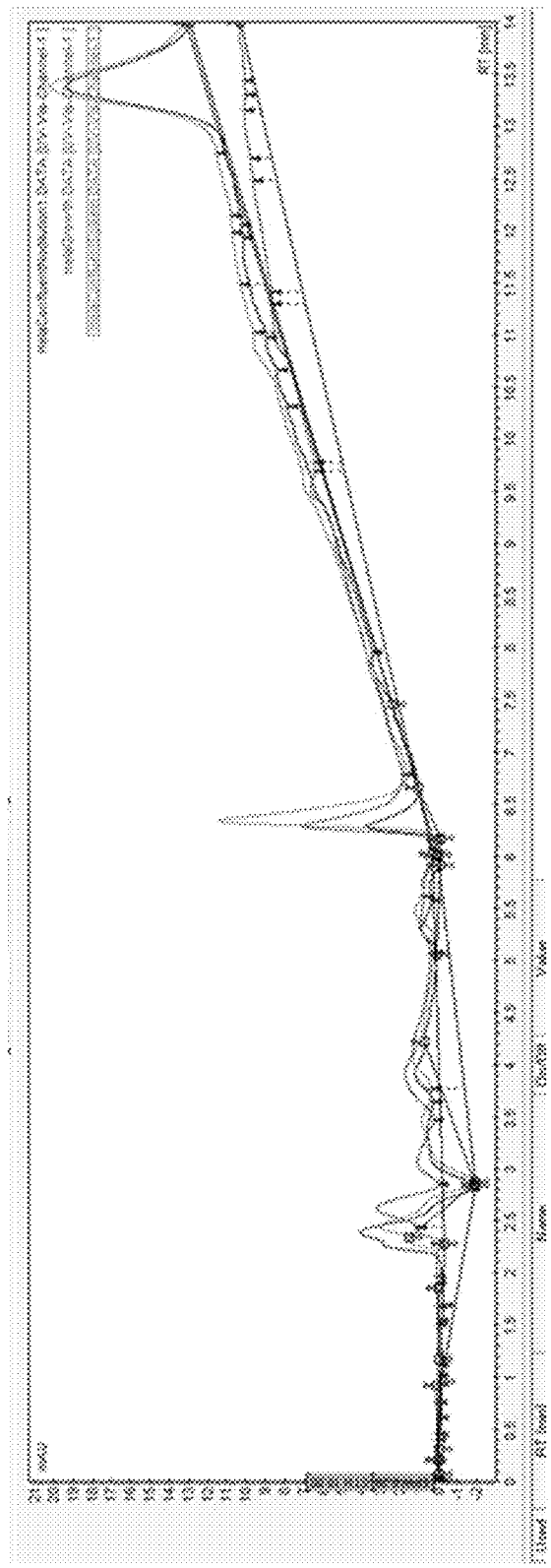

FIG. 7A is an HPLC spectra for NAD$^+$ extracted from HeLa cells. NAD$^+$ levels are lower in HeLa cells that are confluent (blue) compared to HeLa cells that remained growing (green). A NAD$^+$ standard (gray) was included to identify the NAD$^+$ peak.

Figure 7B:
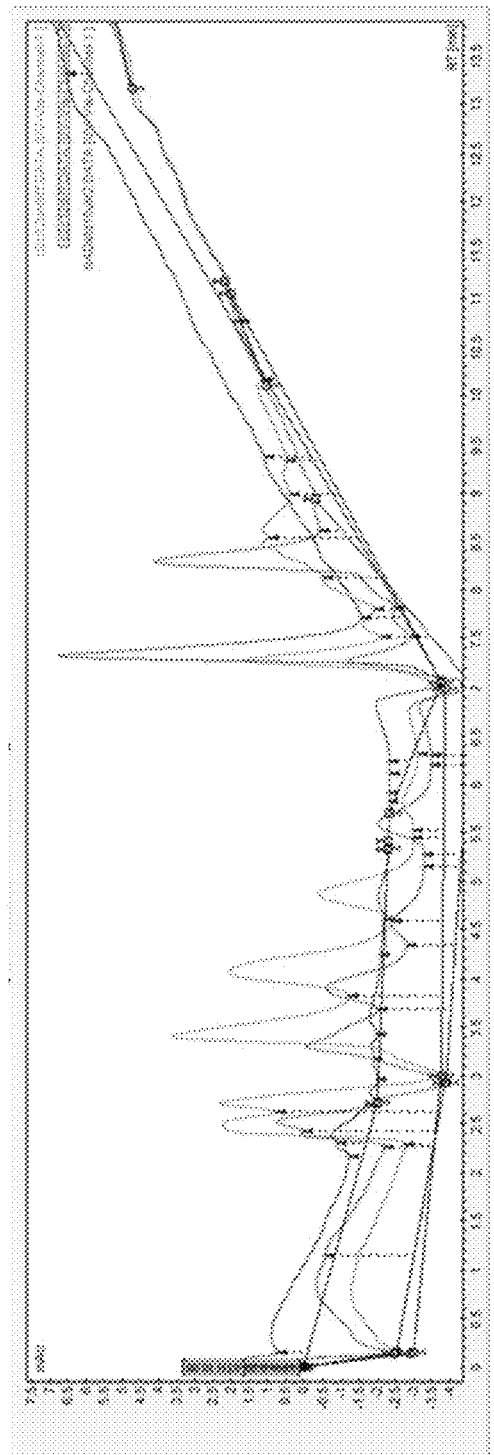

FIG. 7B is a set of HPLC spectra for NAD$^+$ extracted from C2C12 myoblast cells. NAD$^+$ levels were lower in C2C12 cells that underwent differentiation (pink) compared to C2C12 cells that remained undifferentiated (blue). A 10 µM NAD$^+$ standard (green) was included to identify the NAD$^+$ peak.

Figure 8A:
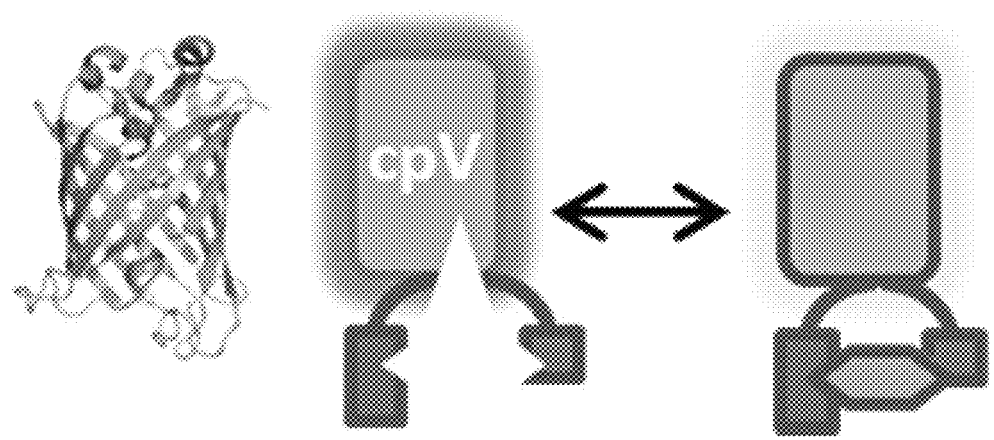

FIG. 8A is a set of three drawings depicting (left) a ribbon structure of cpVenus, (center) a cartoon version of the biosensor with two linkers without NAD$^+$ bound, and (right) a cartoon version of the same biosensor with NAD$^+$ bound. Biosensors of the type depicted are in FIG. 8A are exemplified herein by SEQ ID NO: 10.

Figure 8B:
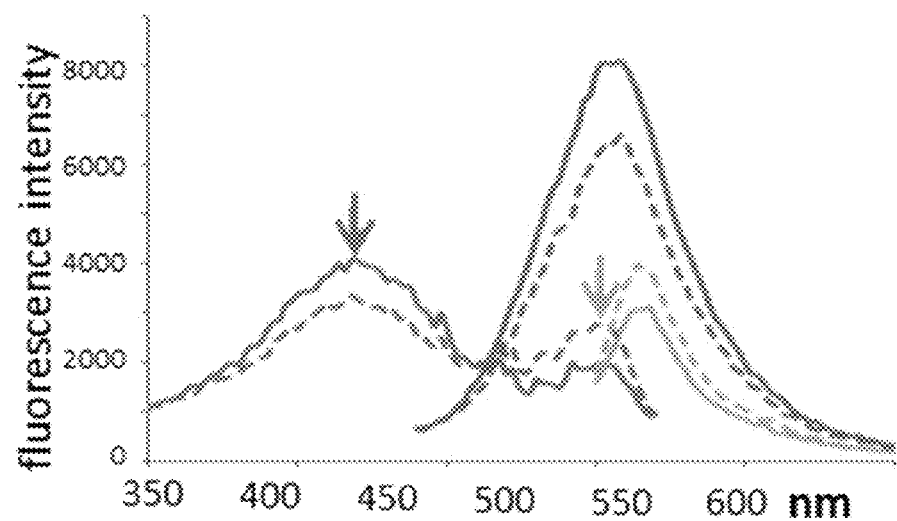

FIG. 8B is a plot of the excitation and emission spectra of the biosensor depicted in FIG. 8A with 0 µM NAD$^+$ (solid lines) and 500 µM NAD$^+$ (dashed lines). Emission spectra from 415 nm excitation are depicted in blue, those from 490 nm excitation are depicted in green.

Figure 9A:
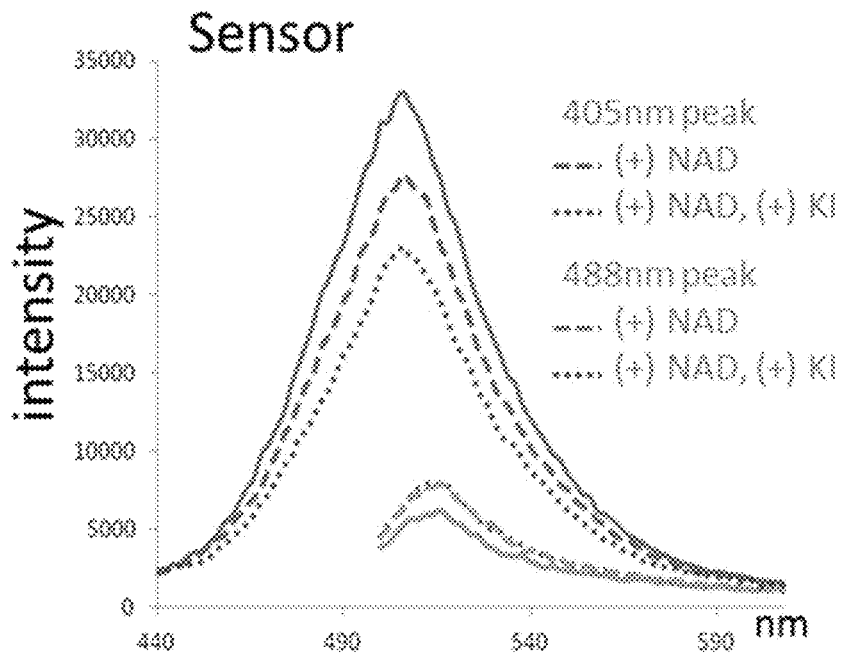

FIG. 9A is a plot showing the effect of 100 mM KI (potassium iodide) on sensor fluorescence after treatment with 500 µM NAD$^+$.

Figure 9B:
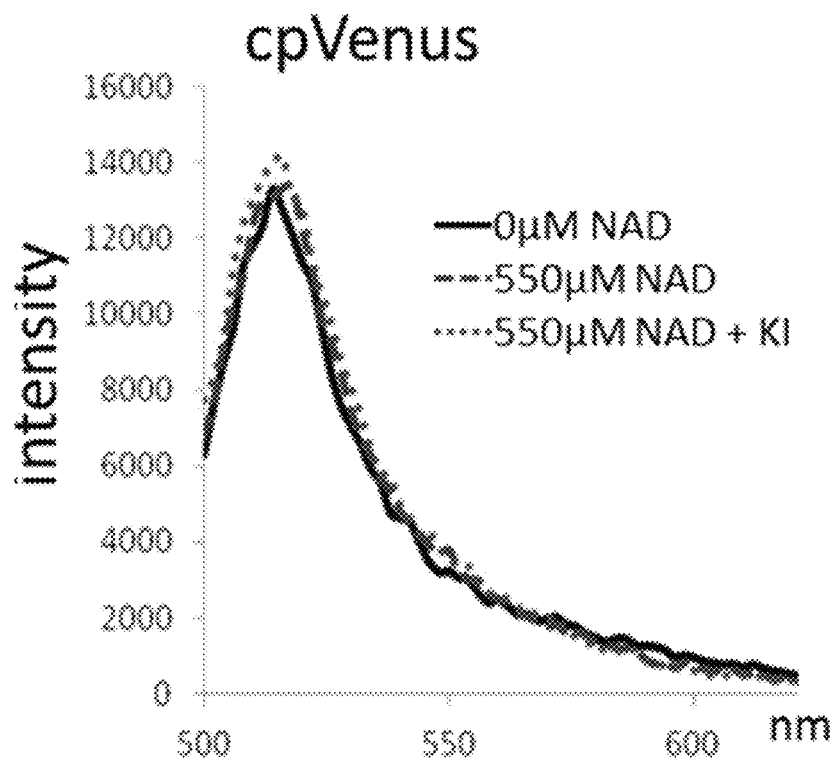

FIG. 9B is a plot showing no effect of KI on cpVenus.

Figure 10A:
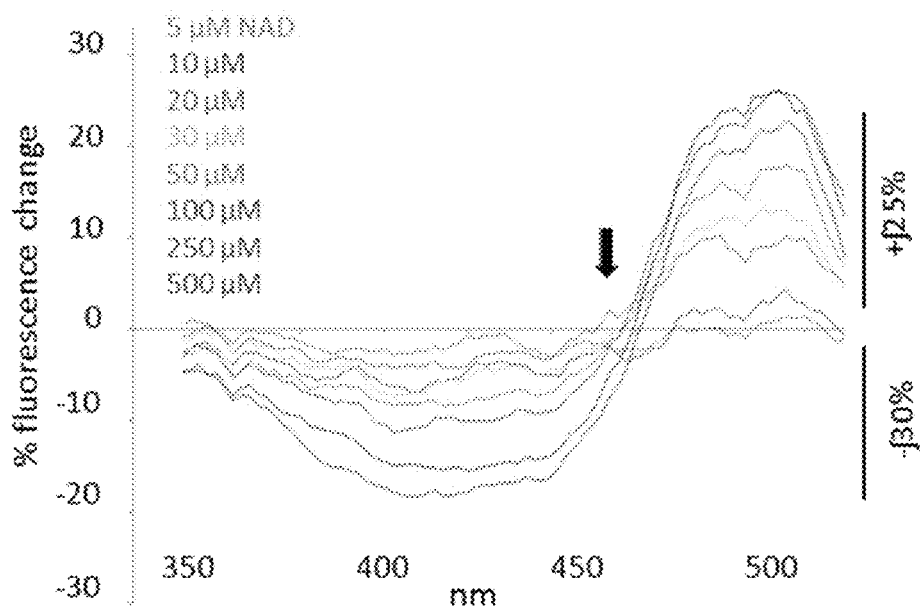

FIG. 10A is a plot showing the excitation spectrum of the biosensor shown in FIG. 8A at the indicated NAD$^+$ concentration. The arrow indicates the isosbestic point (~460 nm).

Figure 10B:
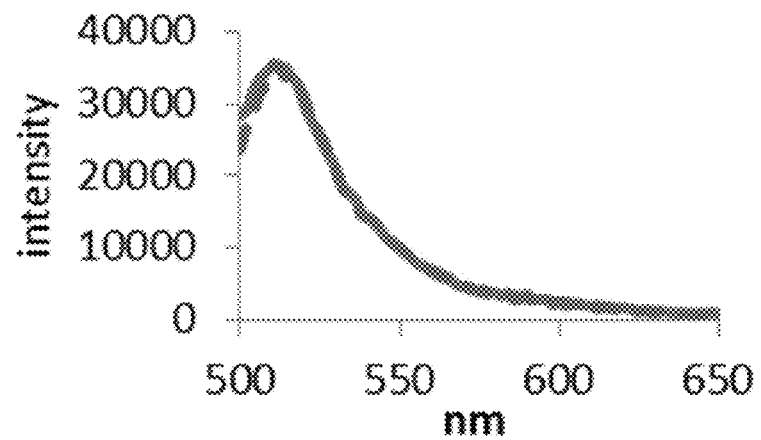

FIG. 10B is a plot showing the fluorescence of the biosensor shown in FIG. 8A at its isosbestic point (460 nm) in the presence (red) and absence (blue) of NAD$^+$.

Figure 10C:
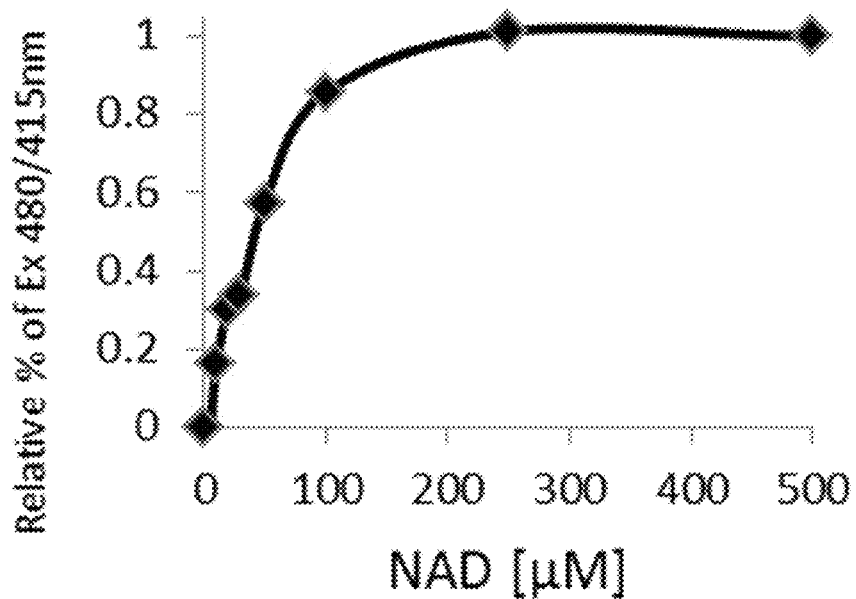

FIG. 10C is a curve showing the ratiometric measurement of 480 nm/415 nm fluorescence normalized to total percent change as a function of NAD$^+$ concentration.

Figure 11A:
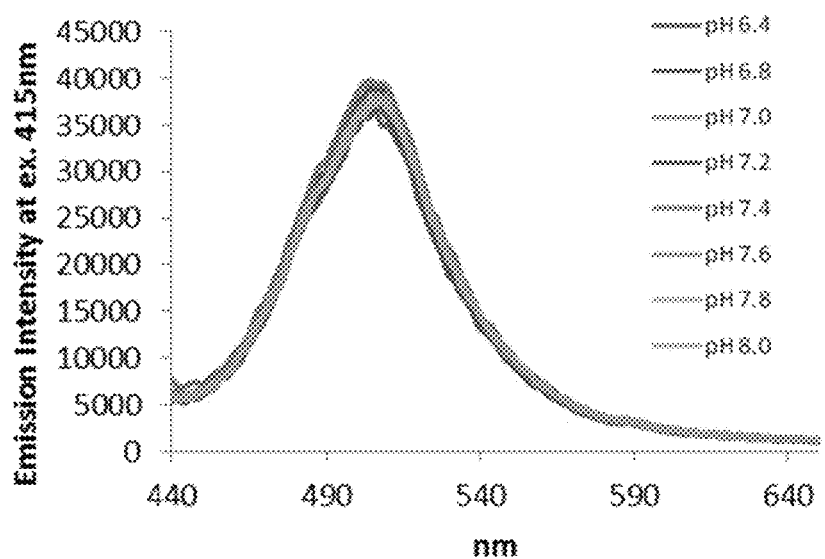

FIG. 11A is a plot showing the effect of the indicated pH on sensor fluorescence when excited at 415 nm in the absence of NAD$^+$.

Figure 11B:
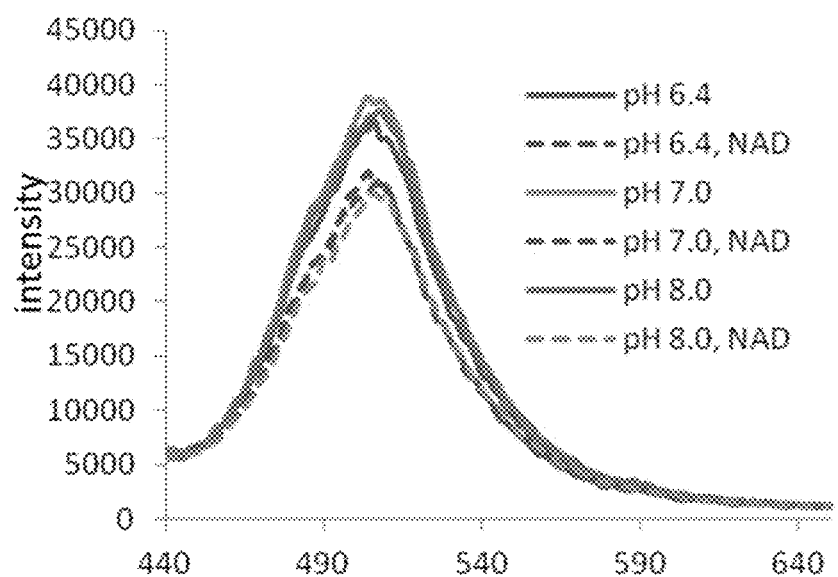

FIG. 11B is a plot showing the effect of the indicated pH on sensor fluorescence when excited at 415 nm in the presence or absence of 500 µM NAD$^+$ as indicated.

Figure 11C:
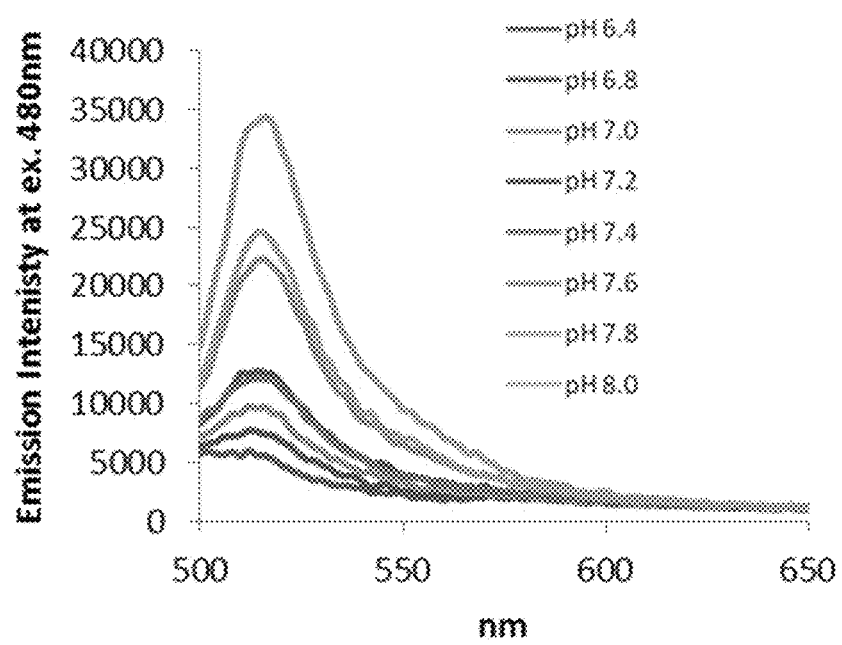
Figure 11D:
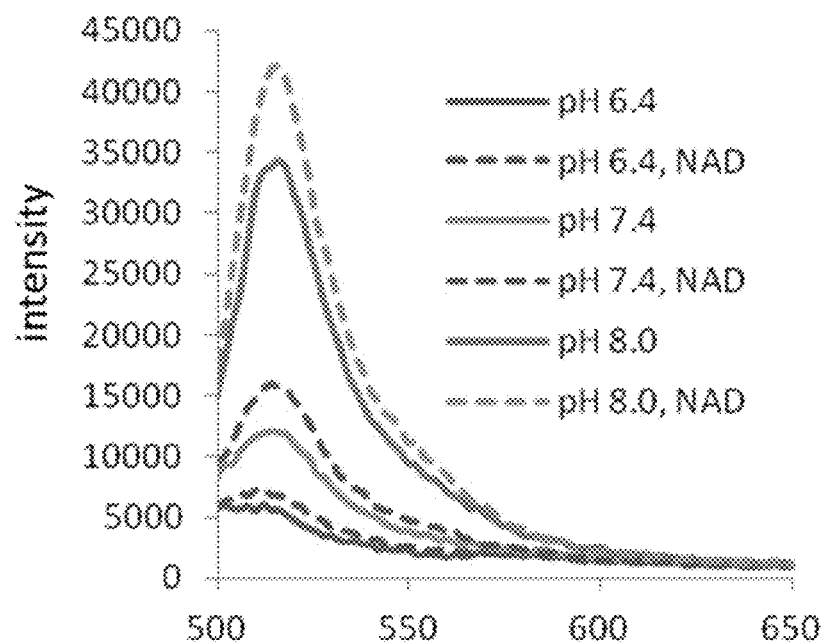

FIG. 11C is a plot showing the effect of the indicated pH on sensor fluorescence when excited at 490 nm in the absence of NAD$^+$ FIG. 11D is a plot showing the effect of the indicated pH on sensor fluorescence when excited at 490 nm at the indicated pH in the presence or absence of 500 µM NAD$^+$ as indicated.

Figure 11E:
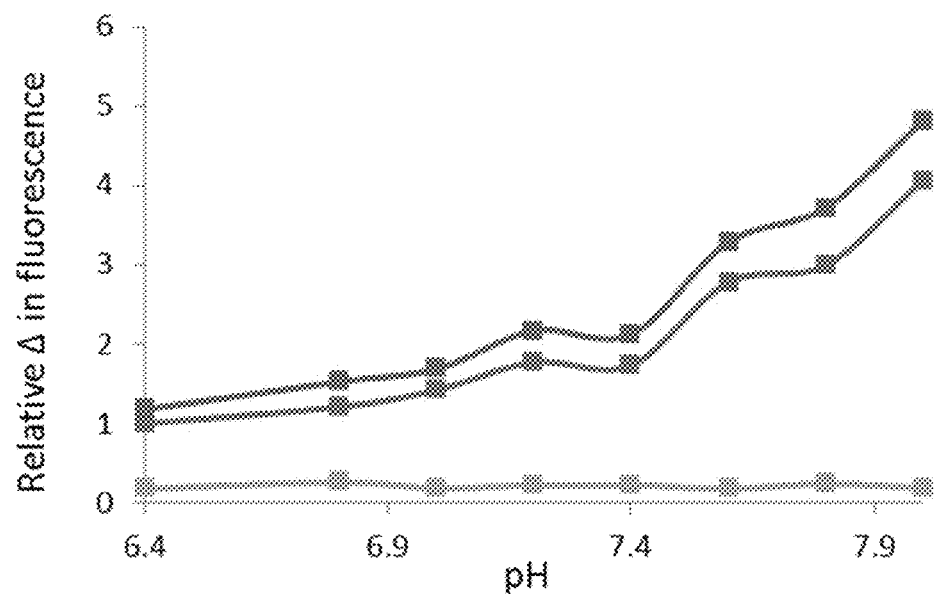

FIG. 11E is a plot showing that although the absolute intensity of fluorescence at 490 nm excitation correlates with increased pH with both 500 µM NAD$^+$ (red) and 0 µM NAD$^+$ (blue), the difference in fluorescence due to NAD$^+$ is unchanged across pH (green).

Figure 12A:
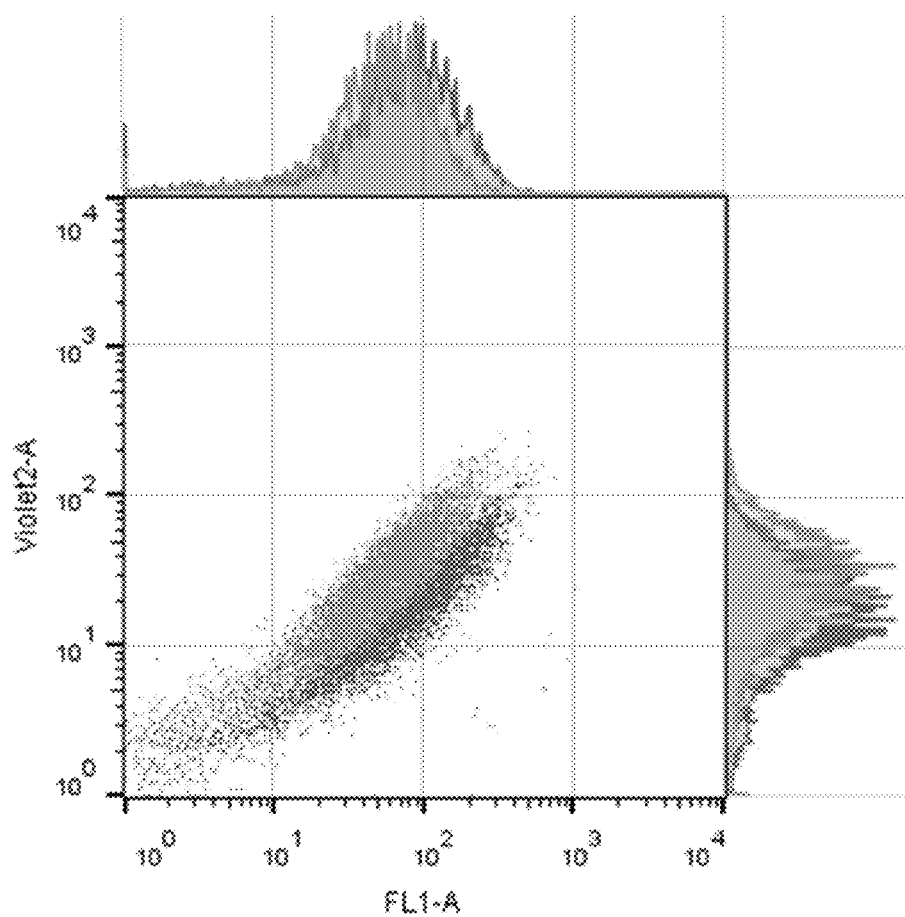

FIG. 12A is a plot of HEK 293T cells stably expressing the biosensor shown in FIG. 8A either untreated (red) or treated (blue) with 20 nM FK866 for 20 hours. These were analyzed using flow cytometry (10,000 cells/condition.) The histograms depict fluorescence at 525/50 or 530/30 when the cells are excited at 405 nm or 488 nm respectively.

Figure 12B:
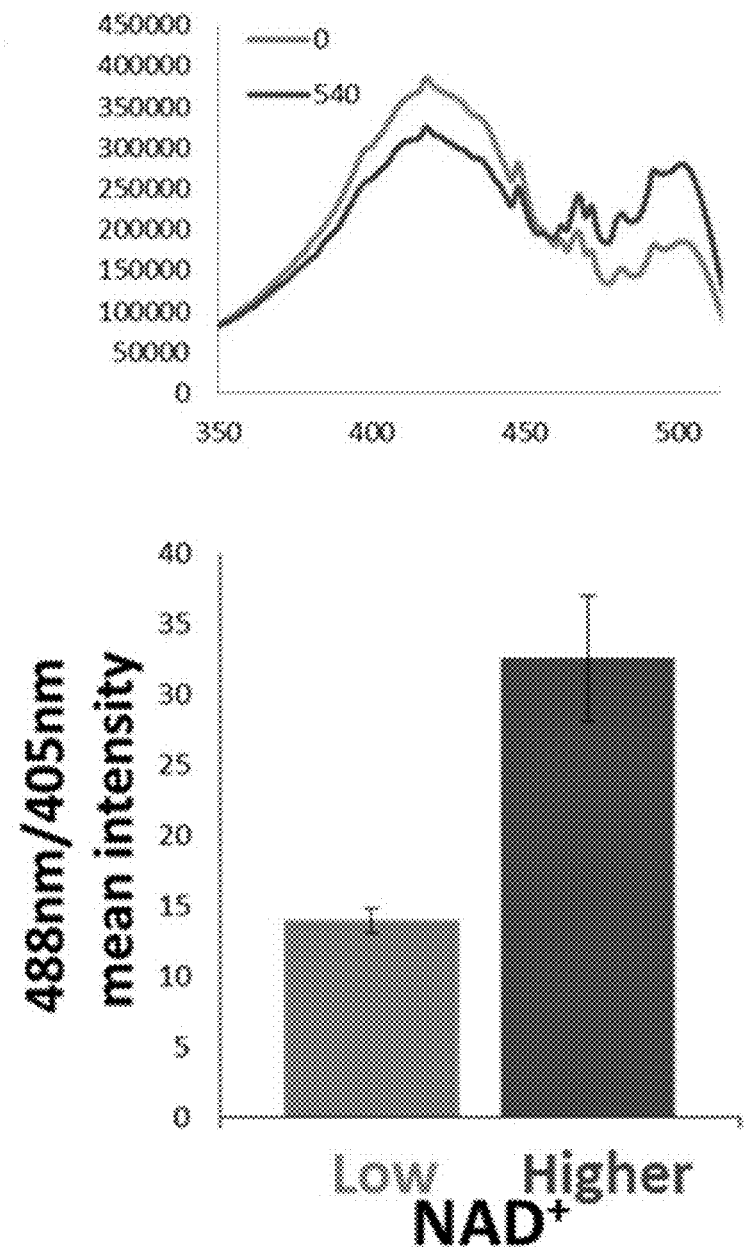

FIG. 12B is a plot (top) and bar graph (bottom) showing the excitation spectra derived from a cell free system with (red) and without (blue) 540 µM NAD$^+$. The bar graph is of ratios of mean fluorescence intensities.

Figure 13A:

FIG. 13A is a graphical illustration of the biosensor of SEQ ID NO: 6.

Figure 13B:

FIG. 13B is a graphical illustration of the biosensor of SEQ ID NO: 7.

Figure 13C:

FIG. 13C is a graphical illustration of the biosensor of SEQ ID NO: 8.

Figure 13D:

FIG. 13D is a graphical illustration of the biosensor of SEQ ID NO: 9.

Figure 13E:

FIG. 13E is a graphical illustration of the biosensor of SEQ ID NO: 10.

Figure 14A:
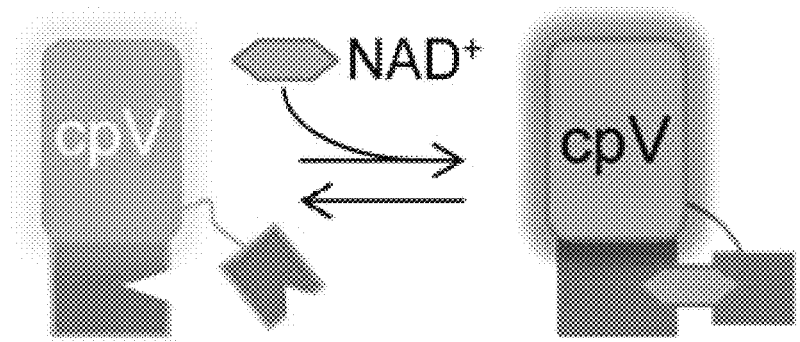

FIG. 14A is a schematic of The NAD+ biosensor comprises cpVenus (cpV) and two NAD+-binding domain fragments. The unbound species fluoresces following excitation at 488 nm. NAD+ binding to the sensor results in a loss of fluorescence.

Figure 14B:
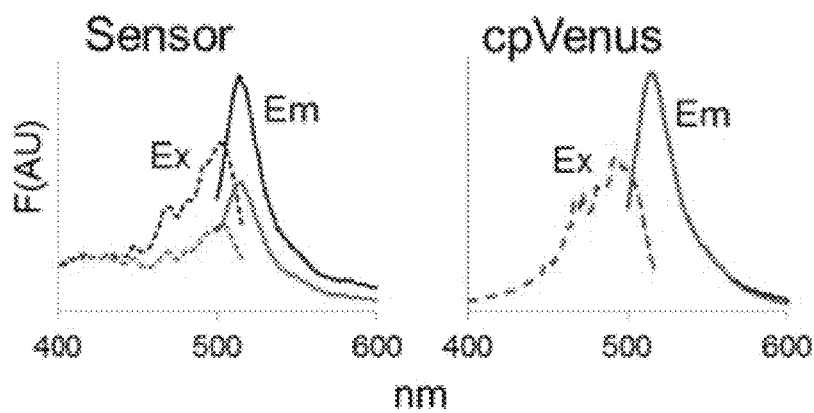

FIG. 14B is set of two plots showing excitation (dashed lines) and emission (solid lines) scans of the sensor with either 0 µM (black) or 500 µM (red) NAD+ in a cell free system. Excitation was monitored at 530 nm and emission was monitored after excitation at 488 nm.

Figure 14C:
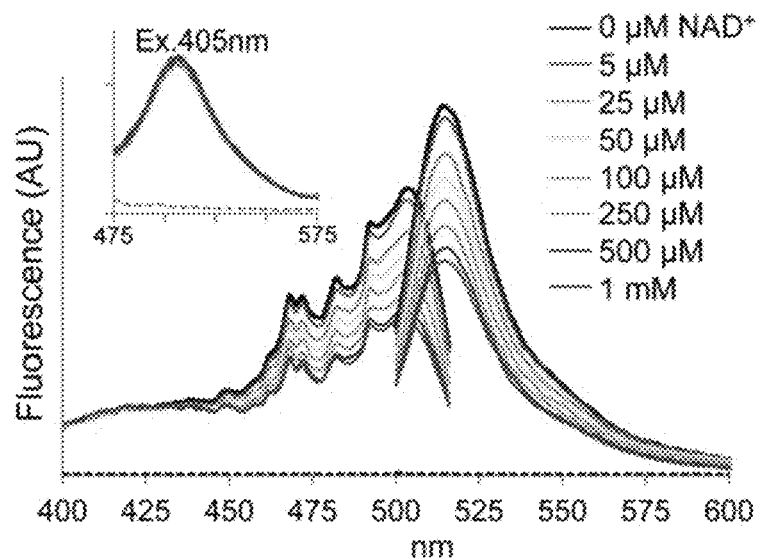

FIG. 14C is a plot (with inset) showing fluorescence emission and excitation scans at the indicated NAD+ concentrations or buffer only control (dashed lines). The inset shows fluorescence from excitation at 405 nm.

Figure 14D:
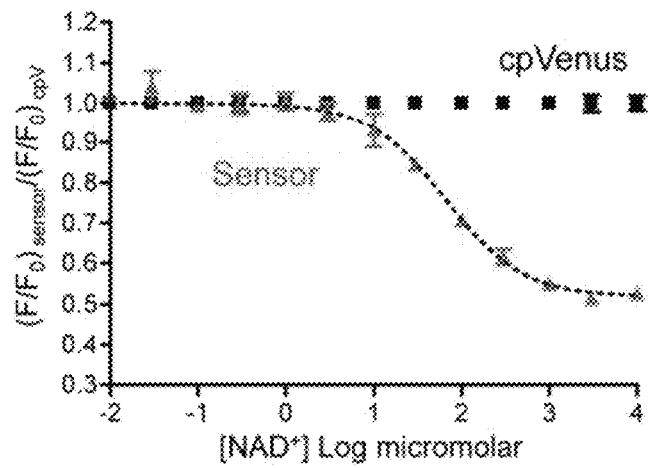

FIG. 14D is a plot showing maxima from 488 nm emission peaks of sensor and cpVenus (250 nM) at the indicated NAD+ concentrations; mean±SD, n=3.

Figure 14E:
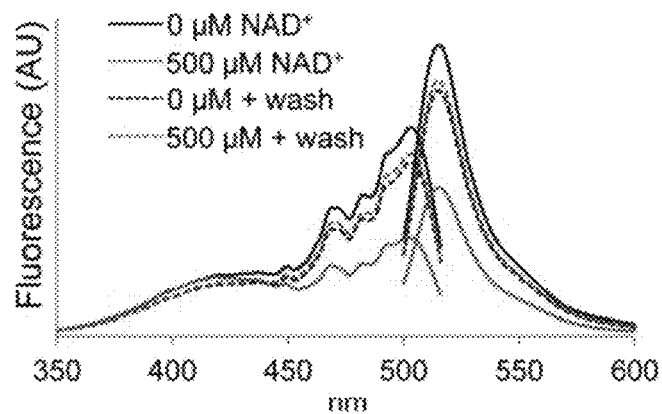

FIG. 14E is a plot showing fluorescence excitation and emission of sensor incubated with 0 µM (black solid) or 500 µM NAD+ (red solid). NAD+ was washed out and fluorescence was re-evaluated in each sample (dotted lines).

Figure 14F:
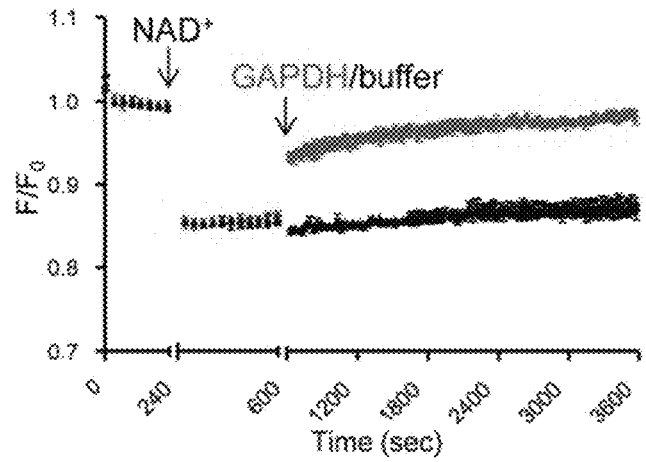

FIG. 14F is a plot showing that GAPDH (red) increases sensor fluorescence monitored at 520 nm following excitation at 488 nm.

Figure 14G:
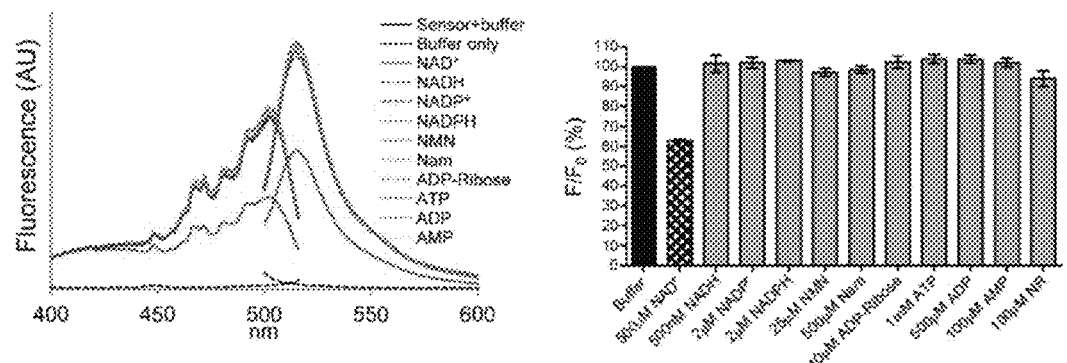

FIG. 14G is a plot and bar graph showing (left) Excitation and emission profiles and (right) maxima from 488 nm emission with the indicated substrates. mean±SD, n=3.

Figure 15A:
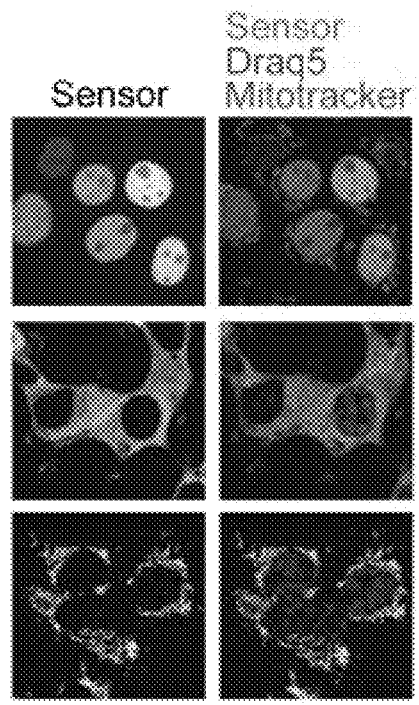

FIG. 15A is a set of six images showing HEK293T cells stably expressing nuclear, cytoplasmic, or mitochondrial sensors. Nuclear marker Draq5 (blue), mitochondrial marker Mitotracker CMXRos (red), sensor (green).

Figure 15B:
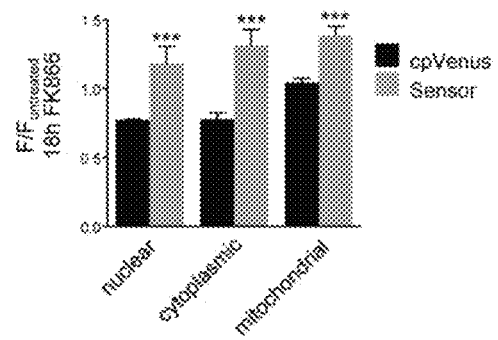

FIG. 15B is a bar graph showing the ratio of 488/405 nm fluorescence measured with flow cytometry from clonal populations following treatment with 10 nM FK866 for 18 hours. Mean±SD, n=3, ANOVA, Tukey's post-test ***p<0.001.

Figure 15C:
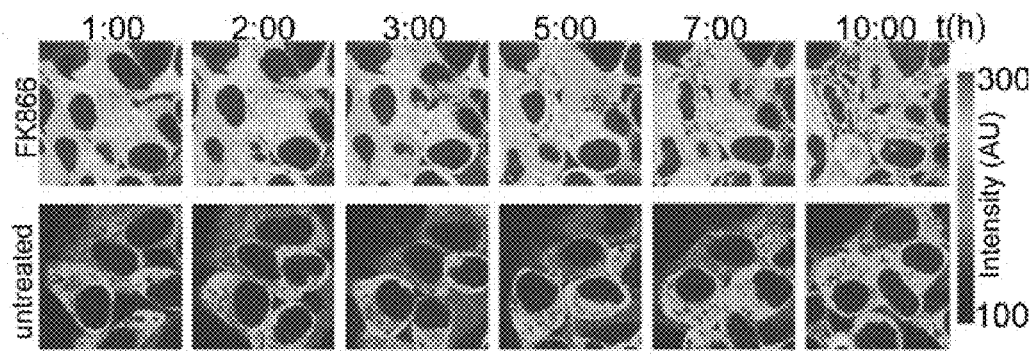

FIG. 15C is a set of ten representative images from live microscopy of HEK293T cells treated for 10 hours with 100 µM FK866.

Figure 15D:
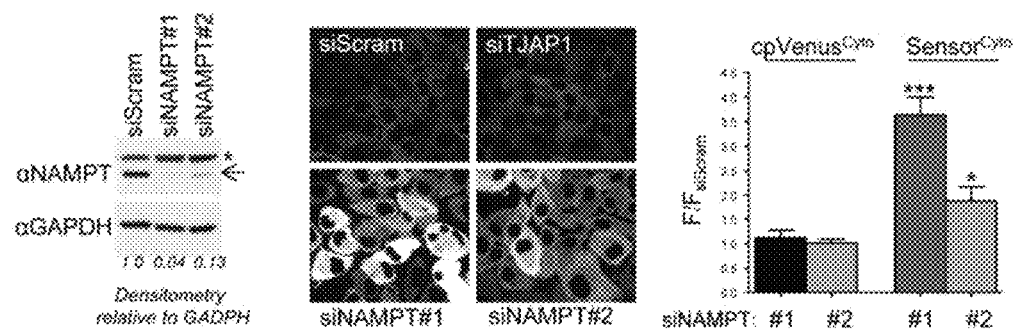

FIG. 15D is an image of an immunoblot, a set of four images, and a bar graph. The left panel shows the efficacy of siRNA depletion of NAMPT (arrow), relative to GAPDH and a scrambled siRNA (siScram). Nonspecific band (*). The middle panel shows the effect of siNAMPT on fluorescence of cytoplasmic sensor expressed in HeLa cells. Depletion of unrelated protein (siTJAP) served as an additional control. The right panel shows the quantitation of relative fluorescence measured by live microscopy. Mean±SD, 2-way ANOVA p<0.01, n=3, Sidak's multiple comparison test, ***p<0.001, *p<0.05 (right).

Figure 15E:
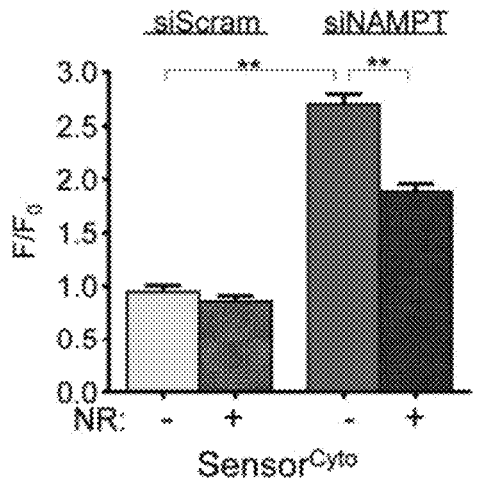

FIG. 15E is a bar graph showing the effect of NR (1 mM, 24 hours) in HeLa cells treated with siNAMPT. Mean±SD, repeated 2 way ANOVA p<0.01, n=3, Sidak's multiple comparison test **p<0.01.

Figure 15F:
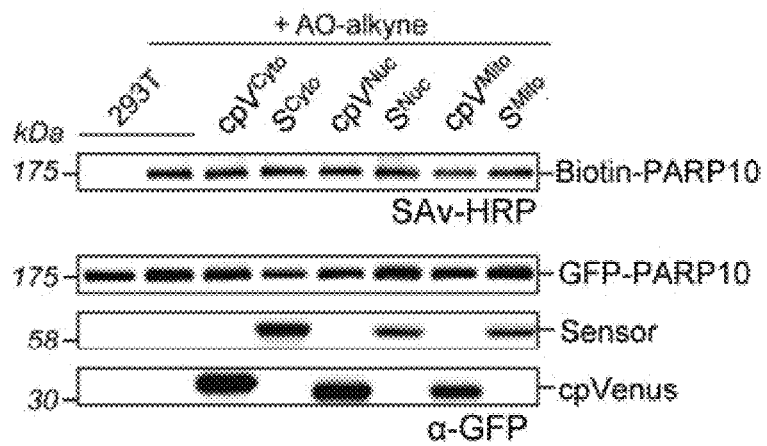

FIG. 15F is an image of an immunoblot showing Expression of sensors had minimal effect on the auto-ribosylation activity of PARP10, measured with a clickable aminooxy probe (AO-alkyne) and Biotin-azide (Kleine H et al, *Mol Cell* 32, 57-69 (2008); incorporated by reference herein) Streptavidin-HRP (SAv-HRP) was used to detect biotinylated-GFP-PARP10 (top panel).

Figure 16A:
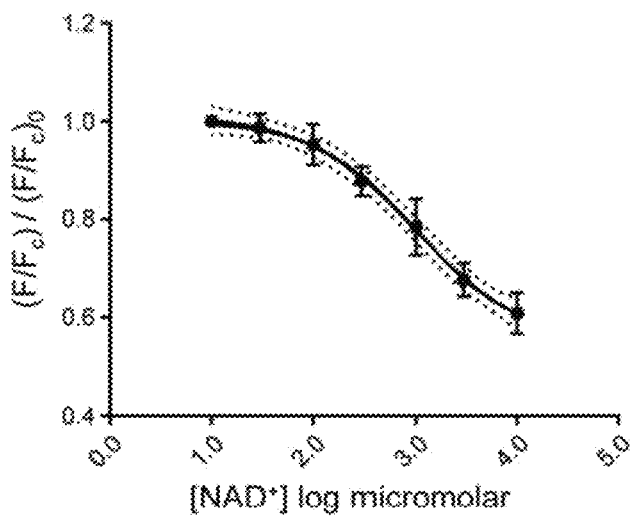

FIG. 16A is a plot showing that the cytoplasmic-seeking version of the sensor was calibrated for NAD+-dependent fluorescence in digitonin permeabilized HEK293T cells. Values were normalized to cpVenus (Fc) and fit with a variable slope model; 95% confidence interval (dotted lines).

Figure 16B:
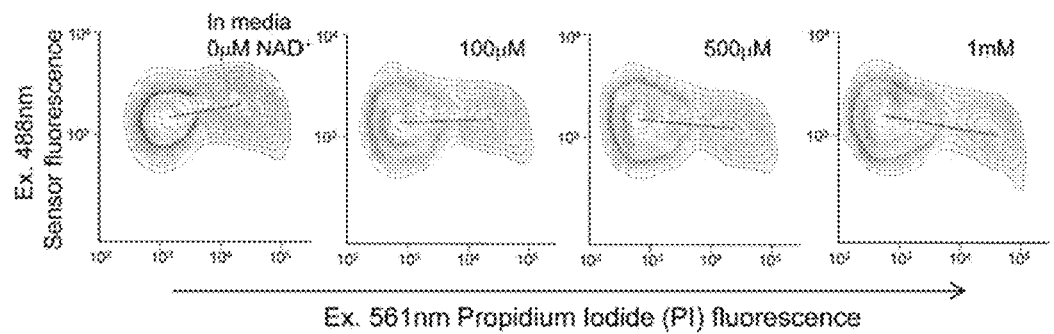

FIG. 16B is a set of four plots showing results wherein the fluorescence of the cytoplasmic sensor in HeLa cells was evaluated after permeabilization in the presence of indicated media NAD+ concentrations. The concentration of cells is depicted with concentric areas; permeabilized cells are shaded blue. The red line indicates the mode of each sub-population.

Figure 16C:
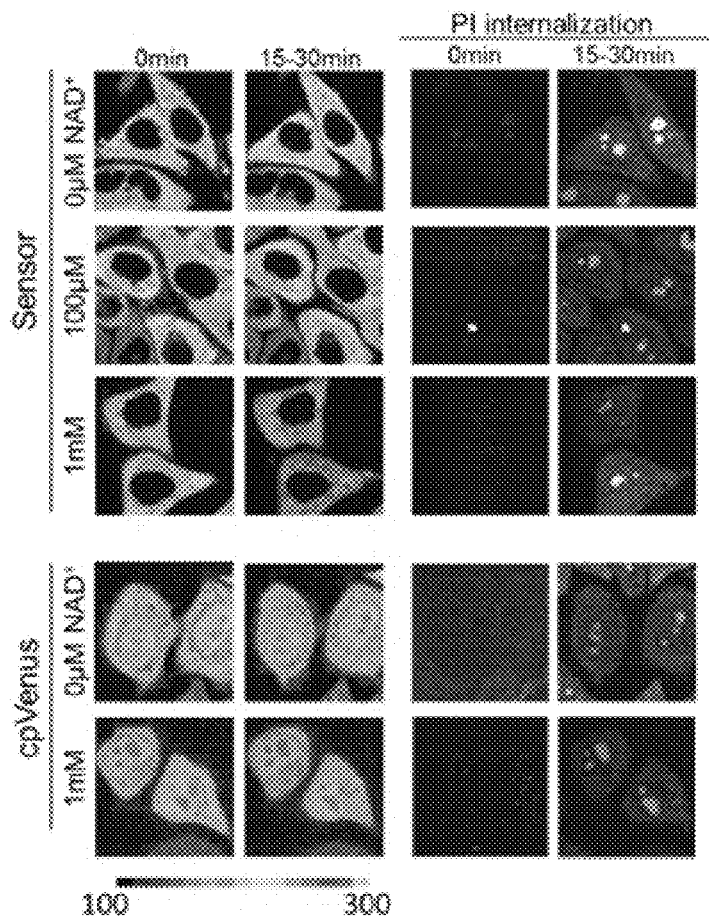

FIG. 16C is a set of 20 representative images from adherent Hela cells that were permeabilized with saponin in the presence of indicated NAD+ concentrations, as monitored by propidium iodide (PI) internalization (right). Live images were captured every 2.5 minutes and fluorescence intensity from 488 nm excitation is normalized to the indicated scale bar.

Figure 17A:
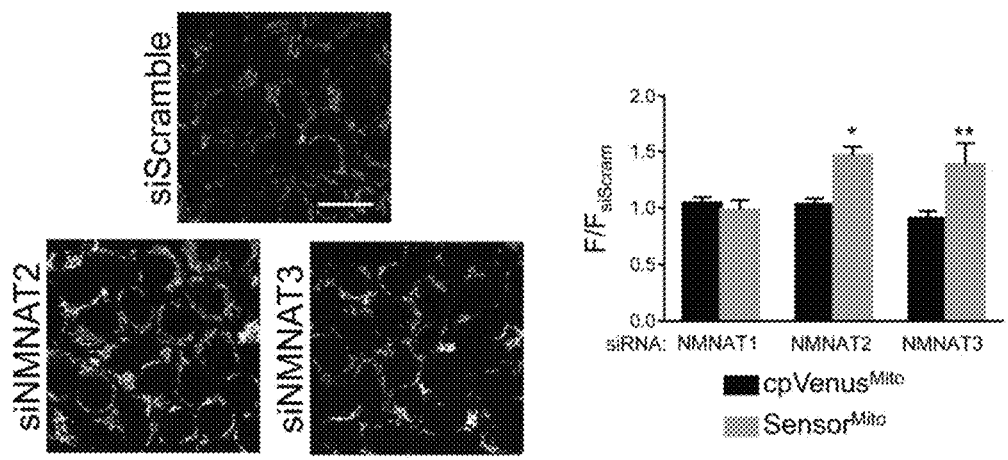

FIG. 17A is a set of three images and a bar graph showing that depletion of either NMNAT2 (#3) or NMNAT3 (#4) decreased mitochondrial NAD+ levels in HEK293T (left panel). Scale bar, 25 µm. Changes in the sensor's fluorescence monitored by live microscopy was quantified and normalized to siScramble and cpVenus controls. Mean±SD, n=3, *p=0.03, **p<0.005.

Figure 17B:
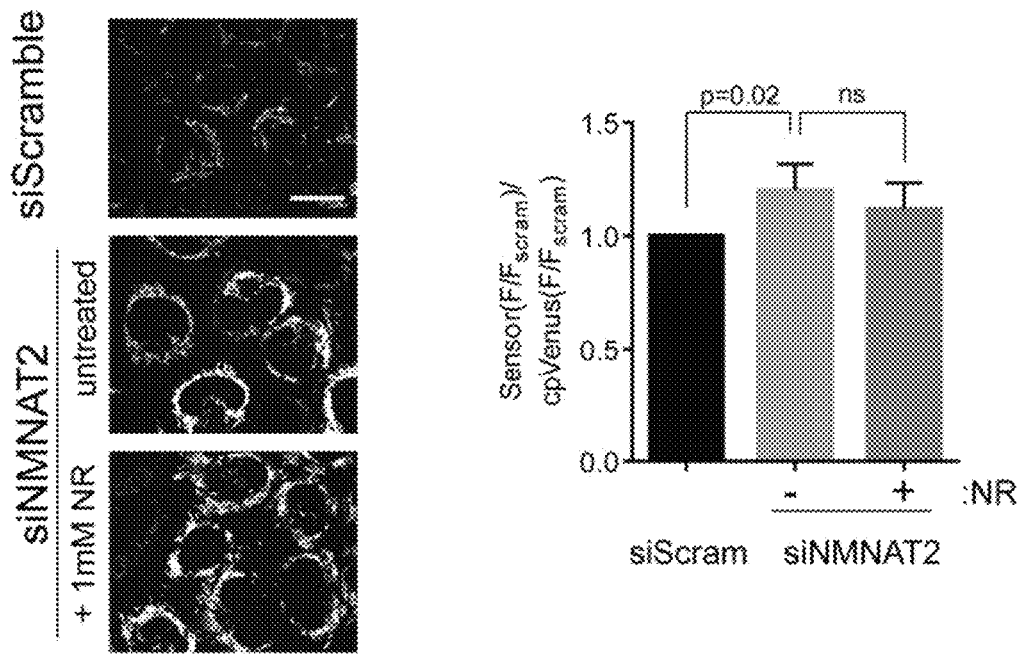

FIG. 17B is a set of three images and a bar graph showing, left panel: NR treatment (1 mM, 24 hours) did not restore lowered NAD+ levels in the mitochondria of HeLa cells resulting from NMNAT2 (#2) depletion. Scale bar, 25 µm. Right panel: quantitation of fluorescence, relative to scramble control and cpVenusMito. Mean±SD, n=3, ns, p>0.05.

Figure 18:
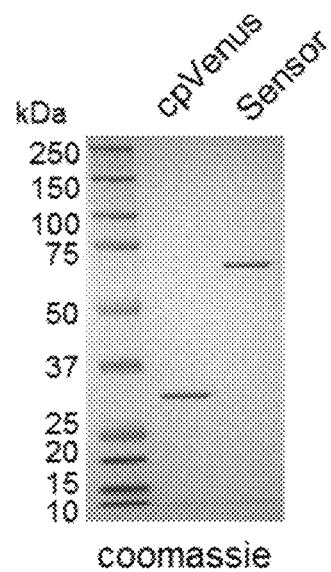

FIG. 18 is an image of a Coomassie-stained SDS-PAGE of purified cpVenus control and NAD+ sensor. The higher molecular weight of the sensor is as expected based on the included NAD+ binding-domain.

Figure 19:
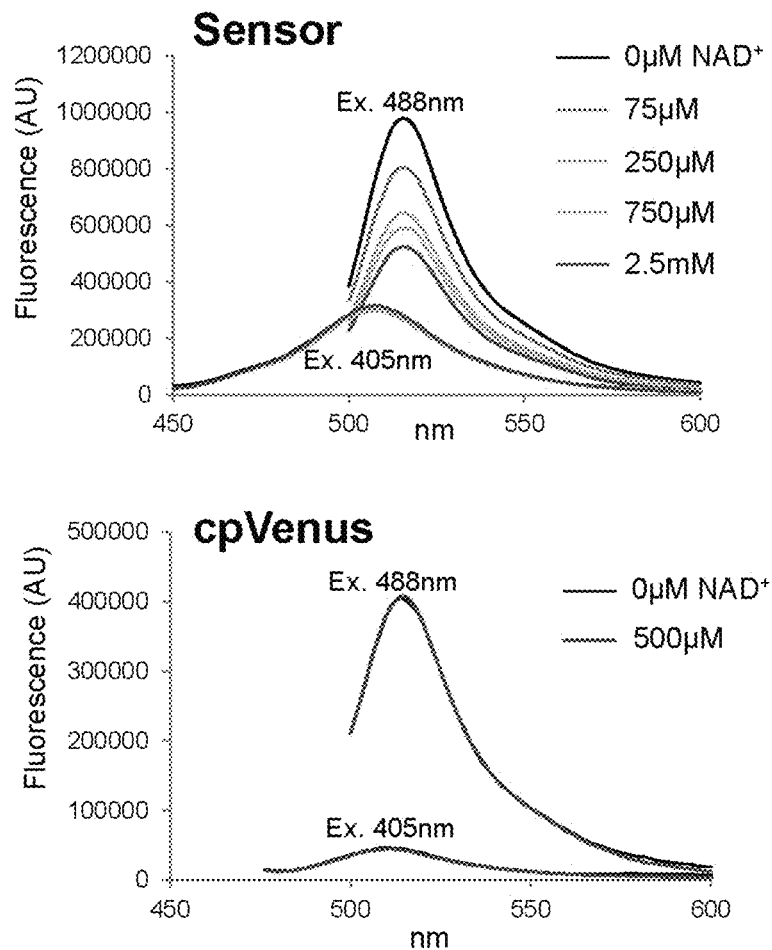

FIG. 19 is a set of two plots showing emission profiles of the NAD+ sensor and cpVenus. Purified sensor or cpVenus (250 nM) were incubated with indicated amounts of NAD+ and excited either at 405 nm or 488 nm. Fluorescence was monitored from 450-600 nm or 500-600 nm, respectively.

Figure 20A:
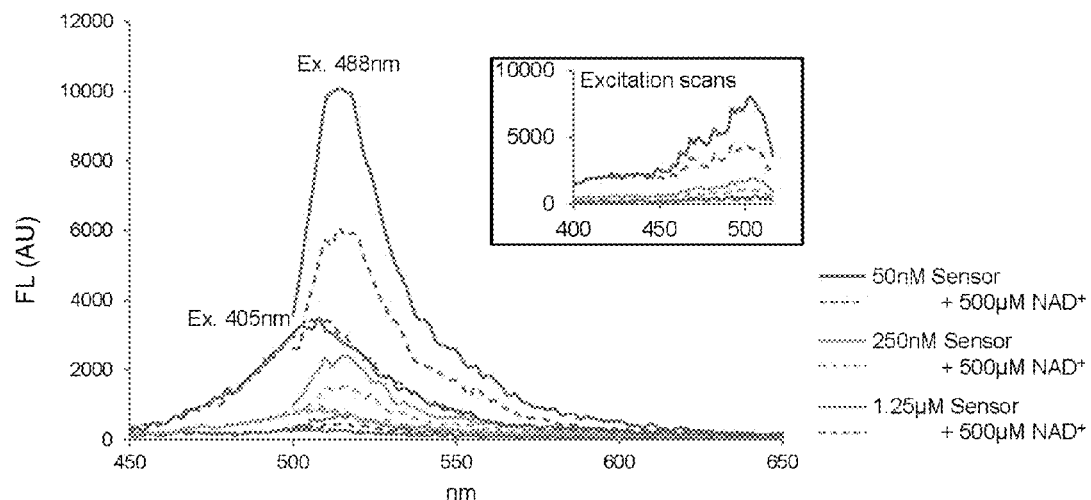

FIG. 20A is a plot showing the amount of sensor was varied as indicated. Fluorescent emission and excitation (inset) scans were obtained with either 0 µM (solid) or 500 µM (dashed) NAD+.

Figure 20B:
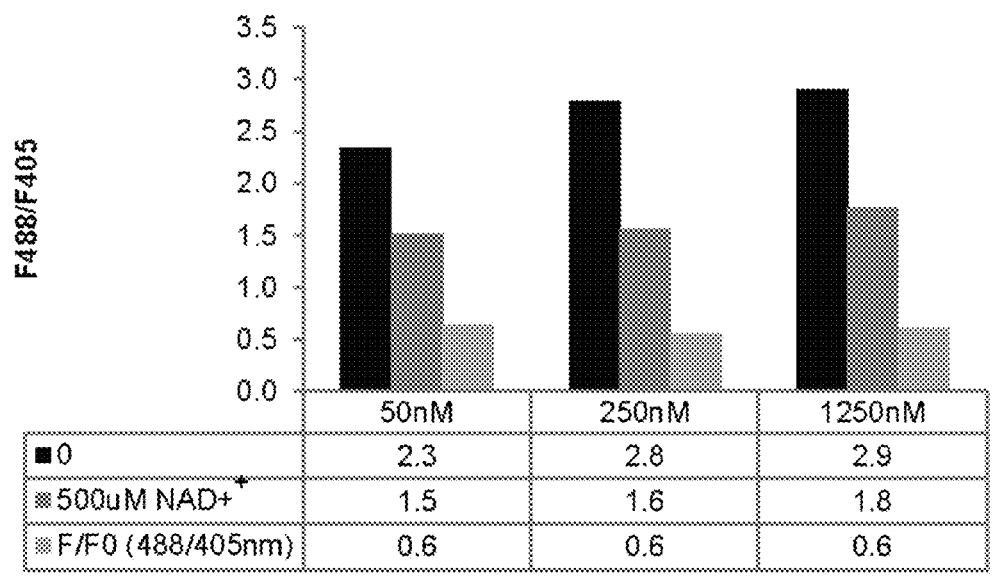

FIG. 20B is a bar graph of the ratio of 488/405 nm fluorescence for the sensor at different concentrations and 0 µM NAD+ (black). The 488/405 nm ratio at different concentrations with 500 µM NAD+ (grey). The NAD+-dependent change reflected by the 488/405 ratio (green).

Figure 21:
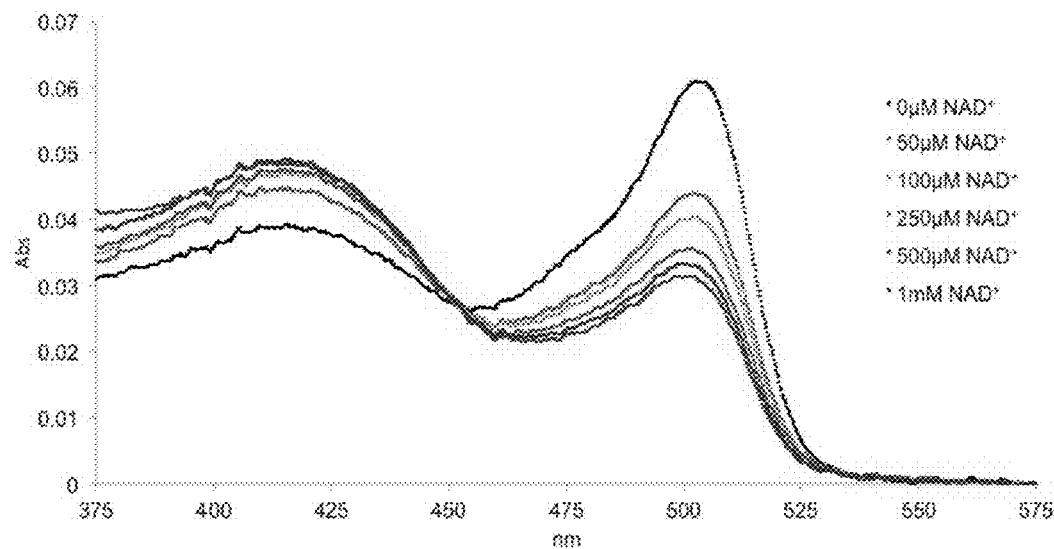

FIG. 21 is a plot showing absorbance scans of the NAD+ sensor. Purified sensor (5 µM) was incubated with indicated amounts of NAD+ (100 mM Tris pH 7.4, 150 mM NaCl @ 20° C.) and absorbance was measured from 360-700 nm. Apparent isosbestic point at ~452 nm.

Figure 22A:
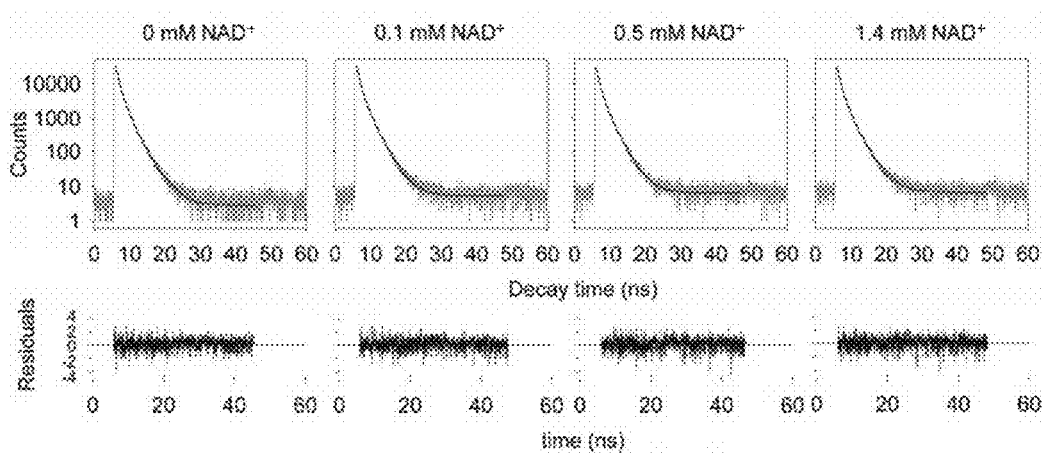

FIG. 22A is a set of plots showing fluorescence decays of 250 nM sensor (ex. 488 nm). These were collected up to 30000 counts in the peak channel and fit with a three-exponential decay function using FluoFit software. Weighted residuals are shown for each fit (bottom panel).

FIG. 22B is a table quantifying the results shown in FIG. 22A. Decays were fit with an exponential decay model $[I(t)=\Sigma_{i-1}^{n}A_i e^{-t/\tau_i}]$. $\tau i$ is the lifetime of the ith component. $A_i$ is the amplitude of the ith component. $<\tau>$ is the amplitude-weighted average lifetime. The increasingly longer integration time required to reach 30,000 counts in the peak channel with increasing NAD+ concentration indicates less fluorescent species are present in the sample.

FIG. 23A is a set of two plots showing the fluorescence (ex. 488 nm) from 250 nM of either the sensor or cpVenus in 100 mM HEPES, 150 mM NaCl at the indicated pH (20° C.).

FIG. 23B is a plot showing the maximum fluorescence (ex. 488 nm) at indicated pH and NAD+ concentrations, mean±SD, n=3.

Figure 23C:
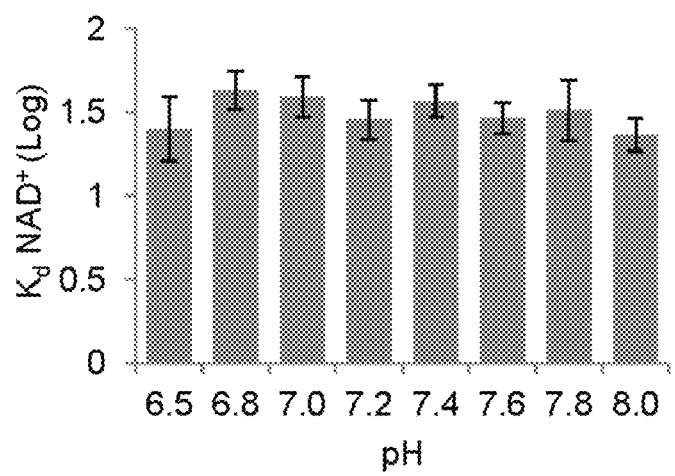

FIG. 23C is a bar graph of a comparison of $K_d$(NAD+) log values for the sensor at the indicated pH levels mean±SD, n=3.

Figure 23D:
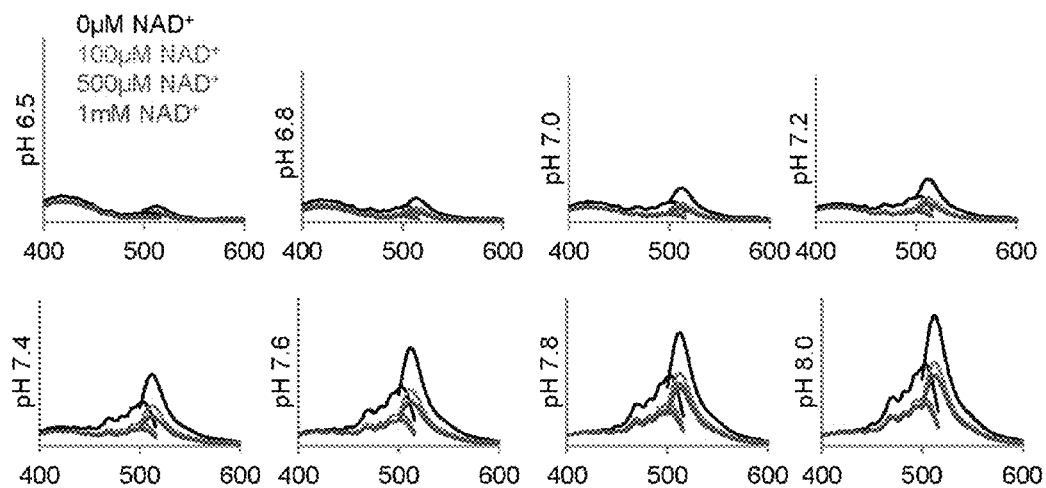

FIG. 23D is a set of 8 plots showing the representative excitation (em. 530 nm) and emission (ex. 488 nm) scans are shown at the indicated pH and NAD+ concentrations.

Figure 24A:
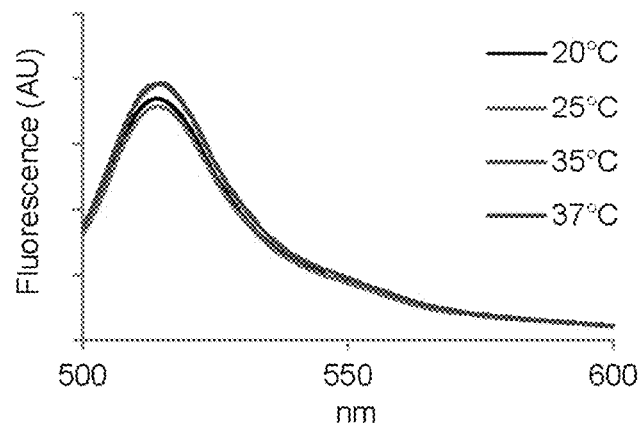

FIG. 24A is a plot showing the fluorescence (ex. 488 nm) from 250 nM sensor in 100 mM HEPES, 150 mM NaCl at the indicated temperatures.

Figure 24B:
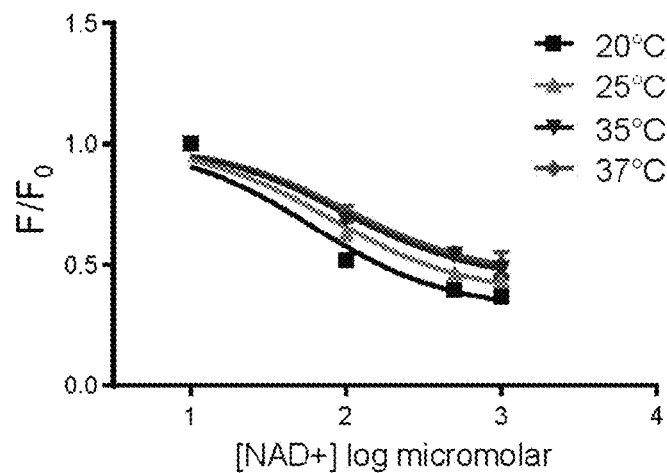

FIG. 24B is a plot of the maximum fluorescence (ex. 488 nm) at indicated temperature and NAD+ concentrations, mean±SD, n=2.

Figure 24C:
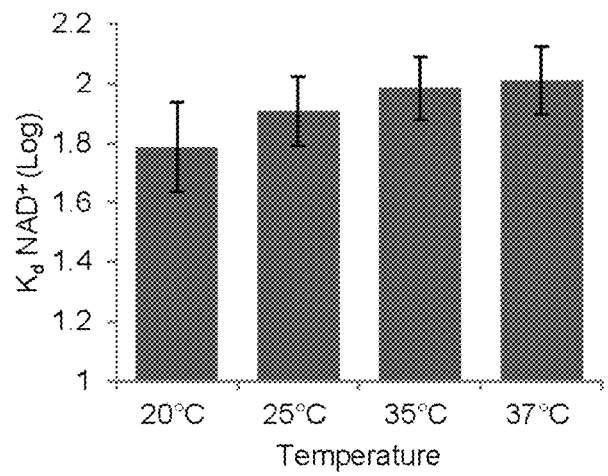

FIG. 24C is a bar graph comparing of $K_d$(NAD+) log values for the sensor at indicated temperatures. Mean±SD, n=2.

Figure 24D:
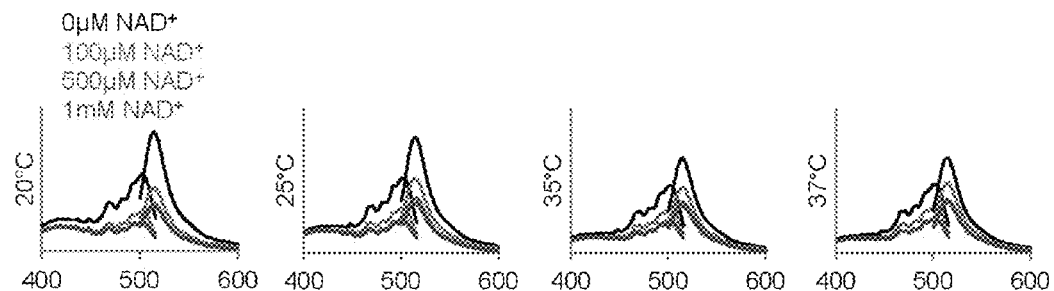

FIG. 24D is a set of four representative plots of excitation (em. 530 nm) and emission (ex. 488 nm) scans at the indicated temperatures and NAD+ concentrations.

Figure 25A:
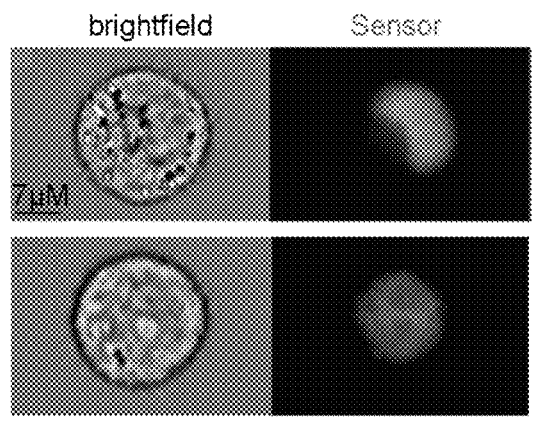

FIG. 25A is a set of four images from an Amnis instrument that combines simultaneous epi-fluorescence microscopy with flow cytometry analysis was used to capture individual HeLa cells stably expressing a nuclear targeted sensor.

Figure 25B:
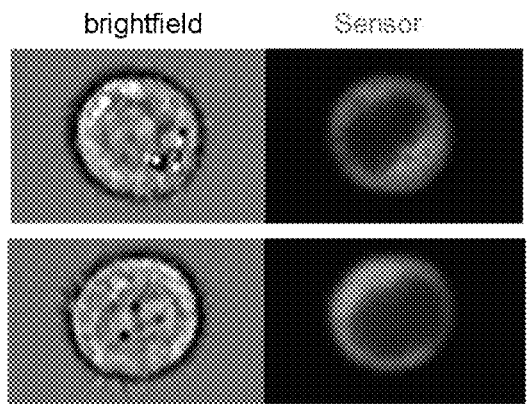

FIG. 25B is a set of four images obtained from the same instrument of individual HeLa cells stably expressing a cytoplasmic targeted sensor.

Figure 25C:
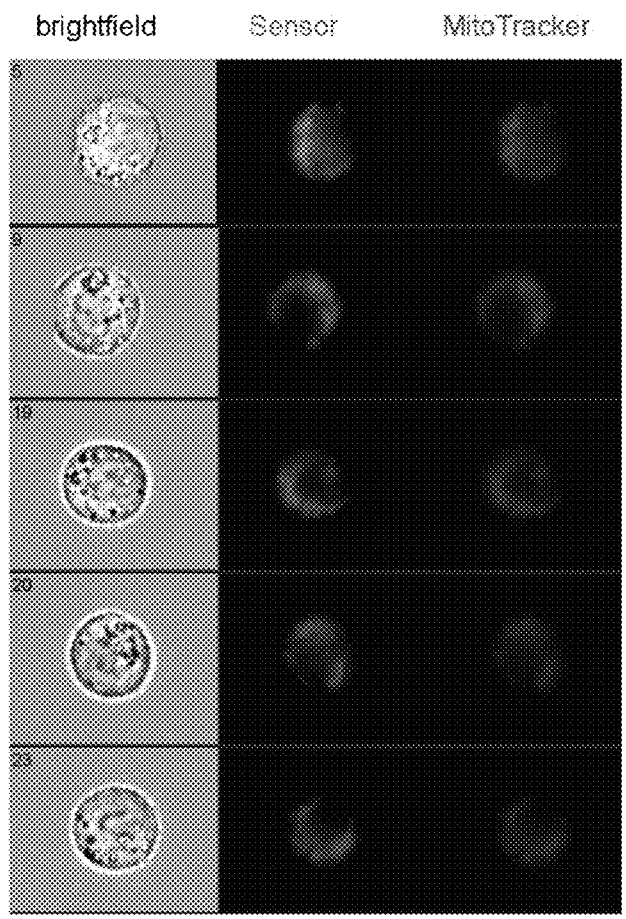

FIG. 25C is a set of fifteen images from the same instrument of individual HeLa cells stably expressing a mitochondrial targeted sensor.

In each of 25A, 25B, and 25C the sensor was retained in its intended subcellular compartment. Using brightfield illumination for comparison the nuclear sensor was detected in the nucleus only (even excluded from nucleoli), and the cytoplasmic sensor evenly distributed in the cytoplasm. Expression of the mitochondrial sensor overlapped with Mitotracker CMXRos (red, right images of FIG. 25C).

Figure 26:
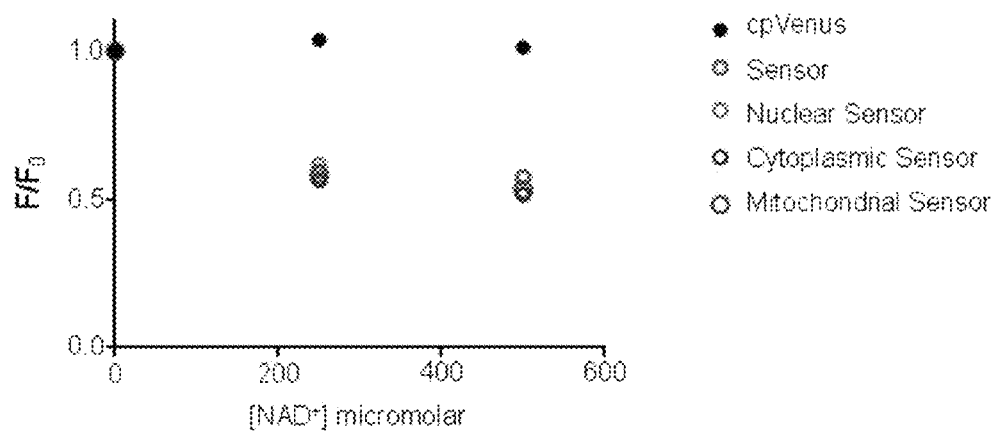

FIG. 26 is a plot of Purified sensors with localization sequences were compared to the original sensor in a cell free system. Relative fluorescence intensity following excitation at 488 nm was plotted as a function of NAD+ concentration.

Figure 27:
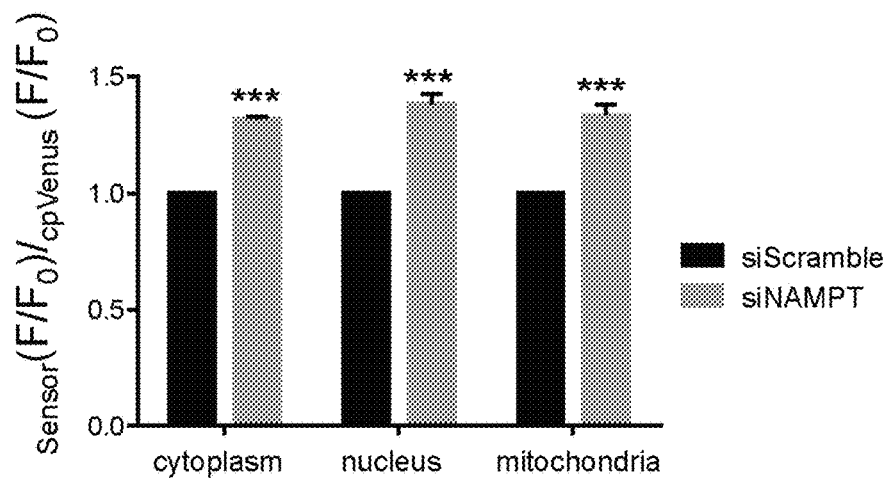

FIG. 27 is a bar graph showing the Effects of NAMPT depletion on nuclear and mitochondrial NAD+. Depletion of NAMPT in HEK293T cells for 72-96 hours resulted in decreased NAD+ levels in the cytoplasm, nucleus, and mitochondria. The fluorescence ratio 488/405 was measured by flow cytometry and normalized to siScramble (F0) and the ratio of cpVenus controls. Mean±SD, n=3, ***$p<0.001$.

Figure 28:
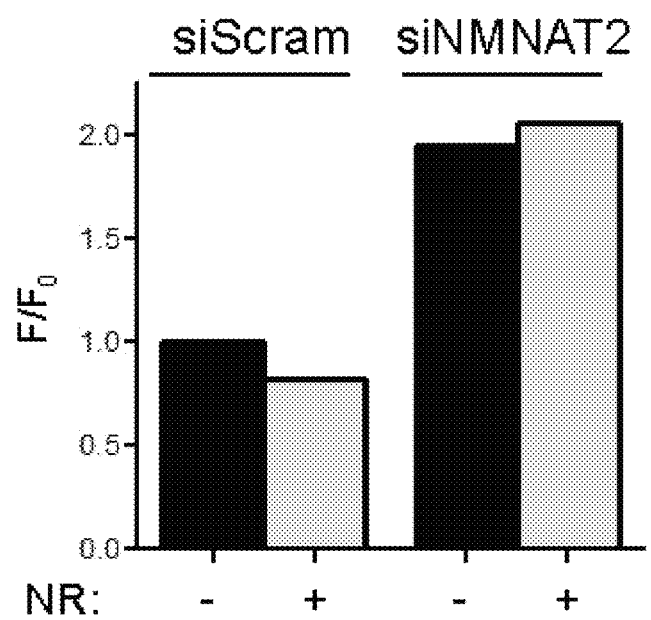

FIG. 28 is a bar graph showing that Nicotinamide riboside (NR) has no direct effect on the fluorescence of the cytoplasmic sensor. The cytoplasmically-localized sensor reported a decrease of cytoplasmic NAD+ following depletion of NMNAT2. NR treatment (1 mM, 24 hours) did not alter the fluorescence of the sensor when NMNAT2 was depleted.

Figure 29:
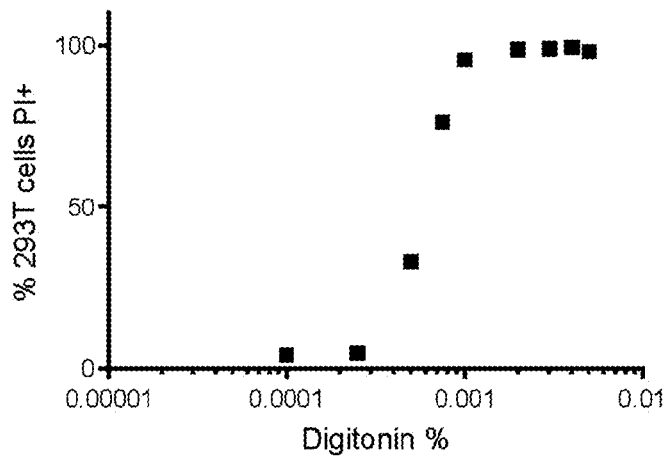
Figure 29:
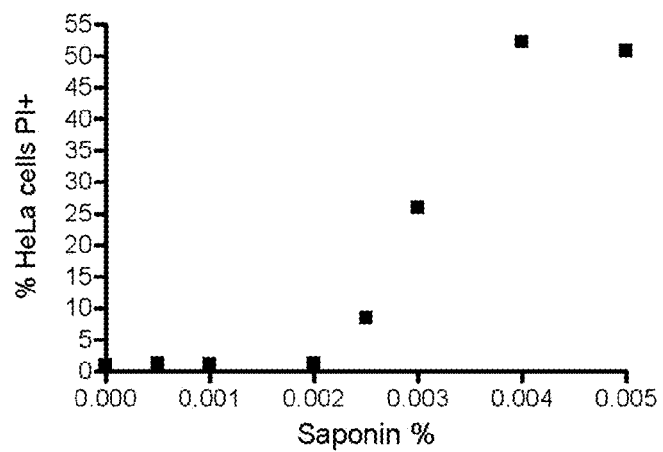

FIG. 29 is a plot showing the concentration of digitonin or saponin required to permeabilize cells. Permeabilization was monitored in real time by the internalization of propidium iodide (PI), and flow cytometry (ex. 561 nm em. 670/30 nm). HeLa or 293T cells were incubated with varying amounts of detergent for 15-30 minutes at RT. The percentage of cells taking up PI is shown as a function of detergent concentration.

Figure 30:
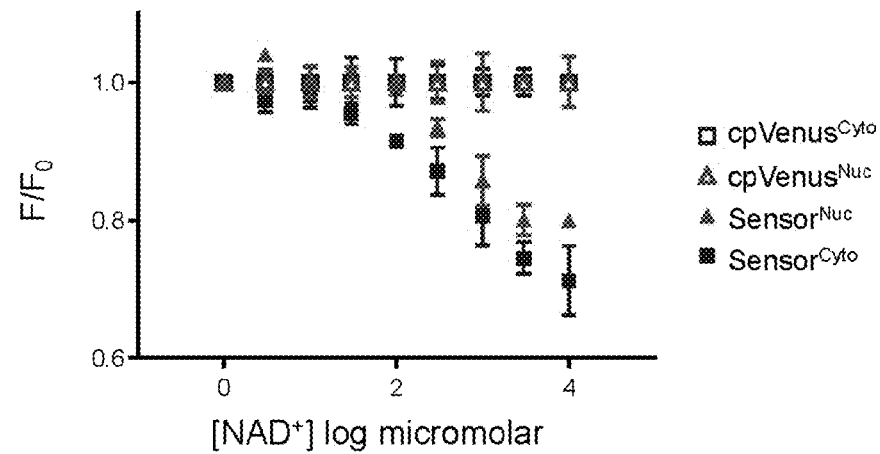

FIG. 30 is a plot showing the relative fluorescence changes in cytoplasmic and nuclear sensors and cpVenus controls. Clonal populations of HEK293T cells stably expressing either nuclear (Nuc) or cytoplasmic (Cyto) sensor or cpVenus control were permeabilized with 0.001% digitonin and equilibrated with indicated NAD+ concentrations for 15-30 minutes at room temperature. Relative fluorescence changes are plotted as a function of NAD+ concentration.

Figure 31:
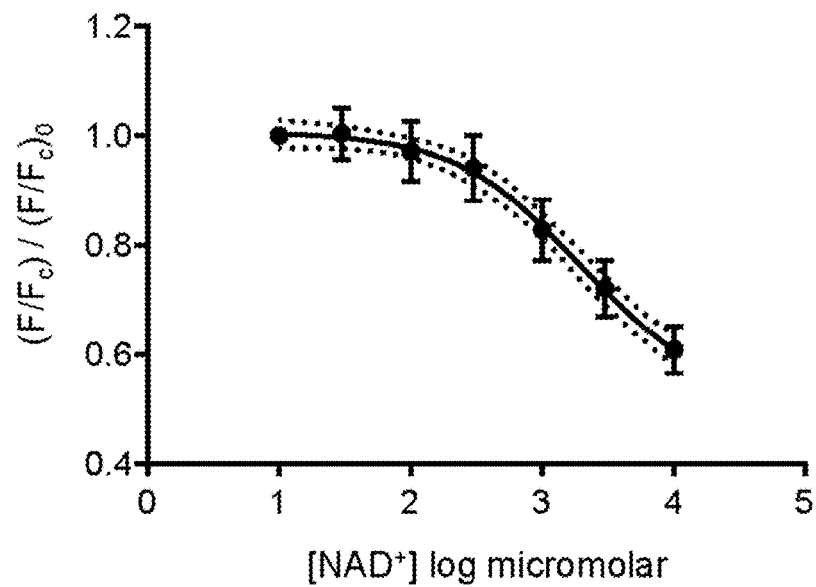

FIG. 31 is a calibration curve for the nuclear sensor in HEK293T cells. HEK293T cells were permeabilized with 0.001% digitonin and equilibrated with indicated NAD+ concentrations for 15 minutes at room temperature. Fluorescence ratio (488/405) was measured with flow cytometry from the sensor and normalized to the fluorescence from similarly treated nuclear-cpVenus control cells ($F_c$). The mean from 19 independent measurements of the sensor in non-permeabilized cells was interpolated onto the graph to reveal the free nuclear NAD+ value under homeostasis. Mean±SD, 95% confidence intervals (dotted lines).

Figure 32:
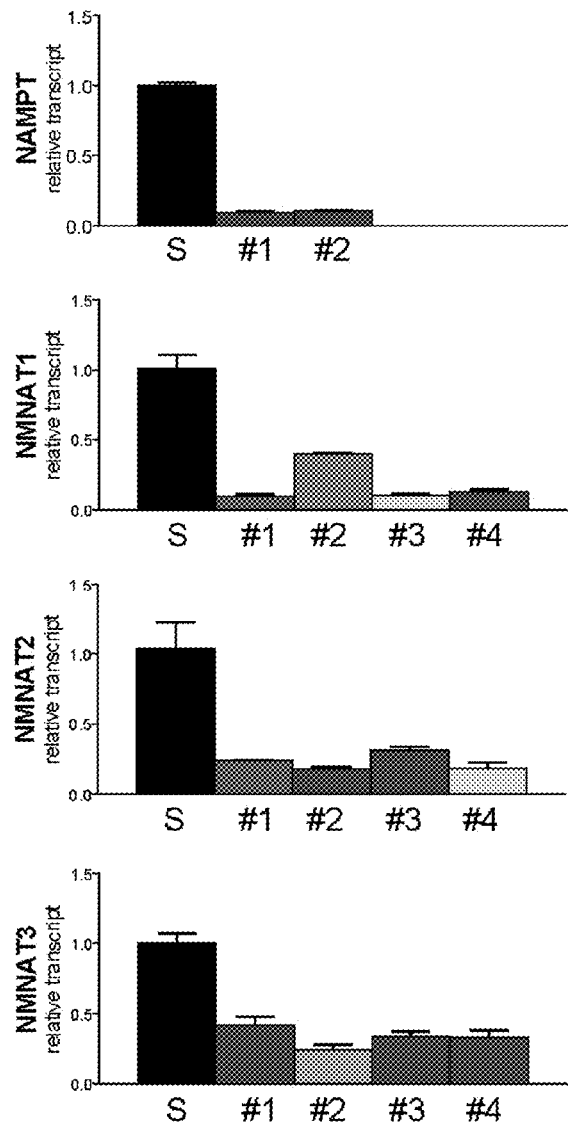
Figure 32:
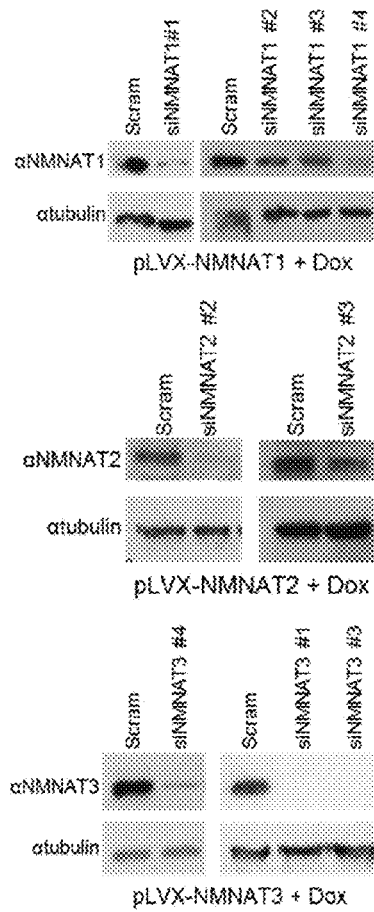

FIG. 32 is a set of four bar graphs (left) and three images of immunoblots (right) that collectively illustrate validation of the siRNAs used herein. Two to four distinct siRNA sequences were evaluated for knockdown efficiency with both qPCR and Western blotting in HEK293T. Cells were reverse transfected with 25 nM indicated siRNAs or Scramble control (S or Scram) and evaluated 72 hours posttransfection. siRNAs used in this study are highlighted in red and were chosen based on their specific targeting of endogenous transcript with minimal cell toxicity. Left panels show the relative levels of endogenous transcripts were quantified with qPCR 72 hours post transfection of the siRNA. Right panels: Due to a lack of antibodies able to recognize endogenous NMNAT1, 2, and 3, generated doxycycline-inducible cell lines were generated to ectopically express these proteins. Cell lines were treated with 50 ng/mL doxycyclin (Dox) 48 hours post-transfection for 24 hours. Cells were collected for Western blot analysis at 72 hours post-transfection.

Figure 33:
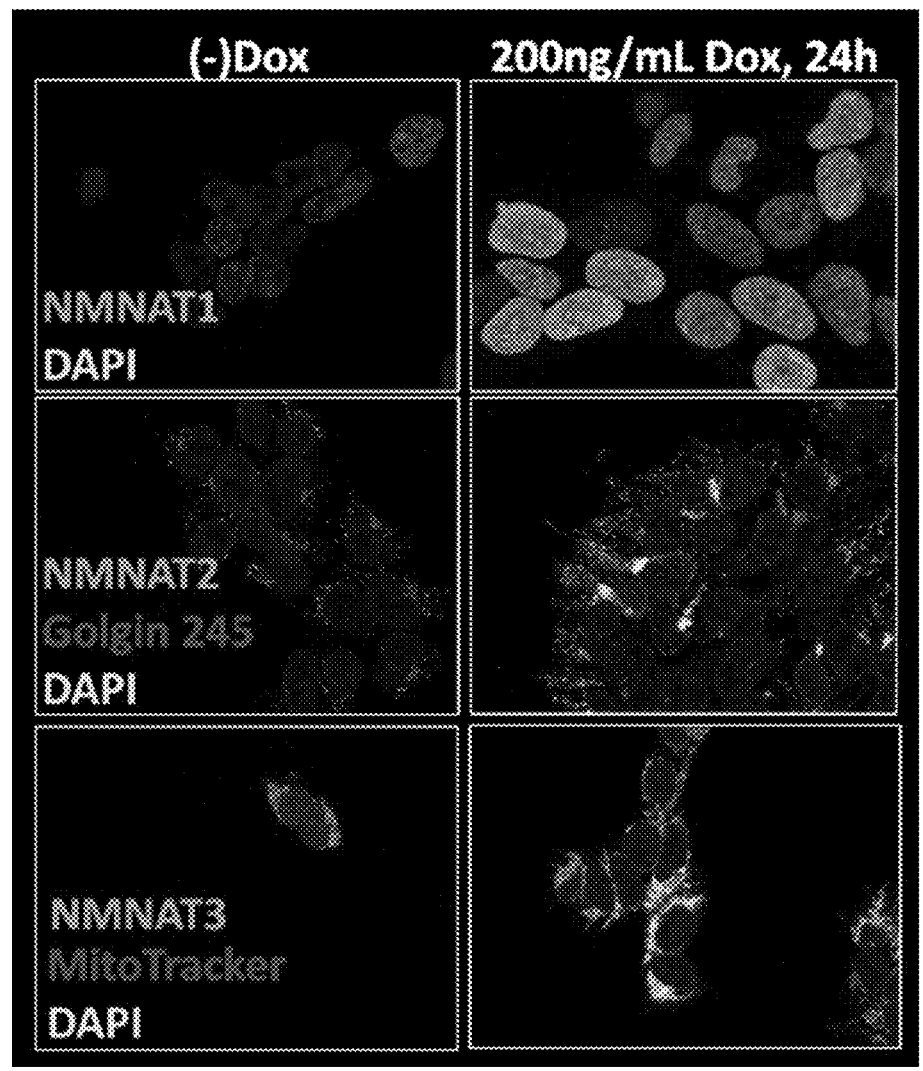

FIG. 33 is a set of six images of Stable HEK293T cell lines were generated using the Tet-ON inducible system (Clontech) to ectopically express either NMNAT1, NMNAT2, or NMNAT3. Cells were induced for 24 hours with 200 ng/mL of doxycyclin, fixed with 4% paraformaldehyde and stained with antibodies recognizing the NMNAT enzymes. Localization was confirmed with DAPI (nuclear), Golgin 245 (trans Golgi apparatus), and MitoTracker CMXRos (mitochondria).

Figure 34A:
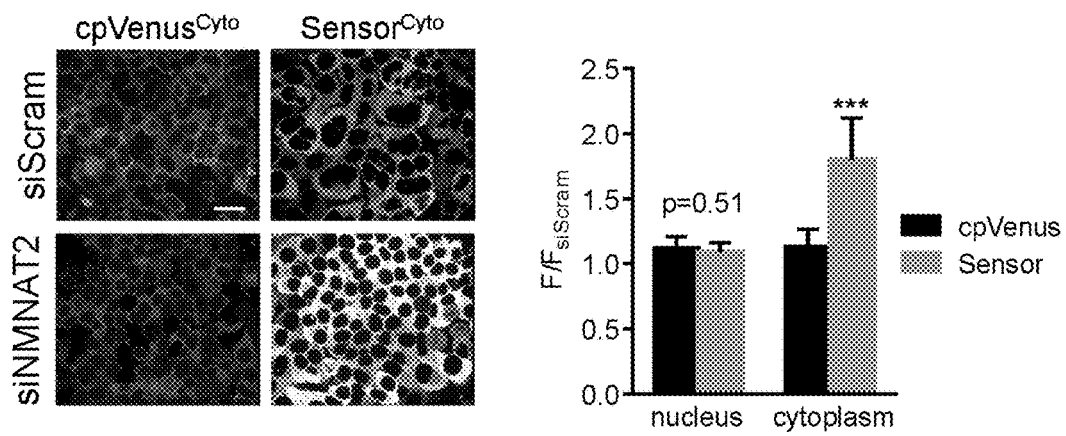

FIG. 34A is a set of four images (left) and a bar graph (right) illustrating depletion of NMNAT2 that resulted in decreased cytoplasmic NAD+ levels in HEK293T cells (left images) but no significant change in nuclear levels (bar graph, right). Mean±SD, n=5. Scale bar, 25 µm.

Figure 34B:
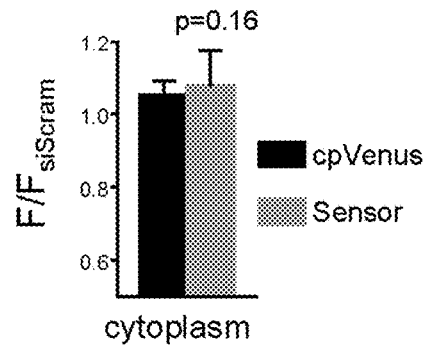

FIG. 34B is a bar graph showing that in HEK293T cells with relatively high NMNAT2, depletion of NMNAT1 was not sufficient to deplete NAD+ levels in the cytoplasm, measured by flow cytometry. Statistical analyses were performed on the ratio $(F/F_{scram})/(F_{cp}/F_{cpVScram})$, mean±SD, n=3. This contrasts with the observations in HeLa cells in pane C, which express predominantly NMNAT1.

Figure 34C:
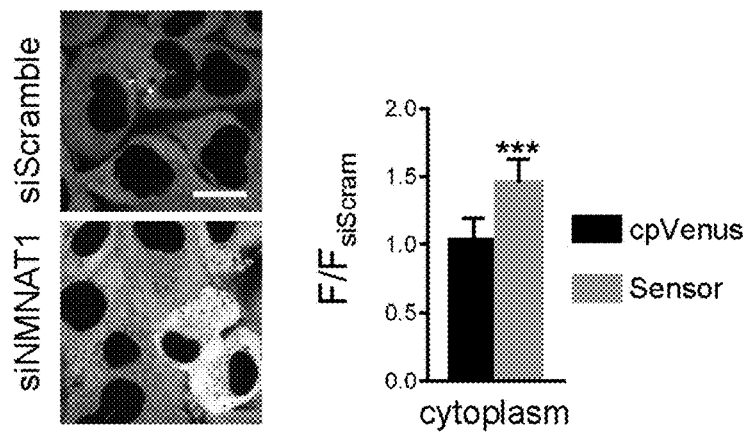

FIG. 34C is a set of images (left) and a bar graph (right) showing in HeLa cells, which express predominantly NMNAT1, the same siRNAs targeting NMNAT1 decreased cytoplasmic NAD+. Scale bar, 25 µm. The bar graph shows quantitation of changes in cytoplasmic sensor fluorescence. Statistical analyses were performed on the fluorescence ratios normalized to siScramble and cpVenus $(F/F_{Scram})/(F_{cpV}/F_{cpVScram})$. Mean±SD, n=3, ***$p<0.001$.

Figure 35:
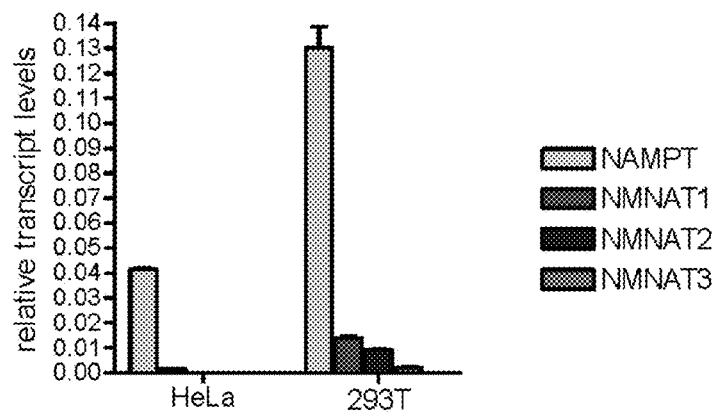
Figure 35:
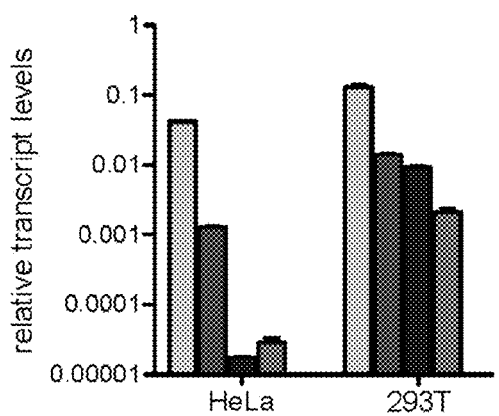

FIG. 35 is a set of two bar graphs showing the results where quantitative PCR was performed using cDNA from either HeLa or HEK293T cells using validated gene-specific primer sets, as indicated. Relative transcript levels were normalized to GAPDH and either plotted with a linear (top) or logarithmic (bottom) y-axis.

Figure 36A:
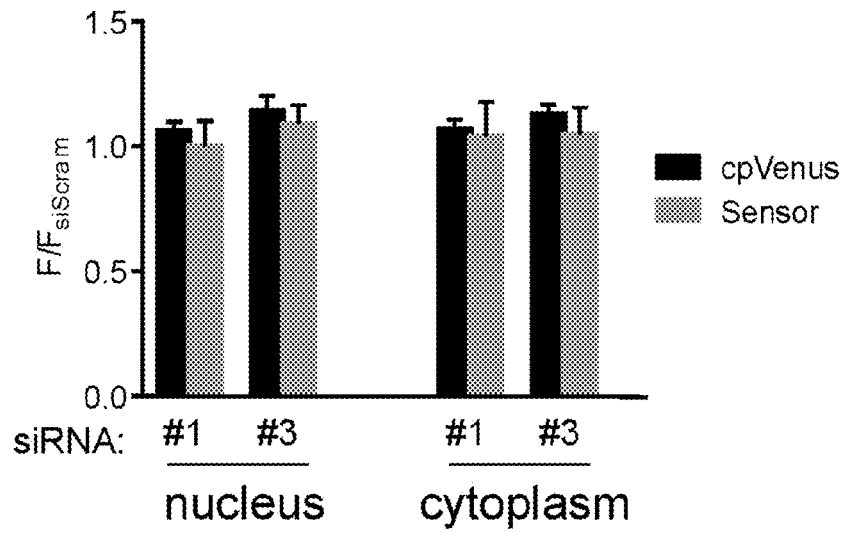

FIG. 36A is a bar graph showing Depletion of NMNAT3 with different siRNAs had no significant effect on NAD+ levels in the nucleus or cytoplasm of HEK293T cells. Fluorescence was measured by flow cytometry and analyzed using a REML statistical model. Mean±SD, n=4 $p>0.05$.

Figure 36B:
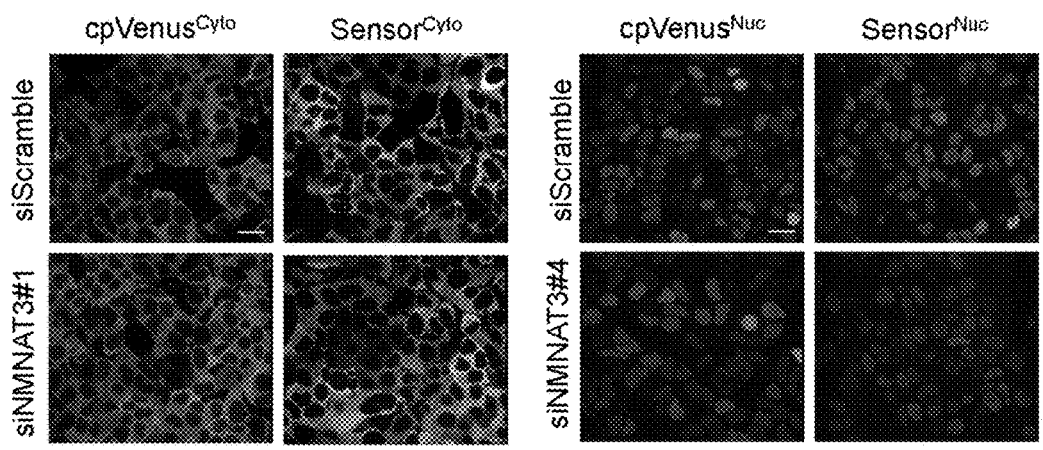

FIG. 36B is a set of 8 representative images of the sensor's fluorescence in the cytoplasm and nucleus of live cells following depletion of siNMNAT3 with various siRNAs. Scale bar, 25 µm.

Figure 37:
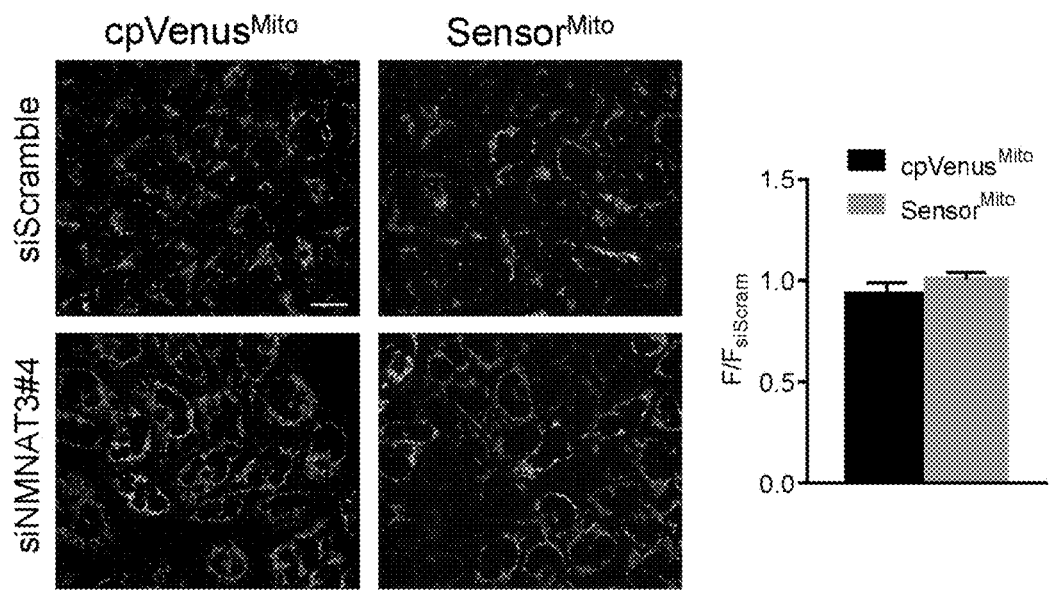

FIG. 37 is a set of four representative images (left) of mitochondria localized sensor or cpVenus control (scale bar 25 µm) and a bar graph (right) showing the quantitation of fluorescence. Mean±SD, n=3 $p>0.05$.

Figure 38:
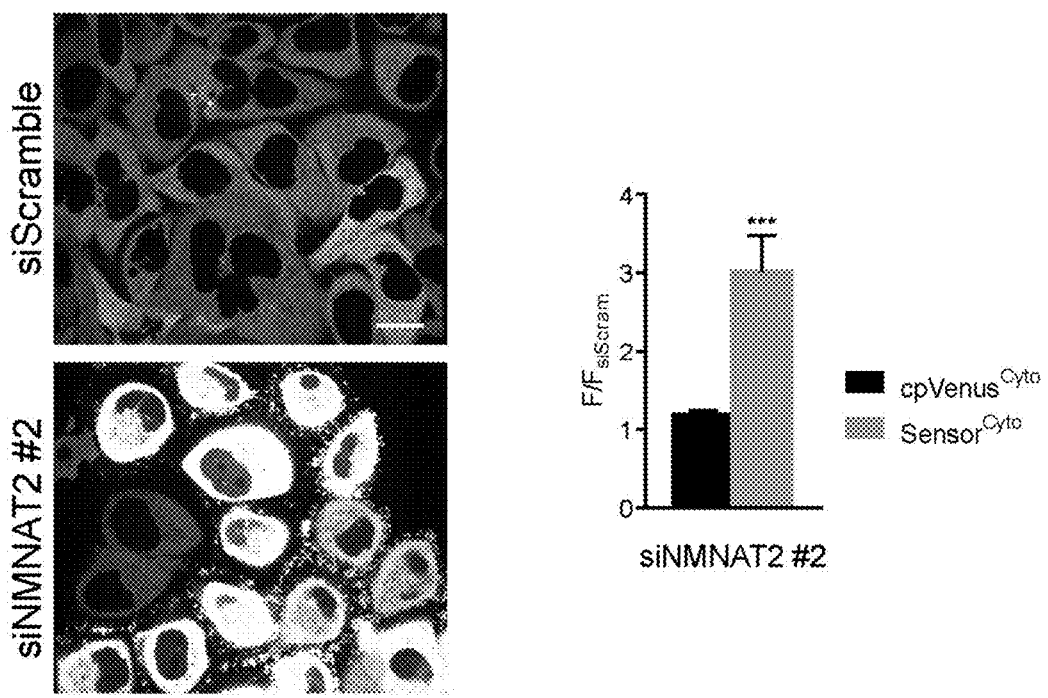

FIG. 38 is a set of two images (left) and a bar graph (right) showing that depletion of NMNAT2 in HeLa cells resulted in decreased cytoplasmic NAD+ levels, demonstrating its activity in these cells. The representative images have a scale bar of 25 μM. The bar graph is the quantitation of fluorescence from live microscopy. Mean±SD, n=3, ***p<0.001.

The patent or application file contains at least one drawing executed in color. Copies of this patent or patent application publication with color drawing(s) will be provided by the Office upon request and payment of the necessary fee.

SEQUENCE LISTING

SEQ ID NO: 1 is the sequence of an example of a NAD+ dependent DNA ligase adenylation domain fragment (LigA 2-70 in FIG. 13).

SEQ ID NO: 2 is the sequence of an example of a NAD+ dependent DNA ligase adenylation domain fragment (LigA 78-317 in FIG. 13)

SEQ ID NO: 3 is the sequence of an example of a peptide linker ("Linker" or "Linker 2" in FIG. 13A-E).

SEQ ID NO: 4 is the sequence of an example of a peptide linker (Linker 1 in FIG. 13E).

SEQ ID NO: 5 is the sequence of an example of a fluorescent protein (cpVenus).

SEQ ID NO: 6 is the sequence of an example of a NAD+ biosensor polypeptide.

SEQ ID NO: 7 is the sequence of an example of a NAD+ biosensor polypeptide.

SEQ ID NO: 8 is the sequence of an example of a NAD+ biosensor polypeptide.

SEQ ID NO: 9 is the sequence of an example of a NAD+ biosensor polypeptide.

SEQ ID NO: 10 is the sequence of an example of a NAD+ biosensor polypeptide.

SEQ ID NO: 11 is the sequence of a FLAG® tag.

SEQ ID NO: 12 is the sequence of an example of a HA tag.

SEQ ID NO: 13 is the sequence of an example of a mitochondrial localization tag.

SEQ ID NO: 14 is the sequence of an example of a nuclear export signal.

SEQ ID NO: 15 is the sequence of an example of a nuclear localization signal.

DETAILED DESCRIPTION

Terms

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCR Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." In addition, the materials, methods, and examples are illustrative only and not intended to be limiting. In order to facilitate review of the various embodiments of the disclosure, the following explanations of specific terms are provided:

Contacting: Placement in direct physical association, including contacting of a solid with a solid, a liquid with a liquid, a liquid with a solid, or either a liquid or a solid with a cell or tissue, whether in vitro or in vivo. Contacting can occur in vitro with isolated cells or tissue or in vivo by administering to a subject.

Conservative amino acid substitution: A substitution of an amino acid residue for another amino acid residue having similar biochemical properties. "Conservative" amino acid substitutions are those substitutions that do not substantially affect or decrease an activity of a polypeptide such as a DNA ligase binding domain or a fluorescent protein. A polypeptide can include one or more conservative substitutions up to and including 1-10 total conservative substitutions, 1% conservative substitutions, 5% conservative substitutions, 10% conservative substitutions, 15% conservative substitutions, 20% conservative substitutions, 25% conservative substitutions, 30% or more conservative substitutions, or any intervening value. Specific, non-limiting examples of a conservative substitution include the following:

| Original Amino Acid | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

While examples of polypeptide sequences are provided in the amino acid sequences attached to this application, not all variants of polypeptide sequences with all possible combinations of conservative amino acid substitutions encompassed by the disclosure are provided in the sequence listing. This table can be used in combination with the sequence listing to provide explicit examples of polypeptide sequences encompassed by the disclosure.

cpVenus: Venus is a variant of Yellow Fluorescent Protein (YFP) which in turn is a derivative of Green Fluorescent Protein derived from the *Aequorea victoria* jellyfish. Venus has an F→L mutation at the phenylalanine at position 46 in YFP (F46L) (U.S. Pat. No. 7,595,375; incorporated by reference herein). The fluorophore termed cpVenus herein is a circularly permuted version of Venus. A circular permutation of a protein has an altered amino acid sequence than the parent protein, but a similar 3-dimensional structure. For example, cpVenus has an altered N and C terminus relative to Venus, but has a similar structure. A circularly permuted fluorescent protein is a recombinant fluorescent protein that has been modified such that the native N and C termini are joined together in frame with or without an intervening spacer or linker sequence.

Domain: A domain of a polypeptide or protein may be any part of a protein that exhibits a particular defined structure and/or mediates a particular protein function. An example of a domain is the adenylation domain of an $NAD^+$ dependent DNA ligase.

Fluorescent protein: A protein characterized by a barrel structure that allows the protein to absorb light and emit it at a particular wavelength. Fluorescent proteins include green fluorescent protein (GFP) modified GFPs and GFP derivatives and other fluorescent proteins, such as EGFP, EBFP, YFP, BFP, CFP, ECFP, and circularly permutated fluorescent proteins such as cpVenus.

Label: A label may be any substance capable of aiding a machine, detector, sensor, device, column, or enhanced or unenhanced human eye from differentiating a labeled composition from an unlabeled composition. Labels may be used for any of a number of purposes and one skilled in the art will understand how to match the proper label with the proper purpose. Examples of uses of labels include purification of biomolecules, identification of biomolecules, detection of the presence of biomolecules, detection of protein folding, and localization of biomolecules within a cell, tissue, or organism. Examples of labels include but are not limited to: radioactive isotopes (such as carbon-14 or $^{14}C$) or chelates thereof; dyes (fluorescent or nonfluorescent), stains, enzymes, nonradioactive metals, magnets, protein tags, any antibody epitope, any specific example of any of these; any combination between any of these, or any label now known or yet to be disclosed. A label may be covalently attached to a biomolecule or bound through hydrogen bonding, Van Der Waals or other forces. A label may be covalently or otherwise bound to the N-terminus, the C-terminus or any amino acid of a polypeptide or the 5' end, the 3' end or any nucleic acid residue in the case of a polynucleotide.

One particular example of a label is a protein tag. A protein tag comprises a sequence of one or more amino acids that may be used as a label as discussed above, particularly for use in protein purification. In some examples, the protein tag is covalently bound to the polypeptide. It may be covalently bound to the N-terminal amino acid of a polypeptide, the C-terminal amino acid of a polypeptide or any other amino acid of the polypeptide. Often, the protein tag is encoded by a polynucleotide sequence that is immediately 5' of a nucleic acid sequence coding for the polypeptide such that the protein tag is in the same reading frame as the nucleic acid sequence encoding the polypeptide. Protein tags may be used for all of the same purposes as labels listed above and are well known in the art. Examples of protein tags include chitin binding protein (CBP), maltose binding protein (MBP), glutathione-S-transferase (GST), poly-histidine (His), thioredoxin (TRX), FLAG®, V5, c-Myc, HA-tag, and so forth.

A His-tag facilitates purification and binding to on metal matrices, including nickel matrices, including nickel matrices bound to solid substrates such as agarose plates or beads, glass plates or beads, or polystyrene or other plastic plates or beads. Other protein tags include BCCP, calmodulin, Nus, Thioredoxin, Streptavidin, SBP, and Ty, or any other combination of one or more amino acids that can work as a label described above.

Mutation: A mutation can be any difference in the sequence of a biomolecule relative to a reference or consensus sequence of that biomolecule. A mutation can be observed in a nucleic acid sequence or a protein sequence. Such a reference or consensus sequence may be referred to as "wild type". For example, wild type versions of *E. faecalis* DNA ligase A are identical the consensus sequence found in live bacteria. However, mutations can be introduced in the polyadenylation domain of *E. faecalis* DNA ligase A that result in an improved $NAD^+$ biosensor. Such mutations include substitution mutations in amino acids K122 (such as K122L, also K44L in the second fragment) and/or amino acid D288 (such as D288N, also referred to as D210N in the second fragment) or equivalent amino acid substitutions in other DNA ligase adenylation domains from other organisms.

$NAD^+$ Dependent DNA Ligase: An enzyme that catalyzes the formation of a phosphodiester bond in DNA molecules. Specifically, it catalyzes the formation a covalent bond between the 3' hydroxyls of a double stranded DNA molecule with the 5' phosphates of a second double stranded DNA molecule. Bacterial DNA ligase binds to nicotinamide adenine dinucleotide ($NAD^+$), which provides the energy for the formation of the covalent bond. $NAD^+$ dependent DNA ligases comprise an adenylation domain. The adenylation domain of a given $NAD^+$ dependent DNA ligase (for example, an $NAD^+$ dependent DNA ligase from a bacterial strain) can be identified by one of skill in the art in light of this disclosure through sequence homology with other known $NAD^+$ dependent DNA ligases. In general, the adenylation domain is a domain of 300-350 amino acids located near the N terminus of the $NAD^+$ dependent DNA ligase.

In some aspects of the invention a fragment of the $NAD^+$ dependent DNA ligase adenylation domain is described. The fragment can be any portion of the $NAD^+$ dependent DNA ligase adenylation domain, including a fragment at least 5 amino acids in length, at least 10 amino acids in length, at least 20 amino acids in length, at least 30 amino acids in length, at least 50 amino acids in length, at least 70 amino acids in length, at least 90 amino acids in length, at least 120 amino acids in length, at least 150 amino acids in length, at least 200 amino acids in length, at least 250 amino acids in length, at least 300 amino acids in length, or more than 300 amino acids in length. The fragment can comprise amino acids from outside the adenylation domain including any number of amino acids N-terminal or C terminal to the adenylation domain, further including all amino acids N-terminal to the adenylation domain or all amino acids C-terminal to the adenylation domain.

NAD: An abbreviation of nicotinamide adenine dinucleotide. The oxidized form is referred to as $NAD^+$. The reduced form is referred to as NADH. NAD has a number of physiological roles including as an enzyme cofactor, as an oxidizing ($NAD^+$) or reducing (NADH) agent, and as a signaling molecule. NAD (without a plus-sign) is a common term that encompasses both the oxidized and reduced forms of the NAD molecule. NAD has important roles in transcription, DNA repair, cellular metabolism, and apoptosis and both NAD levels and oxidation state are considered to be important mechanisms in cancer growth and development (Chiarugi A et al, *Nat Rev Cancer* 12, 741-752 (2012); incorporated by reference herein).

Nucleic acid or nucleic acid sequence: a polymer of ribonucleic acid (RNA) or deoxyribonucleic acid (DNA). The term can be used interchangeably with the term 'polynucleotide.' A nucleic acid is made up of four bases; adenine, cytosine, guanine, and thymine/uracil (uracil is used in RNA). A coding sequence from a nucleic acid is indicative of the sequence of the protein encoded by the nucleic acid.

Operably Linked: A first nucleic acid sequence is operably linked with a second nucleic acid sequence when the first nucleic acid sequence is placed in such a way that it has an effect upon the second nucleic acid sequence. For instance, a promoter is operably linked to a coding sequence if the promoter affects the transcription or expression of the coding sequence. Operably linked DNA sequences may be contiguous, or they may operate at a distance.

Polypeptide: Any chain of amino acids, regardless of length or posttranslational modification (such as glycosylation, methylation, ubiquitination, phosphorylation, or the like). Herein as well as in the art, the term 'polypeptide' is used interchangeably with peptide or protein, and is used to refer to a polymer of amino acid residues. The term 'residue' can be used to refer to an amino acid or amino acid mimetic incorporated in a polypeptide by an amide bond or amide bond mimetic. Polypeptide sequences are generally written with the N-terminal amino acid on the left and the C-terminal amino acid to the right of the sequence.

Promoter: A promoter may be any of a number of nucleic acid control sequences that directs transcription of a nucleic acid. Typically, a eukaryotic promoter includes necessary nucleic acid sequences near the start site of transcription, such as, in the case of a polymerase II type promoter, a TATA element or any other specific DNA sequence that is recognized by one or more transcription factors. Expression by a promoter may be further modulated by enhancer or repressor elements. Numerous examples of promoters are available and well known to those of skill in the art. A nucleic acid comprising a promoter operably linked to a nucleic acid sequence that codes for a particular polypeptide can be termed an expression vector.

Purification: Purification of a polypeptide or molecular complex may be achieved by any method now known or yet to be disclosed. In some examples, purification is achieved by contacting the complex with a reagent that binds to a component of the complex to the exclusion of other components.

Recombinant: A recombinant nucleic acid or polypeptide is one that has a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques. A recombinant polypeptide can also refer to a polypeptide that has been made using recombinant nucleic acids, including recombinant nucleic acids transferred to a host organism that is not the natural source of the polypeptide.

Sequence homology: Sequence homology between two or more nucleic acid sequences or two or more amino acid sequences, may be expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The NCBI Basic Local Alignment Search Tool (BLAST) (Altschul et al., J. Mol. Biol. 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site. BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75). For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or SWISS-PROT database. Queries searched with the blastn program are filtered with DUST (Hancock and Armstrong, 1994, Comput. Appl. Biosci. 10:67-70). In addition, a manual alignment can be performed. Proteins with even greater similarity will show increasing percentage identities when assessed by this method, such as at least about 50%, 60%, 70%, 75%, 80%, 85%, 90%, 95%, 98%, 99%, or 100% sequence identity.

When aligning short peptides (fewer than around 30 amino acids), the alignment is to be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 50%, 60%, 70%, 75%, 80%, 85%, 90%, 95%, 98%, or 99% sequence identity to a protein. When less than the entire sequence is being compared for sequence identity, including a comparison of a dominant negative GW182 polypeptide, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

A pair of proteins or nucleic acids with 50%, 60%, 70%, 75%, 80%, 85%, 90%, 95%, 98%, or 99% identity to one another can be termed 'homologs,' particularly if they perform the same function as one another, even more particularly if they perform the same function to substantially the same degree, and still more particularly if they perform the same function substantially equivalently. One of skill in the art in light of this disclosure, particularly in light of the Examples below, would be able to determine without undue experimentation whether or not a given protein or nucleic acid sequence with 50%, 60%, 70%, 75%, 80%, 85%, 90%, 95%, 98%, or 99% identity to the sequences listed herein is a homolog to the sequences listed herein. Homologs need not be the same length as the biological molecules listed herein and may include truncations (fewer amino acids or nucleotides) or extensions (more amino acids or nucleotides) than the biological molecules listed herein.

Recombinant NAD$^+$ Biosensor Polypeptides

Disclosed herein is a recombinant NAD$^+$ biosensor polypeptide that can detect free NAD$^+$ in solution as well as in a cell. The polypeptide includes a fluorescent protein and two fragments of an NAD$^+$ dependent DNA ligase adenylation domain. One fragment of the NAD$^+$ dependent DNA ligase adenylation domain is placed N-terminal relative to the fluorescent protein. The second fragment is placed C-terminal relative to the fluorescent protein. The two DNA ligase adenylation domain fragments bind NAD$^+$ and then change the emission spectrum of the fluorescent protein relative to when NAD$^+$ is not bound.

The NAD$^+$ dependent DNA ligase adenylation domain can be derived from any DNA ligase that requires NAD$^+$ as a cofactor for catalysis. Such ligases can be derived from any organism including archea, prokaryotic organisms, eukaryotic organisms, or viruses. In some examples, the ligase is derived from E. coli. In other examples, the ligase is derived from E. faecalis. In still other examples, the ligase is derived from thermophilic bacteria. One of skill in the art in light of this disclosure can identify an NAD$^+$ dependent DNA ligase through, for example, sequence homology and further identify the adenylation domain of the NAD+ dependent DNA ligase.

One fragment of the adenylation domain is derived from nucleic acids at or near the N-terminal portion of the adenylation domain (which, in some examples includes the N-terminus of the protein.) In one example, wherein the NAD$^+$ dependent DNA ligase is derived from Enterococcus faecalis, such a fragment can include amino acids 1-100 of the adenylation domain or smaller fragments such as amino acids 1-78, amino acids 2-78, amino acids 1-76, amino acids 5-78, amino acids 5-76, amino acids 1-70, amino acids 2-70, amino acids 5-70, or smaller fragments.

The second fragment of the adenylation domain is derived from nucleic acids at or near the C-terminal portion of the adenylation domain. In the example wherein the NAD$^+$ dependent DNA ligase is derived from Enterococcus faecalis, such a fragment can include amino acids 71-317 of the adenylation domain, amino acids 77-317 of the adenylation domain, amino acids 78-317 of the adenylation domain, amino acids 70-302 of the adenylation domain, or smaller fragments.

One of skill in the art would be able to use this disclosure to (a) select any NAD$^+$ dependent DNA ligase from any organism, (b) identify the adenylation domain of the selected NAD$^+$ dependent DNA ligase, and (c) select a set of fragments from the adenylation domain to place N-terminal and C-terminal from a fluorescent protein and determine whether or not the emission spectrum of the fluorescent protein changes when the polypeptide is in the presence of NAD$^+$, thereby recreating the disclosed biosensor without undue experimentation. The fragments can but need not include all amino acids of the adenylation domain and can also include amino acids outside of the adenylation domain. In some examples, the fragment comprising amino acids at or near the N-terminal portion of the adenylation domain is positioned N-terminal to the fluorescent protein while the fragment comprising amino acids at or near the C-terminal portion of the adenylation domain are positioned C-terminal to the fluorescent protein.

In some examples, the biosensor comprises a first peptide linker. The linker can be between either the first fragment and the fluorescent protein or the second fragment and the fluorescent protein. The linker can be of any appropriate length including 50 amino acids, 40 amino acids, 30 amino acids, 25 amino acids, 15 amino acids, 10 amino acids, 8 amino acids, 6 amino acids, 5 amino acids, 3 amino acids, 2 amino acids, or 1 amino acid. One of skill in the art in light of this disclosure can select an appropriate linker to place as described herein in the described biosensor and determine whether or not the addition of the linker provides improvements in the NAD$^+$ detection capabilities of the biosensor, thereby recreating the disclosed biosensor without undue experimentation. In further examples, the linker is 10 amino acids in length. In still further examples, the linker has the sequence of SEQ ID NO: 3 or SEQ ID NO: 4.

In examples where the biosensor comprises a first peptide linker, the biosensor can further comprise a second peptide linker positioned between the other fragment and the fluorescent protein. For example, if the first linker is between the first fragment and the fluorescent protein, then the second linker is between the second fragment and the fluorescent protein. The second linker can also be any linker of appropriate length as described above.

The biosensor can further comprise additional elements including protein tags or localization sequences (such as a nuclear export sequence, a nuclear localization sequence or a mitochondrial localization sequence), a label (such as a fluorescent label), modified amino acids, artificial amino acids, and the like.

EXAMPLES

The following examples are illustrative of disclosed methods. In light of this disclosure, those of skill in the art will recognize that variations of these examples and other examples of the disclosed method would be possible without undue experimentation.

Example 1

Referring now to FIG. 13A, one example of the biosensor includes a polypeptide comprising (from N-terminus to C-terminus) a FLAG® tag of SEQ ID NO: 11, an HA tag of SEQ ID NO: 12; a second fragment of an NAD+ dependent DNA ligase adenylation domain (exemplified by SEQ ID NO: 2); a fluorescent molecule (exemplified by cpVenus (SEQ ID NO: 5)); a linker (exemplified by SEQ ID NO: 3); and a first fragment of an NAD+ dependent DNA ligase (exemplified by SEQ ID NO: 1). A polypeptide exemplifying the biosensor of FIG. 13A is a polypeptide of SEQ ID NO: 6.

Example 2

Referring now to FIG. 13B, another example of the biosensor includes a polypeptide comprising (from N-terminus to C-terminus) a FLAG® tag of SEQ ID NO: 11, an HA tag of SEQ ID NO: 12; a mitochondrial localization sequence (exemplified by SEQ ID NO: 13) a second fragment of an NAD+ dependent DNA ligase adenylation domain (exemplified by SEQ ID NO: 2); a fluorescent molecule (exemplified by cpVenus (SEQ ID NO: 5)); a linker (exemplified by SEQ ID NO: 3); and a first fragment of an NAD+ dependent DNA ligase (exemplified by SEQ ID NO: 1). A polypeptide exemplifying the biosensor of FIG. 13B is a polypeptide of SEQ ID NO: 7.

Example 3

Referring now to FIG. 13C, a further example of the biosensor includes a polypeptide comprising (from N-terminus to C-terminus) a FLAG® tag of SEQ ID NO: 11, an HA tag of SEQ ID NO: 12; a nuclear export signal (exemplified by SEQ ID NO: 14) a second fragment of an NAD+ dependent DNA ligase adenylation domain (exemplified by SEQ ID NO: 2); a fluorescent molecule (exemplified by cpVenus (SEQ ID NO: 5)); a linker (exemplified by SEQ ID NO: 3); and a first fragment of an NAD+ dependent DNA ligase (exemplified by SEQ ID NO: 1). A polypeptide exemplifying the biosensor of FIG. 13C is a polypeptide of SEQ ID NO: 8.

Example 4

Referring now to FIG. 13D, yet another example of the biosensor includes a polypeptide comprising (from N-terminus to C-terminus) a FLAG® tag of SEQ ID NO: 11, an HA tag of SEQ ID NO: 12; a nuclear localization signal (exemplified by SEQ ID NO: 15); a second fragment of an NAD+ dependent DNA ligase adenylation domain (exemplified by SEQ ID NO: 2); a fluorescent molecule (exemplified by cpVenus (SEQ ID NO: 5)); a linker (exemplified by SEQ ID NO: 3); and a first fragment of an NAD+ dependent DNA ligase (exemplified by SEQ ID NO: 1). A polypeptide exemplifying the biosensor of FIG. 13D is a polypeptide of SEQ ID NO: 9.

Example 5

Referring now to FIG. 13E still another example of the biosensor includes a polypeptide comprising (from N-terminus to C-terminus) a FLAG® tag of SEQ ID NO: 11, an HA tag of SEQ ID NO: 12; a second linker (exemplified by SEQ ID NO:4) a second fragment of an NAD+ dependent DNA ligase adenylation domain (exemplified by SEQ ID NO: 2); a fluorescent molecule (exemplified by SEQ ID NO: 5); a first linker (exemplified by SEQ ID NO: 3); and a first fragment of an NAD+ dependent DNA ligase (exemplified by SEQ ID NO: 1). A polypeptide exemplifying the biosensor of FIG. 13E is a polypeptide of SEQ ID NO: 10.

Example 6—Methods

Flow Cytometry:
HEK293T cells stably expressing the biosensor AB0 K44L D210N were harvested in DMEM with 10% fetal bovine serum. Data acquisition and analysis were performed on an LSRII flow cytometer using 488-nm and 405-nm lasers. Green and red fluorescence were collected through a 500- to 560-nm or 400- to 480 nm bandpass filter, respectively. 10,000 cells within the gated region were analyzed. Data is presented using the software FlowJo®.

Cell Culture:
A stable HEK293T cell line expressing NADlight sensor AB0 K44L D210N was generated using viral transduction and puromycin selection (1 ug/ml). Cells were maintained in DMEM with 10% fetal bovine serum.

Imaging:
HEK293T cells expressing the NADlight sensor AB0 K44L D210N with either an NLS or NES localization tag were taken using a Nikon/Yokogawa CSU-W1 spinning disk confocal microscope using a 100× objective.

Fluorometry:
Fluorescence emission spectra were recorded using a PTI steady-state fluorescence spectrophotometer. Excitation spectra were captured at 530 nm while exciting from 350 to 515 nm. Emission spectra were measured by excitation at 405 nm or 488 nm while scanning the fluorescence intensity of 475 to 600 nm.

Example 7—NAD+Biosensor Reveals Multiple Sources for Mitochondrial NAD+

Nicotinamide adenine dinucleotide (NAD+) is an essential substrate for sirtuins and PARPs. NAD+-consuming enzymes localize to the nucleus, cytosol, and mitochondria. Fluctuations in NAD+ levels within these subcellular compartments are thought to regulate the activity of NAD+-consuming enzymes; however, a lack of methods for measuring compartmentalized NAD+ in cells has precluded direct evidence for this type of regulation. Disclosed herein is recombinant fluorescent biosensor that can be used to monitor free NAD+ levels in subcellular compartments. Using the disclosed biosensor, it was determined that the concentration of free NAD+ in the nucleus and cytoplasm approximates the Michaelis constant ($K_m$) for nuclear and cytoplasmic sirtuin and PARP enzymes. Systematic knockdown of enzymes that catalyze the final step of NAD+ biosynthesis revealed cell-specific mechanisms for maintaining mitochondrial NAD+ levels.

Beyond its well-known role in reversible redox reactions, NAD+ has emerged as an essential substrate for two major enzyme families involved in post-translational modifications: sirtuins (SIRT1-7, human numbering) and ADP-ribosyltransferases (ARTD1-17/PARPs1-16 in humans) (Canto C et al, *Cell Metab* 22, 31-53 (2015); incorporated by reference herein). While sirtuins catalyze protein deacylation whereas ARTDs catalyze poly and mono-ADP-ribosylation, both types of enzymes work by a common mechanism—the cleavage of a glycosidic bond between nicotinamide and ADP-ribose. This reaction results in the irreversible consumption of NAD+ (Sauve A A et al, *Biochemistry* 40, 15456-15463 (2001) and Hassa P O et al, *Microbiol Mol Biol Rev* 70, 789-829 (2006); both of which are incorporated by reference herein). As a consequence of these NAD+ cleavage events, cells rely heavily on salvage pathways that recycle the nicotinamide generated by these NAD+-consuming enzymes to maintain NAD+ levels above a critical threshold.

Nicotinamide phosphoribosyltransferase (NAMPT), the enzyme that converts nicotinamide to nicotinamide mononucleotide (NMN), is essential for maintaining NAD+ levels in cells (Revollo J R et al, *J Biol Chem* 279, 50754-50763 (2004); incorporated by reference herein). The conversion of NMN to NAD+ is catalyzed by three enzyme isoforms known as NMN adenyltransferases (NMNAT1-3) that are differentially localized in cells: NMNAT1 is located in the nucleus; NMNAT2 cytosol-facing in the Golgi; and NMNAT3 is located in mitochondria. The differential localization of the NMNATs suggests that there are distinct subcellular pools of NAD+. Local fluctuations in NAD+ levels are hypothesized to regulate the activity of the NAD+- consuming enzymes, which are also highly compartmentalized (Koch-Nolte F et al, *FEBS Lett* 585, 1651-1656 (2011); Imai S and Guarente L, *Trends Cell Biol* 24, 464-471 (2014); and Houtkooper R H et al, *Endocr Rev* 31, 194-223 (2010); incorporated by reference herein). That said, there is no direct experimental evidence for the compartmentalization of NAD+ because free NAD+ (i.e. NAD+ that is available as a substrate) within these subcellular compartments is undetectable using current methods.

Disclosed herein is a recombinant nicotinamide adenine dinucleotide (NAD$^+$) biosensor polypeptide that can be used to measure free NAD+ levels within subcellular compartments. This sensor comprises a circularly-permuted Venus fluorescent protein (cpVenus) and two fragments of an NAD+-binding domain derived from bacterial DNA ligase (FIG. 14A) (Gajiwala K S and Pinko C, *Structure* 12, 1449-1459 (2004); incorporated by reference herein). Point mutations were introduced to prevent NAD+ consumption and to allow monitoring of NAD+ within the predicted physiological range. The purified sensor and cpVenus (FIG. 18) had major excitation peaks at ~500 nm that fluoresced at ~520 nm (FIG. 14B). The addition of NAD+ decreased sensor fluorescence (ex. 488 nm) in a dose-dependent manner; in contrast, NAD+ concentrations up to 1 mM minimally affected cpVenus fluorescence (FIGS. 14B and 14C).

A second excitation peak at 405 nm was unaffected by NAD+ binding (FIG. 14C and FIG. 19), which allowed ratiometric (488/405 nm) measurements for normalizing sensor expression levels (FIGS. 20A and 20B). In vitro, the apparent $K_d$(NAD+) of the sensor was ~65 µM (FIG. 14D). Absorbance measurements revealed two major species at ~415 nm and ~488 nm that appeared to interconvert upon NAD+ addition around a ~450 nm isosbestic point (FIG. 21). This suggested that the NAD+-bound species loses its fluorescence at 488 nm, converting to a species that absorbs at 415 nm but is non-fluorescent, possibly due to out-of-plane distortion or internal quenching of the fluorophore upon NAD+ binding. Accordingly, NAD+ did not affect the fluorescence lifetime following 488 nm excitation (FIGS. 22A and 22B), providing further evidence that fluorescence following 488 nm excitation solely represents the unbound fraction.

Elution of NAD+ from the sensor returned the fluorescence to that of a control sample, confirming that NAD+ binding to the sensor was reversible (FIG. 14E). Fluorescence was also monitored in real time in the presence of glyceraldehyde 3-phosphate dehydrogenase (GAPDH), which has a higher affinity for NAD+ than the sensor and thereby competes for free NAD+. This reaction was performed with equimolar GAPDH in the absence of substrate to minimize NAD+ reduction. An almost immediate recovery of fluorescence was observed upon GAPDH addition (FIG. 14F).

To determine the specificity of the sensor for NAD+, sensor fluorescence was evaluated in the presence of related mononucleotides, dinucleotides, and NAD+ precursors (FIG. 14G). Only NAD+ resulted in decreased sensor fluorescence. The absolute fluorescence intensities of the sensor and cpVenus displayed similar sensitivities to pH and, importantly, the NAD+-dependent responses of the sensor were similar from pH 6.5-8.0 (FIG. 23A, 23B, 23C, 23D). Thus, pH effects can be accommodated by normalizing to cpVenus. Fluorescence intensity was slightly affected by temperature but there were no significant changes in the $K_d$ value of the unbound pool between 20-37° C. (FIG. 24A, 24B, 24C).

Localization sequences were used to direct the sensor to the nucleus, cytoplasm, and mitochondria (FIG. 15A and FIG. 25A, 25B, 25C). Addition of these sequences did not affect sensor responses to NAD+ in vitro (FIG. 26). Mammalian cells predominantly rely on the NAMPT-dependent salvage pathway for NAD+ biosynthesis (Revollo et al, 2004 supra), and presumably all subcellular compartments would be affected by NAMPT inhibition. To test this idea, clonal HEK293T lines stably expressing the localized sensors or their corresponding cpVenus control were generated. Cells were treated with FK866, a potent inhibitor of NAMPT, and NAD+ depletion in different compartments was monitored by live flow cytometry (FIG. 15B). FK866 increased sensor fluorescence in all compartments, indicating a reduction in NAD+ levels. Fluorescence was also monitored in cells expressing the cytoplasmic sensor using live microscopy (FIG. 15C). Treatment with FK866 began to decrease NAD+ levels in the majority of cells within 1 hour; by 3 hours pockets of NAD+ decreases were observed, which spread throughout the cytoplasm. These NAD+-depleted pockets varied in size and localization and grew over time, potentially reflecting the local activity of NAD+ consuming enzymes.

In further experiments, siRNAs that target NAMPT were added to the cells (FIG. 15D). NAMPT depletion significantly increased cytoplasmic sensor fluorescence in all compartments (FIG. 27). Importantly, nicotinamide riboside (NR) increased NAD+ levels in these cells through a parallel pathway that utilizes NR kinase to bypass NAMPT (Bieganowski P and Brenner C, *Cell* 117, 495-502 (2004); incorporated by reference herein) (FIG. 15E). NR itself was not recognized by the sensor (FIG. 14G) and did not alter sensor fluorescence nonspecifically (FIG. 28).

To verify that the sensor itself did not significantly affect free NAD+ levels in cells, the activity of the cytoplasmic NAD+-consumer PARP10 was monitored using an aminooxy-alkyne (AO-alkyne) clickable probe that can detect PARP auto-ADP ribosylation (Morgan R K and Cohen M S, *ACS Chem Biol* 10, 1778-1784 (2015); incorporated by reference herein). Expression of the localized sensors did not affect activity of PARP10, whose $K_m$ for NAD+ is similar to the sensor in vitro (Kleine et al, 2008 supra) (FIG. 15F).

The free NAD+ concentration in the nucleus and cytoplasm has been debated. To calibrate the sensor, cells were permeabilized with digitonin to allow internal NAD+ levels to equilibrate with concentrations external to the cell and fluorescence monitored by flow cytometry. Equilibration was assessed using propidium iodide (PI), whose molecular weight is similar to that of NAD+ (FIG. 29). NAD+ decreased fluorescence of the cytoplasmic sensor in a dose-dependent manner, (apparent $K_d$ ~300 µM) (FIG. 16A), and minimally affected cpVenus (FIG. 30). The mean of the fluorescence ratio (488/405 nm) for the cytoplasmic sensor in non-permeabilized HEK293T cells relative to cpVenus was interpolated to reveal a free NAD+ value of 105.8 μM (95% Cl, 92.3 μM to 121.7 μM). Using the same strategy, it was determined that the free nuclear NAD+ level was 108.8 μM (95% Cl, 87.3 μM to 136 μM) (FIG. 31). To confirm these calculations, flow cytometry was used to examine the fluorescence of the cytoplasmic sensor in populations of HeLa cells that were partially permeabilized (FIG. 16B). When equilibrated with either 500 μM or 1 mM NAD+, cytoplasmic fluorescence of the permeabilized cell population decreased, indicating an increase in NAD+. In contrast, equilibration with media containing no external NAD+ increased fluorescence, likely due to NAD+ diffusion. Equilibration with 100 μM NAD+ did not change the level of fluorescence, suggesting that cytoplasmic free NAD+ in HeLa cells approximated this value. Similar effects were observed in an analogous experiment using adherent HeLa cells permeabilized with saponin (FIG. 29) and analyzed by live microscopy (FIG. 16C). Many NAD+ consuming enzymes have $K_m$ values for NAD+ reported in the literature to be around 100 μM (Canto et al, 2015 supra). This supports the hypothesis that these NAD+ consuming enzymes are regulated by local NAD+ fluctuations. The similarity in nuclear and cytoplasmic NAD+ levels suggests that NAD+ is readily exchangeable between the nucleus and the cytoplasm.

A major unanswered question is how subcellular pools of NAD+ in the nucleus, cytoplasm, and mitochondria are established and maintained. To address this, validated siRNAs (FIG. 32) were used to systematically deplete the enzymes that catalyze the final step of NAD+ biosynthesis in each of these subcellular compartments: nuclear NMNAT1, Golgi cytosol-facing NMNAT2, and mitochondrial NMNAT3 (FIG. 33) (Berger F et al, *J Biol Chem* 280, 36334-36341 (2005); incorporated by reference herein). Depletion of NMNAT2 decreased cytoplasmic NAD+, consistent with its subcellular expression pattern (FIG. 34A). Nuclear NAD+ levels, however, were not affected (FIG. 34A), indicating that NMNAT1 is sufficient to meet the nuclear NAD+ demand but cannot fully compensate for a decrease in cytoplasmic levels; this is consistent with the lethality of the individual animal knockout models (Conforti L et al, *FEBS J* 278, 2666-2679 (2011); Hicks A N et al, *Neurourol Urodyn* 32, 1130-1136 (2013); both of which are incorporated by reference herein). Depletion of NMNAT1 did not significantly change cytoplasmic NAD+ levels (FIG. 34B). It was then asked whether the relatively similar levels of NMNAT1 and NMNAT2 in HEK293T cells masked the NMNAT1 contribution to this compartment. HeLa cells, which express much less NMNAT2 (FIG. 35) than other cells were then examined. In HeLa cells, the same depletion of NMNAT1 significantly decreased cytoplasmic NAD+ (FIG. 34C). Together, these data demonstrate that NMNAT1 can contribute to the cytoplasmic NAD+ pool, and highlight cell-type dependent differences in NAD+ regulation.

The source of mitochondrial NAD+ was then examined. Mitochondria are impermeable to NAD+ and this pool does not freely diffuse to the nucleocytoplasm (FIG. 37). Thus the mitochondrial NMNAT isoform, NMNAT3, is thought to generate mitochondrial NAD+. Consistent with this idea, depleting NMNAT3 in HEK293T cells significantly decreased mitochondrial NAD+ levels (FIG. 17A). Surprisingly, we found that depletion of NMNAT2 also decreased mitochondrial NAD+ levels (FIG. 17A). This suggests that NAD+ made in the cytoplasm could be provided to the mitochondria and that NMN is not the sole source.

To confirm this, HeLa cells, which contain very low levels of NMNAT3, were examined. NMNAT3 depletion did not affect mitochondrial NAD+ levels in HeLa cells indicating that the mitochondrial pool in this cell type does not depend on NMN (FIG. 37). Despite its low expression, NMNAT2 was active in HeLa cells, as its depletion decreased cytoplasmic NAD+ (FIG. 38). Depletion of NMNAT2 in HeLa cells also decreased mitochondrial NAD+. (FIG. 17B). This depletion was not rescued by addition of NR, implying that cytoplasmic NAD+, and not NMN, is responsible for maintaining mitochondrial NAD+ levels in HeLa cells (FIG. 17B). Thus, there appear to be multiple mechanisms for maintaining mitochondrial NAD+ in different cell types; conversion of NMN by NMNAT3 and active transport of cytoplasmic NAD+. An NAD+ transporter has been identified in bacteria (Haferkamp I et al, Nature 432, 622-625 (2004); incorporated by reference herein), yeast (Todisco S et al, J Biol Chem 281, 1524-1531 (2006); incorporated by reference herein), and plants (Palmieri F et al, J Biol Chem 284, 31249-31259 (2009); incorporated by reference herein), although a mammalian homologue has not yet been identified.

Materials and Methods

Sensor Construction:

A cDNA fragment encoding the bacterial NAD+-dependent DNA ligase binding domain was obtained by PCR of genomic DNA of *E. faecalis* (OHSU isolate). Subdomains from cpVenus and the ligase NAD+ binding domain were PCR amplified with 20 nt overlapping ends to facilitate Gibson Assembly into pENTR-6 (modified from pENTR-4 to include additional restriction sites). Point mutations (K44L and D210N) were introduced via site-directed mutagenesis. After sequence validation, the final construct was inserted into lentiviral expression vector pCMVFlag-HA-CcdB-IRES-puro using Gateway Cloning.

Protein Purification:

The sensors and controls were purified in batch format from mammalian HEK293T cells via their N-terminal Flag epitope tag, using anti-Flag M2 Affinity Gel (Sigma) and lysis buffer (50 mM Tris pH 7.4, 150 mM NaCl, 1 mM EDTA, 10 mM NaF, 0.5% NP-40, 1 mM DTT, and Complete Protease Inhibitor cocktail). Protein was eluted with 500 μg/mL 3× Flag peptide and dialyzed against 100 mM Tris pH 7.4, 150 mM NaCl, 0.5 mM DTT, 100 μM PMSF, 1 mM EDTA, and 50% glycerol. Bradford assays were used to quantify the concentration in each batch and aliquots were flash frozen in liquid nitrogen for storage at −80° C.

Fluorescence and Absorbance Spectroscopy:

Steady-state fluorescence intensity measurements were performed using a Photon Technology International Quanta Master fluorimeter. Excitation spectra were monitored at 530 nm and emission spectra were measured by excitation at 488 nm and 405 nm. Slit widths used gave 8 nm bandpass for excitation and 44 nm bandpass for emission. Absorbance spectroscopy was performed on a Shimadzu 1601 spectrophotometer. Temperature was controlled with a water jacket and monitored using an Omega Thermistor.

NAD+ Washout:

Purified sensor (2 μM) was incubated with either 0μ or 500 μM NAD+ in a total of 75 μL and evaluated for its fluorescence excitation and emission spectra. Each sample was then passed over a pre-equilibrated (50 mM Tris pH 7.4, 150 mM NaCl) micro buffer exchange column (Biorad microbiospin P30), washed, and eluted in 75ul buffer volume for reevaluation of fluorescence.

Competition for Free NAD+:

Fluorescence emission of 250 nM purified sensor was monitored at 520 nm following excitation at 488 nm over time. Three 1-second exposures were obtained every 30 seconds at 20° C. in 100 mM HEPES pH7.4, 150 mM NaCl, 10 mM $MgCl_2$. At the 240 timepoint, NAD+ was added to a final concentration of 10 µM; at the 600 second timepoint, full-length active human GAPDH (AbCam) was added to a final concentration of 11.7 µM. Fluorescence measurements were corrected for dilution factor. Mean±SD, n=2.

Fluorescence Lifetime Measurements:

Fluorescence lifetime measurements were performed on a PicoQuant FluoTime 200 time correlated single photon counting instrument (PicoQuant, Berlin), outfitted with a Hamamatsu micro-channel plate detector. Decays were measured with the polarizers at the magic angle and with 16 nm bandpass emission slits. Excitation was achieved using a pulsed diode laser of 485 nm, which yielded an Instrument Response Function (IRF) of 128 ps (FWHM), measured using a Ludox solution. Emission from the samples was collected at 525 nm, with an additional 520 nm long-pass filter on the detector side of the sample. The fluorescence decays were fit by means of PicoQuant software, using an exponential decay model $[I(t)=\Sigma_{i-1}^{n} A_i e^{-t/\tau_i}]$ where $A_i$ is the amplitude of the $i^{th}$ component, in counts, in the first range fitting channel and $\tau_i$ is the lifetime of the $i^{th}$ component.

Flow Cytometry:

Data was collected on a special order BD LSRFortessa using 488-1 (Ex. 488 nm, Em. 525/50) and 405-2 (ex. 405 nm, Em. 515/20) for the sensor, and Ex. 561-3 (ex. 561, em 670/30) for PI intensity. Cells were gated to exclude debris, a standard doublet-exclusion was performed, and $1 \times 10^4$ fluorescent cells were evaluated per condition. Data were analyzed and plotted with FlowJo X. Sensor 488/405 ratiometric values were normalized to the appropriate cpVenus and experimental controls. An Amnis instrument (EMD Millipore) was used to capture images during flow cytometry analysis.

Imaging and Quantitation:

Live cell imaging was done on a fully motorized Nikon TiE stand with a Yokogawa W1 spinning disk confocal unit. Instrumentation for this project included a motorized stage in x and y for point-revisiting; z-axis control for fast piezo-based positioning and continuous focus-drift compensation for live cell imaging; dual-pinhole array for improved optical sectioning, a high powered Agilent laser launch; split simultaneous acquisition on two Andor Zyla 5.5 sCMOS cameras; and a 100×1.49 Apo TIRF objective. During imaging, cells were maintained in 5% $CO_2$ at 34° C. Cells were excited at 488 nm and monitored with emission 525/25 nm. For each condition, at least 5 fields containing approximately 50-100 cells were used for quantification of pixel intensity using Metamorph software. The mean intensity per field of each siRNA was normalized to the scramble condition to obtain the normalized intensity measurement.

Statistical Analysis:

Ratio of ratios: Data were analyzed using a linear mixed-effect model fit by Restricted Maximum Likelihood (REML) with STATA/IC 14 software. Fluorescence intensity was log transformed prior to analysis to help stabilize variance and limit the impact of outliers. P value calculations were performed on the ratio of ratios for $$\left(\frac{F_{Sensor}}{F_{SensorScram}}\right) \bigg/ \left(\frac{F_{cpV}}{F_{cpVScram}}\right).$$

Two-way repeated measurement ANOVA: Analysis was performed using GraphPad Prism6, comparing mean values per column and row. An adjusted p-value from Sidak multiple comparison test was reported.

Statistical calibration estimation of error: The two major variance components ($SD_{replicates}$ and $SD_{lack\ of\ fit}$) reported by GraphPad Prism6 from the sigmoidal regression were used to calculate SDx for the interpolated x value. 2×SDx was used for the 95% confidence interval (95% CI) and reported as $10^{x \pm (2 \times SDx)}$.

qPCR: Total RNA was extracted from cells using RNeasy (Qiagen) and 1 µg was used as the template for cDNA using random-15mer primers and reverse transcriptase MMLV (Life Technologies). Forty cycles of hot-start quantitative-PCR was performed on a DNAEngine Opticon system (MJ Research) with SYBR green. NAMPT-qPCR-F: agggtta-caagttgctgccacc; NAMPT-qPCR-R: ctccaccagaaccgaagg-caat; NMNAT1-qPCR-F: gtggaaagagactctgaaggtgc; NMN-AT1-qPCR-R: cttgtgtttcagtccacttcctc; NMNAT2#A-F: aga-tatggaggtgattgttggtg; NMNAT2#A-R: tttgtatttgcggagtattga-gg; NMNAT3-qPCR-F: ggatggagacagtgaaggtgct; NMN-AT3-qPCR-R: gtcgagaagagtgccttgccat; GAPDH-e1-F: cat-gacaactttggtatcgtggaagga; GAPDH-e1-R: cacagtcttctgggtg-gcagtga.

Antibodies and siRNAs:

Antibodies for western blotting and immunofluorescence (IF) were incubated overnight at 4° C. in 5% milk TBST (westerns) or 2% BSA, 1% horse serum, 0.1% TritonX-100 in PBS (IF). Dilutions were as follows: anti-NAMPT (Bethyl, 1:10 000); anti-NMNAT1 (Abcam, 1:100); anti-NMNAT2 (Abcam, 1:100); anti-NMNAT3 D10 (SCBT, 1:100); anti-Golgin 245 C13 (SCBT, 1:100). siRNAs were ordered from the human siGENOME library from Dharmacon (GE Healthcare), except for siScramble. siRNAs (25 nM final) were reverse transfected into cells using RNAiMax (Life Technologies) following manufacturer's protocols and effects were evaluated 72-96 hours post-transfection. siScramble: gugguccaaccgacuaauacag; siTJAP1: gccggtaccgct-cattgagct; siNAMPT #1: #D-004581-01; siNAMPT #2: # D-004581-02; siNMNAT2 #2: D-008573-02; siNMNAT2 #3: D-008573-03; siNMNAT3 #1: D-008688-01; siNMNAT3 #3: D-008688-03; siNMNAT3 #4: D-008688-03.

PARP10 Auto-ADP-Ribosylation:

HEK293Tcell lines were transfected with pCMV-GFP-PARP10. Twenty-four hours post transfection, cells were treated for 1 hour with AO-alkyne (100 µM) and p-phenylenediamine (PDA, 10 mM) to detect PARP10 cellular activity. Method is reported in (Morgan and Cohen, 2015 supra). Briefly, cell pellets were lysed in 25 mM HEPES pH 7.5, 50 mM NaCl, 10% glycerol, 1% NP-40, and protease inhibitors. 80 µg of whole cell lysate was used for click conjugation of the alkyne-labeled PARP10 with 100 µM biotin-azide (Biotin-PEG3-Azide, Click Chemistry Tools) for 1 hour at room temperature in Click Buffer (100 µM of tris[(1-benzyl-1H-1,2,3-triazol-4-yl)methyl]amine (TBTA), 1 mM CuSO4, 1 mM tris(2-carboxyethyl)phosphine hydrochloride (TCEP.HCl, Thermo Scientific Pierce) in 1×PBS+ 1% SDS). Reactions were quenched in protein loading sample buffer and assayed using Western blotting with Streptavidin-HRP (1:3333, Jackson ImmunoResearch) to detect biotinylated GFP-PARP10 and anti-GFP (1:1000 Abcam) for GFP-PARP10 and sensor.

The invention claimed is:

1. A recombinant nicotinamide adenine dinucleotide (NAD$^+$) biosensor polypeptide comprising:
   a first NAD$^+$ dependent DNA ligase adenylation domain fragment, the first fragment comprising an amino acid sequence derived from an N-terminal portion of the DNA ligase adenylation domain;
   a second NAD$^+$ dependent DNA ligase adenylation domain fragment, the second fragment comprising an amino acid sequence derived from a C-terminal portion of the DNA ligase adenylation domain; and
   a fluorescent protein;
   wherein the fluorescent protein is located between the first NAD$^+$ dependent DNA ligase adenylation domain fragment and the second NAD$^+$ DNA ligase adenylation domain fragment;
   wherein the first fragment is at least 60 amino acids in length, is derived from the N-terminal 80 amino acids of the DNA ligase adenylation domain, and comprises a sequence at least 95% identical to SEQ ID NO: 1 (LigA 2-70); and
   wherein the second fragment is at least 200 amino acids in length, is derived from the C-terminal 260 amino acids of the DNA ligase adenylation domain, and comprises a sequence at least 95% identical to SEQ ID NO: 2 (LigA 78-317).

2. The polypeptide of claim 1 wherein the first fragment is SEQ ID NO: 1.

3. The polypeptide of claim 1 wherein the second fragment is SEQ ID NO: 2.

4. The polypeptide of claim 1 wherein the second fragment is positioned toward the N-terminus of the polypeptide relative to the fluorescent protein and wherein the first fragment is positioned toward the C-terminus of the polypeptide relative to the fluorescent protein.

5. The polypeptide of claim 4 comprising a first peptide linker wherein the first peptide linker is between the first fragment and the fluorescent protein.

6. The polypeptide of claim 5 wherein the first peptide linker is between 2 and 25 amino acids in length.

7. The polypeptide of claim 6 wherein the first peptide linker is 10 amino acids in length.

8. The polypeptide of claim 7 wherein the first peptide linker has a sequence of SEQ ID NO: 3.

9. The polypeptide of claim 5 further comprising a second peptide linker.

10. The polypeptide of claim 9 wherein the second linker is positioned at the N-terminal end of the second fragment.

11. The polypeptide of claim 9 wherein the second peptide linker is between 2 and 25 amino acids in length.

12. The polypeptide of claim 11 wherein the second peptide linker is 10 amino acids in length.

13. The polypeptide of claim 12 wherein the second peptide linker has a sequence of SEQ ID NO: 4.

14. The polypeptide of claim 1 wherein the fluorescent protein is a circularly permutated fluorescent protein.

15. The polypeptide of claim 14 wherein the fluorescent protein comprises SEQ ID NO: 5.

16. The polypeptide of claim 14 further comprising one or more of a FLAG® tag, an HA tag, a nuclear export signal, a nuclear localization signal, or a mitochondrial localization signal.

17. The polypeptide of claim 16 comprising SEQ ID NO: 6; SEQ ID NO: 7; SEQ ID NO: 8; SEQ ID NO: 9; or SEQ ID NO: 10.

18. A recombinant nicotinamide adenine dinucleotide (NAD$^+$) biosensor polypeptide comprising:
   a first NAD$^+$ dependent DNA ligase adenylation domain fragment, the first fragment comprising an amino acid sequence derived from an N-terminal portion of the DNA ligase adenylation domain;
   a second NAD$^+$ dependent DNA ligase adenylation domain fragment, the second fragment comprising an amino acid sequence derived from a C-terminal portion of the DNA ligase adenylation domain; and
   a fluorescent protein comprises SEQ ID NO: 5;
   wherein the fluorescent protein is located between the first NAD$^+$ dependent DNA ligase adenylation domain fragment and the second NAD$^+$ DNA ligase adenylation domain fragment;
   wherein the first fragment comprises SEQ ID NO: 1 (LigA 2-70); and
   wherein the second fragment comprises SEQ ID NO: 2 (LigA 78-317).

19. The polypeptide of claim 18 further comprising one or more of a FLAG® tag, an HA tag, a nuclear export signal, a nuclear localization signal, or a mitochondrial localization signal.

20. The polypeptide of claim 19 comprising SEQ ID NO: 6; SEQ ID NO: 7; SEQ ID NO: 8; SEQ ID NO: 9; or SEQ ID NO: 10.

* * * * *